United States Patent
Koizumi et al.

(10) Patent No.: US 11,446,263 B2
(45) Date of Patent: Sep. 20, 2022

(54) CASPASE INHIBITOR-CONTAINING DRUG FOR TREATING OR PREVENTING DISORDERS CAUSED BY TGF-β, AND APPLICATIONS THEREOF

(71) Applicant: The Doshisha, Kyoto (JP)

(72) Inventors: Noriko Koizumi, Kyoto (JP); Naoki Okumura, Kyoto (JP)

(73) Assignee: The Doshisha, Kyoto (JP)

( * ) Notice: Subject to any disclaimer, the term of this patent is extended or adjusted under 35 U.S.C. 154(b) by 1049 days.

(21) Appl. No.: 16/065,609

(22) PCT Filed: Dec. 22, 2016

(86) PCT No.: PCT/JP2016/005216
§ 371 (c)(1),
(2) Date: Jun. 22, 2018

(87) PCT Pub. No.: WO2017/110094
PCT Pub. Date: Jun. 29, 2017

(65) Prior Publication Data
US 2021/0196656 A1      Jul. 1, 2021

(30) Foreign Application Priority Data

Dec. 24, 2015   (JP) .............................. JP2015-251787

(51) Int. Cl.
| | |
|---|---|
| *A61K 38/05* | (2006.01) |
| *A61K 38/06* | (2006.01) |
| *A61K 31/122* | (2006.01) |
| *A61K 31/4725* | (2006.01) |
| *A61K 31/165* | (2006.01) |
| *A61K 31/197* | (2006.01) |
| *A61K 45/06* | (2006.01) |
| *A61P 27/02* | (2006.01) |

(52) U.S. Cl.
CPC .......... *A61K 31/165* (2013.01); *A61K 31/122* (2013.01); *A61K 31/4725* (2013.01); *A61P 27/02* (2018.01)

(58) Field of Classification Search
CPC ...... A61K 45/00; A61K 45/06; A61K 31/165; A61K 31/4725; A61K 31/122; A61K 38/06; A61K 38/05; A61K 2300/00; A61P 27/02

See application file for complete search history.

(56) References Cited

U.S. PATENT DOCUMENTS

2016/0296505 A1   10/2016   Koizumi et al.
2016/0331736 A1   11/2016   Koizumi et al.

FOREIGN PATENT DOCUMENTS

| JP | 2003511463 A | 3/2003 |
|---|---|---|
| JP | 2014-510155 A | 4/2014 |
| WO | WO-2001/027140 | 4/2001 |
| WO | WO-2011/133964 A2 | 10/2011 |
| WO | WO-2012/139028 | 10/2012 |
| WO | WO-2014/112675 A1 | 7/2014 |
| WO | WO-2015/064768 A1 | 5/2015 |
| WO | WO-2015/072580 A1 | 5/2015 |

OTHER PUBLICATIONS

Aging—Prevention, 2021, https://www.healthline.com/health/skin/how-to-prevent-wrinkles#relax.*
FuchsDystrophy, 2021, https://www.hopkinsmedicine.org/health/conditions-and-diseases/fuchs-dystrophy.*
Wu et al., Mechanism of Mitomycin-induced apoptosis in cultured corneal endothelial cells, Molec. Visision, 1705-12 (2008).
Kim et al., Caspase Inhibitor z-VAD-FMK Inhibits Keratocyte Apoptosis but Promotes Keratocyte Necrosis, after Corneal Epithelial Scrape, Experimental Eye Res., 71(3):225-32 (2000).
Corwin et al., In vitro assessment of apoptosis and necrosis following cold storage in Human Corneal Endothelial Cells, Cryobiology, 66:355 (2013).
International Search Report issued in Connection with PCT/JP2016/005216 dated Mar. 7, 2017 with English Translation.
Reply Brief filed with the Japanese Patent Office, in connection with PCT/JP2016/005216, dated May 24, 2017.
International Preliminary Report on Patentability (English Translation) issued in connection with PCT/JP2016/005216 dated Jul. 24, 2017.

* cited by examiner

Primary Examiner — Sun Jae Yoo
(74) Attorney, Agent, or Firm — Marshall, Gerstein & Borun LLP

(57) ABSTRACT

Provided is a drug or method for treating or preventing a condition, disorder, or disease of the corneal endothelium caused by transforming growth factor-β (TGF-β) signals and/or mitochondrial abnormalities in corneal endothelial cells. The present invention provides a drug which includes caspase inhibitors, and which is for treating or preventing a condition, disorder, or disease of the corneal endothelium caused by TGF-β signals and/or mitochondrial abnormalities in corneal endothelial cells. In the preferred embodiment, the condition, disorder, or disease of the corneal endothelium is Fuchs' corneal endothelial dystrophy.

20 Claims, 22 Drawing Sheets

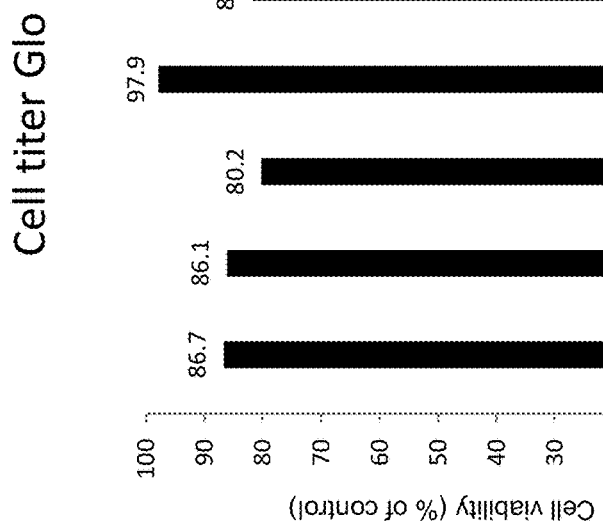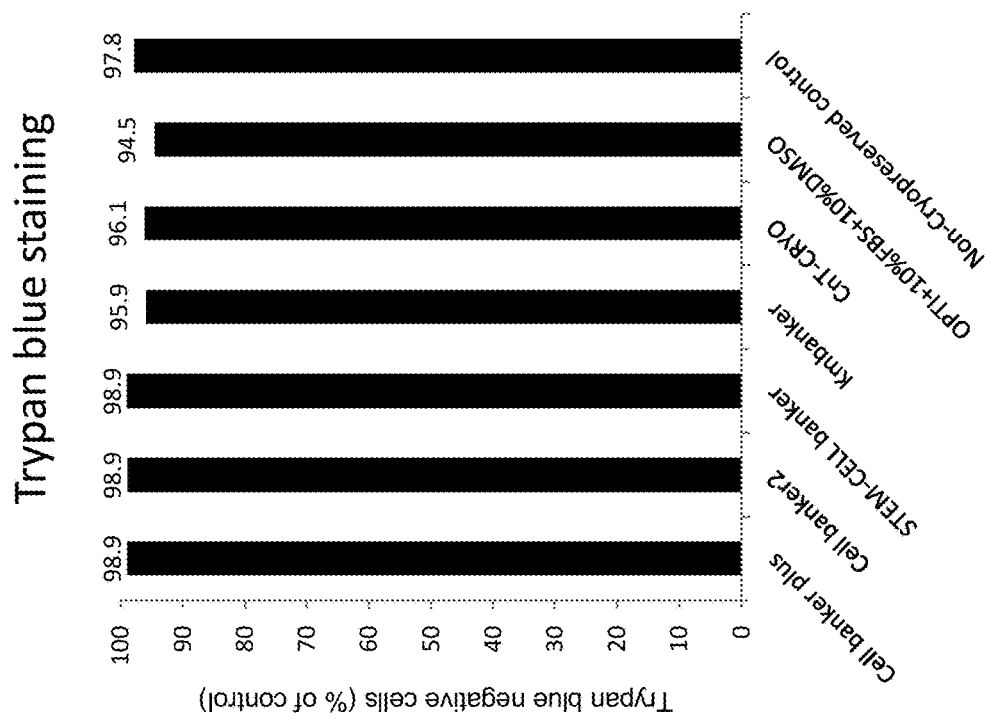
FIG. 16

FIG.19
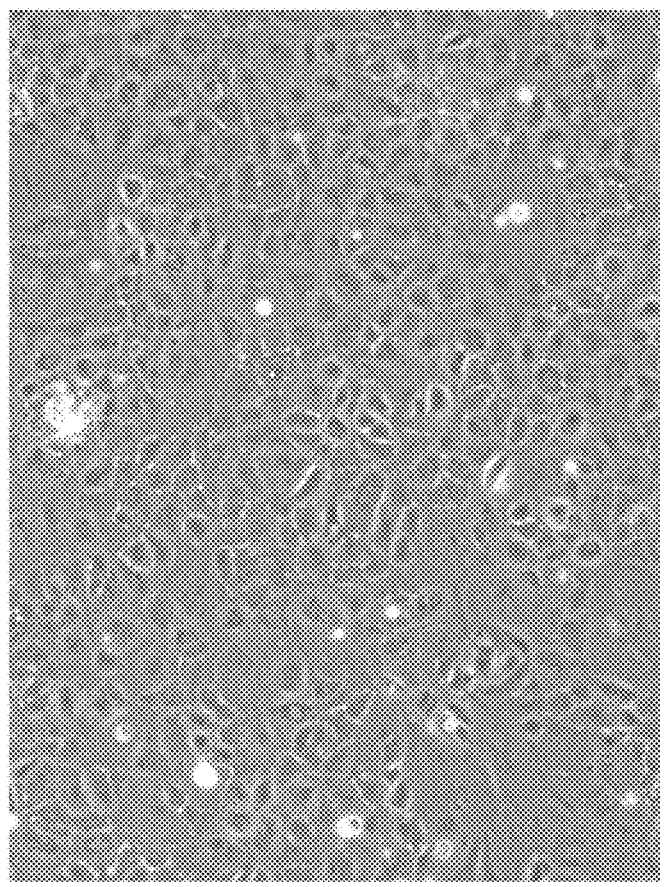
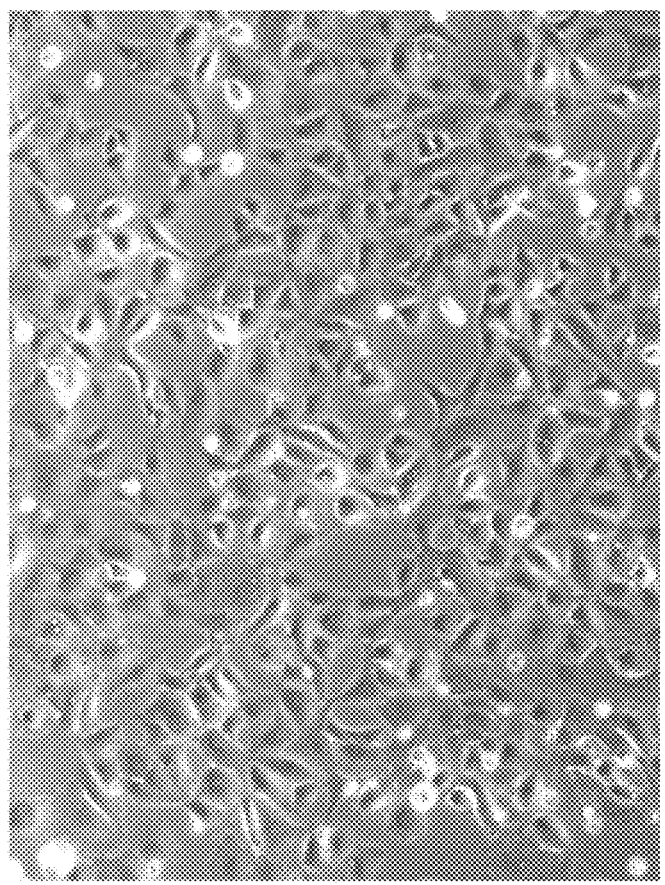

CASPASE INHIBITOR-CONTAINING DRUG FOR TREATING OR PREVENTING DISORDERS CAUSED BY TGF-β, AND APPLICATIONS THEREOF

TECHNICAL FIELD

The present invention relates to a technique or method of treating or preventing a corneal endothelial condition, disorder, or disease due to at least one of a transforming growth factor-β (TGF-β) signal and a mitochondrial abnormality in corneal endothelial cells, an agent therefor, and a technique of preserving corneal endothelial cells by applying said technique.

BACKGROUND ART

Visual information is recognized when light transmitted into the cornea, which is a transparent tissue at the frontmost part of an eyeball, reaches the retina and excites nerve cells of the retina, and a generated electric signal is transmitted through the optic nerve to the visual cortex of the cerebrum. To attain good vision, it is necessary that the cornea is transparent. The transparency of the cornea is retained by maintaining a constant water content with the pumping and barrier functions of corneal endothelial cells.

Human corneal endothelial cells are present at a density of about 3000 cells per 1 $mm^2$ at birth. Once damaged, human corneal endothelial cells have a very limited ability to regenerate. Fuchs' endothelial corneal dystrophy is a disease that causes an abnormality in endothelial cells inside the cornea and significantly reduces the density of corneal endothelial cells, resulting in edema of the cornea. The cause thereof is unknown. In Fuchs' endothelial corneal dystrophy, extracellular matrix components such as collagen or fibronectin are deposited on a part of the back surface of the Descemet's membrane, situated at the back of the cornea, resulting in guttae (Corneal guttae) and thickening of the Descemet's membrane. Guttae (Corneal guttae) and thickening of the Descemet's membrane are the causes of photophobia or blurred vision in Fuchs' endothelial corneal dystrophy patients, which significantly compromises the QOL of the patients. In this manner, extracellular matrix components such as fibronectin are associated with conditions that cause reduced visual acuity such as guttata on the corneal endothelial surface or turbid guttae, and can be the main cause of a corneal endothelial disorder associated with opacity of the cornea such as clouding, corneal haziness or leucoma. It is understood that there is no effective therapeutic method other than corneal transplant for Fuchs' endothelial corneal dystrophy. However, there is a shortage in cornea donation in Japan, where the number of patients waiting for corneal transplant is about 2600, whereas the number of corneal transplants performed in Japan is approximately 1700 annually.

For Fuchs' endothelial corneal dystrophy, culture (Non Patent Literatures 1 and 3) and immobilization (Non Patent Literature 2) of corneal endothelial cells from Fuchs' corneal dystrophy patients have been reported, but cells suitable for screening of a therapeutic drug or progression preventing drug, which maintain the features of the disease such as overproduction of extracellular matrices, have not been reported. Therefore, there is a limit to the development of a therapeutic drug thereof. Currently, there is no therapeutic drug that is used in clinical practice, so therapy is reliant on corneal transplant.

Further, Patent Literature 1 discloses a TGF-β1 inhibitor peptide for treating fibrillization and/or opacity of corneas. Patent Literature 2 discloses antibodies that bind to TGF-β1, 2, or 3. Patent Literature 3 discloses that an Nrf2 agonist or activator can be used in the therapy of corneal endothelial disorders. Patent Literature 4 discloses a peptide, which can bind to a transforming growth factor-β1 (TGF-β1) and be a potent inhibitor of bioactivity of TGF-β1 by directly binding to a cytokine. Patent Literature 5 discloses a scar formation suppressant comprising a BMP-7 polypeptide. Patent Literature 6 describes, in general terms, corneal disorders as diseases for which TGF-β inhibitory action is therapeutically or prophylactically effective.

CITATION LIST

Patent Literature

[PTL 1] Japanese National Phase PCT Laid-open Publication No. 2013-520405
[PTL 2] International Publication No. WO 2012/167143
[PTL 3] International Publication No. WO 2012/009171
[PTL 4] Japanese National Phase PCT Laid-open Publication No. 2007-525204
[PTL 5] Japanese National Phase PCT Laid-open Publication No. 2006-508169
[PTL 6] International Publication No. WO 2004/018430

Non Patent Literature

[NPL 1] Zaniolo K, et al. Exp Eye Res.; 94 (1): 22-31. 2012
[NPL 2] Azizi B, et al. Invest Ophthalmol Vis Sci. 2; 52 (13): 9291-9297. 2011
[NPL 3] Kelliher C. et al. Exp Eye Res Vol. 93 (6), 880-888, 2011

SUMMARY OF INVENTION

Solution to the Problem

The inventors have completed the present invention by discovering that a TGF-β signal causes a disorder by using an agent such as transforming growth factor-β2 (TGF-β2), and discovering that such a disorder is surprisingly treatable with a caspase inhibitor in cells of a Fuchs' endothelial corneal dystrophy corneal endothelial disorder model. The inventors have also discovered that mitochondrial abnormalities can be healed with a caspase inhibitor. The present invention has been completed by discovering the application of a caspase inhibitor for use in treating or preventing corneal endothelial disorders (especially corneal endothelial disorders in Fuchs' endothelial corneal dystrophy) due to a transforming growth factor-β (TGF-β) and/or mitochondrial abnormality. For corneal endothelial disorders such as Fuchs' endothelial corneal dystrophy, therapy or prevention has been attempted, with suppression of cell death (especially apoptosis) as the primary target, but it has been pointed out that visual function worsens due to clouding, whose primary cause is the overproduction of the extracellular matrix (ECM) (e.g., fibronectin or the like). Since cell death and extracellular matrix formation are independent events, it is preferable that both can be suppressed. In the present invention, the inventors have unexpectedly discovered that overexpression of extracellular matrix (ECM) components such as fibronectin can be suppressed by inhibiting caspase. The inventors have thereby discovered that a caspase inhibitor can be applied for the improvement, therapy, or prevention of corneal endothelial diseases due to overexpression of the extracellular matrix (e.g., guttae, thickening of the Descemet's layer, corneal haziness, leucoma, other conditions of clouding, and the like). The inventors have also discovered that a caspase inhibitor suppresses cell damage due to cryopreservation of corneal endothelial cells.

The present invention therefore provides, for example, the following items.

(Item 1)
A medicament for use in treating or preventing a corneal endothelial condition, disorder, or disease due to at least one of a transforming growth factor-β (TGF-β) signal and a mitochondrial abnormality in corneal endothelial cells, comprising a caspase inhibitor.

(Item 2)
The medicament of item 1, wherein the condition, disorder, or disease is associated with a TGF-3 signal and a mitochondrial abnormality.

(Item 3)
The medicament of item 1, wherein the mitochondrial abnormality is selected from one or more of a decrease in mitochondrial membrane potential, a morphological abnormality of mitochondria, and a decrease in mitochondrial biosynthesis.

(Item 4)
The medicament of item 1, wherein the condition, disorder, or disease is selected from the group consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), and idiopathic corneal endothelial disorder.

(Item 5)
The medicament of any one of items 1 to 4, wherein the condition, disorder, or disease comprises Fuchs' endothelial corneal dystrophy.

(Item 6)
The medicament of item 5, wherein the medicament prevents the progression of Fuchs' endothelial corneal dystrophy by suppressing a decrease in mitochondrial membrane potential of corneal endothelial cells in Fuchs' endothelial corneal dystrophy.

(Item 7)
A composition for preservation of corneal endothelial cells or culturing after preservation, comprising a caspase inhibitor.

(Item 8)
The composition of item 7, wherein the preservation is cryopreservation.

(Item 9)
A composition for promoting the growth of corneal endothelial cells, comprising a caspase inhibitor.

(Item 10)
The composition of item 9, further comprising a p38 MAP kinase inhibitor.

(Item 11)
The medicament or composition of any one of items 1 to 10, wherein the caspase inhibitor is a caspase 3 inhibitor.

(Item 11A)
The medicament or composition of any one of items 1 to 11, wherein the caspase inhibitor is a pan caspase inhibitor.

(Item 12)
The medicament or composition of any one of items 1 to 11 and 11A, wherein the caspase inhibitor is selected from the group consisting of Z-VD-FMK, Z-VAD-FMK, emricasan, and nivocasan.

(Item 13)
The medicament or composition of item 12, wherein a concentration of the Z-VD-FMK is about 3 μM to about 100 μM.

(Item 14)
The medicament or composition of item 12, wherein a concentration of the Z-VAD-FMK is about 3 μM to about 30 μM.

(Item 15)
The medicament or composition of item 12, wherein a concentration of the emricasan is about 1 μM to about 100 μM.

(Item 16)
The medicament or composition of item 12, wherein a concentration of the nivocasan is about 30 μM to about 300 μM.

(Item 17)
The medicament or composition of any one of items 1 to 11, 11A, and 12-16, wherein the caspase inhibitor is water-soluble.

(Item 18)
The medicament of any one of items 1 to 17, wherein the caspase inhibitor is provided as an eye drop.

In another aspect, the present invention provides, for example, the following items.

(Item X1)
A medicament for use in treating or preventing a corneal endothelial condition, disorder, or disease due to at least one of a transforming growth factor-β (TGF-β) signal and a mitochondrial abnormality in corneal endothelial cells, comprising a caspase inhibitor.

(Item X2)
The medicament of item X1, wherein the condition, disorder, or disease is associated with a TGF-β signal and a mitochondrial abnormality.

(Item X3)
The medicament of item X1 or X2, wherein the mitochondrial abnormality is selected from one or more of a decrease in mitochondrial membrane potential, a morphological abnormality of mitochondria, or a decrease in mitochondrial biosynthesis.

(Item X4)
The medicament of any one of items X1 to X3, wherein the condition, disorder, or disease is selected from the group consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), and idiopathic corneal endothelial disorder.

(Item X5)
The medicament of any one of items X1 to X4, wherein the condition, disorder, or disease comprises Fuchs' endothelial corneal dystrophy.

(Item X6)
The medicament of any one of items X1 to X5, wherein the medicament prevents the progression of Fuchs' endothelial corneal dystrophy by suppressing a decrease in mitochondrial membrane potential of corneal endothelial cells in Fuchs' endothelial corneal dystrophy.

(Item X7)
The medicament of item X5, wherein the medicament is for use in treating or preventing a condition due to overproduction of extracellular matrix in Fuchs' endothelial corneal dystrophy.
(Item X8)
The medicament of item X7, wherein the condition comprises at least one selected from the group consisting of guttata on a corneal endothelial surface, turbid guttae of a Descemet's membrane, thickening of a Descemet's membrane, blurred vision, halo, glare, reduced vision, corneal haziness, leucoma, and abnormality in visual sense.
(Item X9)
A medicament for use in treating or preventing a corneal endothelial condition, disorder, or disease due to overexpression of extracellular matrix in corneal endothelial cells, comprising a caspase inhibitor.
(Item X10)
The medicament of item X9, wherein the condition, disorder, or disease is due to overexpression of fibronectin in corneal endothelial cells.
(Item X11)
The medicament of item X7 or X8, wherein the condition, disorder, or disease is selected from the group consisting of Fuchs' endothelial corneal dystrophy, guttae formation, thickening of a Descemet's membrane, thickening of a cornea, haziness, scar, corneal nebula, corneal macula, leucoma, photophobia, and blurred vision.
(Item X12)
The medicament of any one of items X9 to X11, wherein the condition, disorder, or disease comprises Fuchs' endothelial corneal dystrophy.
(Item X13)
The medicament of any one of items X9 to X12, wherein the condition, disorder, or disease comprises at least one selected from guttae formation and thickening of a Descemet's membrane in Fuchs' endothelial corneal dystrophy.
(Item X14)
A medicament for use in treating or preventing a corneal endothelial condition, disorder, or disease due to a TGF-@signal, a mitochondrial abnormality, and overexpression of extracellular matrix in corneal endothelial cells, comprising a caspase inhibitor.
(Item X15)
The medicament of item X14, wherein the condition, disorder, or disease is selected from the group consisting of Fuchs' endothelial corneal dystrophy, other endothelial corneal dystrophy, and a corneal endothelial disorder due to a drug, surgery, trauma, infection, or uveitis.
(Item X16)
The medicament of items X14 or X15, wherein the condition, disorder, or disease comprises Fuchs' endothelial corneal dystrophy.
(Item X17)
A composition for preservation of corneal endothelial cells or culturing after preservation, comprising a caspase inhibitor.
(Item X18)
The composition of item X17, wherein the preservation is cryopreservation.
(Item X19)
A composition for promoting the growth of corneal endothelial cells, comprising a caspase inhibitor.
(Item X20)
The composition of item X19, further comprising a p38 MAP kinase inhibitor.
(Item X21)
The medicament or composition of any one of items X1 to X20, wherein the caspase inhibitor is a caspase 3 inhibitor.
(Item X21A)
The medicament or composition of any one of items 1 to 21, wherein the caspase inhibitor is a pan caspase inhibitor.
(Item X22)
The medicament or composition of any one of items X1 to X21 and X21A, wherein the caspase inhibitor is selected from the group consisting of Z-VD-FMK, Z-VAD-FMK, emricasan, and nivocasan.
(Item X23)
The medicament or composition of item X22, wherein a concentration of the Z-VD-FMK is about 3 µM to about 100 µM.
(Item X24)
The medicament or composition of item X22, wherein a concentration of the Z-VAD-FMK is about 3 µM to about 30 µM.
(Item X25)
The medicament or composition of item X22, wherein a concentration of the emricasan is about 1 µM to about 100 µM.
(Item X26)
The medicament or composition of item X22, wherein a concentration of the nivocasan is about 30 µM to about 300 µM.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

The present invention provides a medicament that can treat or prevent a disorder or disease due to transforming growth factor-β (TGF-β) and/or a disease due to a mitochondrial abnormality in Fuchs' endothelial corneal dystrophy or the like. The present invention also provides a medicament that can treat or prevent a disease due to a corneal endothelial disorder due to overproduction of extracellular matrix (e.g., fibronectin) such as guttae, thickening of the Descemet's membrane, corneal haziness, leucoma or other conditions of clouding. The present invention further provides a composition for preserving corneal endothelial cells or a composition for promoting the growth of corneal endothelial cells.

BRIEF DESCRIPTION OF DRAWINGS

FIG. 12 shows the results of flow cytometry for measuring programmed cell death induced by TGF-β2. The results of flow cytometry are shown for each of the control group, TGF-β2 supplemented group, TGF-β2+SB431542 supplemented group (10 μM)), TGF-β2+Z-VD-FMK supplemented group (10 μM), and TGF-β2+emricasan supplemented group (10 μM).

FIG. 16 shows the measurements of cell viability rate from using various cryopreservation solutions. The left graph shows trypan blue negative cells (%). The right graph shows the cell viability rate (%) measured using CellTiter-Glo Luminescent Cell Viability Assay. Each graph shows, from the left, CELL BANKER PLUS, CELL BANKER 2, STEM-CELLBANKER, KM BANKER, CnT-CRYO, OptiMEM+10%FBS+10%DMSO, and non-cryopreserved control group.

FIG. 19 shows the effect of caspase inhibition of Z-VD-FMK on corneal endothelial cells after corneal endothelium cryopreservation. The image on the left shows corneal endothelial cells of the control supplemented with DMSO without adding a caspase inhibitor (KM BANKER was used as the medium), and the image on the right shows corneal endothelial cells when Z-VD-FMK was added.

DESCRIPTION OF EMBODIMENTS

Figure 1:
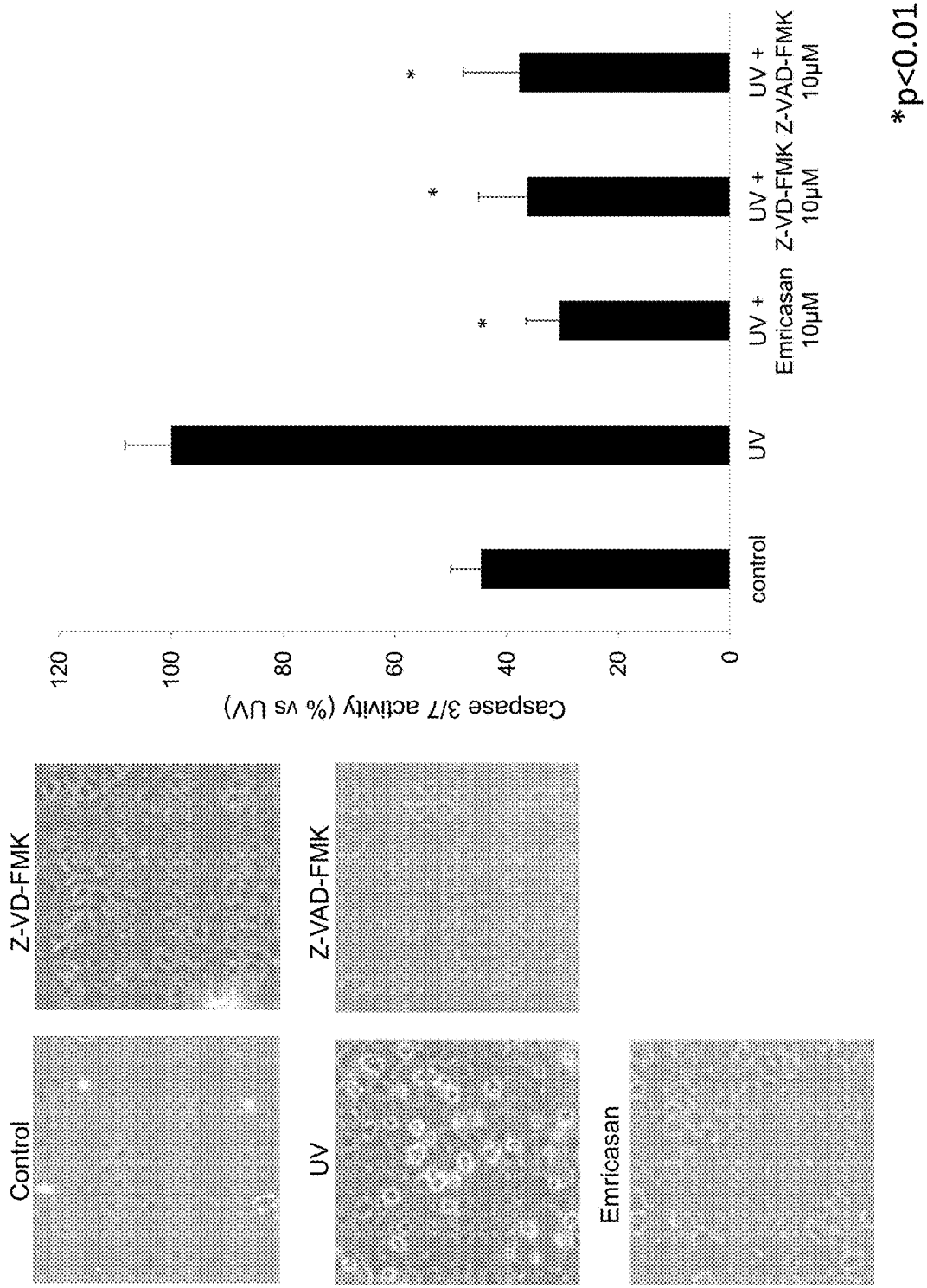
FIG. 1 shows microscope images of corneal endothelial cells after UV irradiation and a graph of caspase 3/7 activity. The left panel shows phase difference microscope images of the control group, UV irradiation group, UV irradiation+emricasan supplemented group, UV irradiation+Z-VD-FMK supplemented group, and UV irradiation+Z-VAD-FMK supplemented group. The right graph shows the caspase 3/7 activity vs UV irradiation group (%) in the vertical axis, and the control group, UV irradiation group, UV irradiation+emricasan supplemented group (10 µM), UV irradiation+Z-VD-FMK supplemented group (10 µM), and UV irradiation+Z-VAD-FMK supplemented group (10 µM). * indicates statistical significance (p<0.01).

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definitions

As used herein, "caspase" is a general term for endopeptidases that hydrolyze a peptide bond at the C-terminus side of aspartic acid, with cysteine as the center of activity. Caspases are known to have a function in processing cytokines (interleukin 1β and the like), involvement in execution of programmed cell death and inflammatory responses. All caspases are translated as an enzyme precursor. Caspases are activated from degradation by another caspase or themselves and function in a form of a cascade. Caspases are assigned a number in the order of discovery. Currently, caspase 1 to caspase 14 are known in mammals. About 10 types of caspases have been discovered in human cells. For example, caspase 1 has a function in inducing inflammation by processing cytokines, caspase 3 is directly involved in the execution of programmed cell death, and caspase 8 is positioned upstream the cascade and is responsible for signaling in programmed cell death.

As used herein, "caspase inhibitor" refers to any agent that inhibits signaling of any caspase. A caspase inhibitor is therefore a compound that can inhibit one or more of a caspase family. A caspase inhibitor is preferably water-soluble. This is because, unless a caspase inhibitor is water-soluble, it may be necessary to use a solvent that is not highly biocompatible. Water-solubility can be classified based on the definition of solubility in the pharmacopoeia. In other words, the amount of solvent required to dissolve 1 g or 1 mL of solute is defined as extremely readily dissolvable: less than 1 mL; readily dissolvable: 1 mL or greater and less than 10 mL; somewhat readily dissolvable: 10 mL or greater and less than 30 mL; somewhat difficult to dissolve: 30 mL or greater and less than 100 mL; difficult to dissolve: 100 mL or greater and less than 1000 mL; very difficult to dissolve: 1000 mL or greater and less than 10000 mL; and hardly dissolvable: 10000 mL or greater. Solubility is similarly assessed herein. Water solubility is understood to mean that a substance with any solubility can be used, as long as an effective amount thereof can be dissolved when water is used as a solvent. Such a water-soluble component is advantageously used as an eye drop.

The caspase inhibitors that can be used in the present invention are not particularly limited, as long as they are compounds having caspase inhibiting activity. Examples thereof include, but are not limited to, the compounds described in Japanese Laid-Open Publication No. 2012-036150, Japanese Laid-Open Publication No. 2007-308501, Japanese Laid-Open Publication No. 2005-089324, Japanese Laid-Open Publication No. 2002-338474, Japanese Laid-Open Publication No. 2001-302516, Japanese National Phase PCT Laid-open Publication No. 2009-542689, International Publication No. WO 2006/054757, and the like, as well as Z-VAD-FMK (pan caspase inhibitor), Z-VD-FMK (caspase 1, 3, 6, 7, 8, and 9 inhibitors that are substantially pan caspase inhibitors), Emricasan (all caspase inhibitor), Nivocasan (caspase 1, 3, 7, and 9 inhibitors that are substantially pan caspase inhibitors), Z-YVAD-FMK (caspase 1 inhibitor), Z-VDVAD-FMK (caspase 2 inhibitor), Z-DEVD-FMK (caspase 3 inhibitor), Z-LEVD-FMK (caspase 4 inhibitor), Z-WEHD-FMK (caspase 5 inhibitor), Z-VEID-FMK (caspase 6 inhibitor), Z-IETD-FMK (caspase 8 inhibitor), Z-LEHD-FMK (caspase 9 inhibitor), Z-AEVD-FMK (caspase 10 inhibitor), and Z-LEED-FMK (caspase 13 inhibitor).

Examples of preferred caspase inhibitors include, but are not limited to, emricasan. Examples of other preferred caspase inhibitors include, but are not limited to, Z-VAD-FMK, Z-VD-FMK, and nivocasan. A caspase inhibitor is preferably capable of inhibiting all caspases, but may be a selective caspase inhibitor. A selective caspase inhibitor refers to a caspase inhibitor that inhibits one or more caspases in a caspase family. Although not wishing to be bound by any theory, since caspase 3 is understood to be directly involved in programmed cell death, an inhibitor that inhibits caspase 3 is direct and effective, but an inhibitor that indirectly inhibits caspase 3 by inhibiting a caspase upstream (e.g., caspase 2, 8, 9, 10, or the like) in a caspase cascade may also be used. Alternatively, a caspase inhibitor may be an inhibitor that inhibits caspase 6 or caspase 7, which is considered factors executing programmed cell death just like caspase 3, or an inhibitor that indirectly inhibits caspase 6 or caspase 7 by inhibiting a caspase upstream in a caspase cascade. Preferably, a caspase inhibitor to be used is advantageously a "pan caspase inhibitor". Meanwhile, a caspase inhibitor that directly or indirectly inhibits caspase 8, which is not a direct factor for programmed cell death, but is considered to be a molecule that is important for signaling in programmed cell death, may be used.

Examples of other caspase inhibitors that can be used in the present invention include neutralizing antibodies of caspases, compounds inhibiting the activity of caspases, compounds inhibiting the transcription of a gene encoding a caspase (i.e., antisense nucleic acid, RNAi, and ribozyme) peptides, and compounds of plant components or the like. The concentration used is, for example, about 50 nmol/L to 100 µmol/L, and generally about 0.001 to 100 µmol/L, and preferably about 0.01 to 75 µmol/L, about 0.05 to 50 µmol/L, about 1 to 10 µmol/L, about 0.01 to 10 µmol/L, about 0.05 to 10 µmol/L, about 0.075 to 10 µmol/L, about 0.1 to 10 µmol/L, about 0.5 to 10 µmol/L, about 0.75 to 10 µmol/L, about 1.0 to 10 µmol/L, about 1.25 to 10 µmol/L, about 1.5 to 10 µmol/L, about 1.75 to 10 µmol/L, about 2.0 to 10 µmol/L, about 2.5 to 10 µmol/L, about 3.0 to 10 µmol/L, about 4.0 to 10 µmol/L, about 5.0 to 10 µmol/L, about 6.0 to 10 µmol/L, about 7.0 to 10 µmol/L, about 8.0 to 10 µmol/L, about 9.0 to 10 µmol/L, about 0.01 to 50 µmol/L, about 0.05 to 5.0 µmol/L, about 0.075 to 5.0 µmol/L, about 0.1 to 5.0 µmol/L, about 0.5 to 5.0 µmol/L, about 0.75 to 5.0 µmol/L, about 1.0 to 5.0 µmol/L, about 1.25 to 5.0 µmol/L, about 1.5 to 5.0 µmol/L, about 1.75 to 5.0 µmol/L, about 2.0 to 5.0 µmol/L, about 2.5 to 5.0 µmol/L, about 3.0 to 5.0 µmol/L, about 4.0 to 5.0 µmol/L, about 0.01 to 3.0 µmol/L, about 0.05 to 3.0 µmol/L, about 0.075 to 3.0 µmol/L, about 0.1 to 3.0 µmol/L, about 0.5 to 3.0 µmol/L, about 0.75 to 3.0 µmol/L, about 1.0 to 3.0 µmol/L, about 1.25 to 3.0 µmol/L, about 1.5 to 3.0 µmol/L, about 1.75 to 3.0 µmol/L, about 2.0 to 3.0 µmol/L, about 0.01 to 1.0 µmol/L, about 0.05 to 1.0 µmol/L, about 0.075 to 1.0 µmol/L, about 0.1 to 1.0 µmol/L, about 0.5 to 1.0 µmol/L, about 0.75 to 1.0 µmol/L, about 0.09 to 35 µmol/L, or about 0.09 to 3.2 µmol/L, and more preferably about 0.05 to 1.0 µmol/L, about 0.075 to 1.0 µmol/L, about 0.1 to 1.0 µmol/L, about 0.5 to 1.0 µmol/L, or about 0.75 to 1.0 µmol/L, but the concentration is not limited thereto.

Antisense nucleic acids used in the present invention may inhibit the expression and/or function of a gene (nucleic acid) encoding a member of a signaling pathway of a caspase or the like by any of the above-described actions. As one embodiment, designing an antisense sequence complementary to an untranslated region near the 5' end of mRNA of a gene encoding the aforementioned caspase or the like is considered effective for inhibiting translation of the gene. Further, a sequence that is complementary to an untranslated region of 3' or a coding region can also be used. In this manner, antisense nucleic acids utilized in the present invention include nucleic acids comprising an antisense sequence of a sequence of not only a translation region, but also an untranslated region of a gene encoding the aforementioned caspase or the like. An antisense nucleic acid to be used is linked downstream of a suitable promoter, and preferably a sequence comprising a transcription termination signal is linked to the 3' side. A nucleic acid prepared in this manner can be transformed into a desired animal (cell) by using a known method. A sequence of an antisense nucleic acid is preferably a sequence that is complementary to a gene encoding a caspase or the like of the animal (cell) to be transformed or a portion thereof. However, such a sequence does not need to be fully complementary, as long as gene expression can be effectively suppressed. A transcribed RNA preferably has complementarity that is 90% or greater, and most preferably 95% or greater, with respect to a transcript of a target gene. In order to effectively inhibit the expression of a target gene using an antisense nucleic acid, it is preferable that the length of the antisense nucleic acid is at least 12 bases and less than 25 bases. However, the antisense nucleic acid of the present invention is not necessarily limited to this length. For example, the length may be 11 bases or less, 100 bases or more, or 500 bases or more.

An antisense nucleic acid may be composed of only DNA, but may comprise a nucleic acid other than DNAs, such as a locked nucleic acid (LNA). As one embodiment, an antisense nucleic acid used in the present invention may be an LNA containing antisense nucleic acid comprising LNA at the 5' end or LNA at the 3' end. In an embodiment using an antisense nucleic acid in the present invention, the antisense sequence can be designed based on a nucleic acid sequence of a caspase or the like by using the method described in, for example, Hirashima and Inoue, Shin-seikagaku Jikkenn Kouza 2 [*New Biochemical Experiment Course* 2] Kakusan IV Idenshi no Fukusei to Hatsugen [*Duplication and Expression of Gene of Nucleic Acid IV*], Ed. by the Japanese Biochemical Society, Tokyo Kagaku Dojin, 1993, 319-347.

Expression of caspases or the like can also be inhibited by utilizing a ribozyme or DNA encoding a ribozyme. A ribozyme refers to an RNA molecule having catalytic activity. While there are ribozymes with various activities, a study focusing on especially ribozymes as an enzyme for cleaving an RNA made it possible to design a ribozyme that site-specifically cleaves an RNA. There are ribozymes with a size of 400 nucleotides or more as in group I intron ribozymes and M1 RNA contained in RNase P, but there are also those with an active domain of about 40 nucleotides called hammerhead or hair-pin ribozymes (Makoto Koizumi and Eiko Otsuka, Protein, Nucleic Acid and Enzyme, 1990, 35, 2191).

For example, a self-cleaving domain of a hammerhead ribozyme cleaves the 3' side of C15 of a sequence called G13U14C15. Base pair formation of U14 and A9 is considered important for the activity thereof. It is also demonstrated that cleavage can also be made at A15 or U15 instead of C15 (Koizumi, M. et al., FEBS Lett, 1988, 228, 228.) Restriction enzyme-like RNA-cleaving ribozymes that recognize the sequence UC, UU, or UA in the target RNAs can be created by designing their substrate-binding sites to be complementary to an RNA sequence near the target site (Koizumi, M. et al., FEBS Lett, 1988, 239, 285., Makoto Koizumi and Eiko Otsuka, Protein, Nucleic Acid and Enzyme, 1990, 35, 2191., Koizumi, M. et al., Nucl. Acids Res., 1989, 17, 7059.)

Hairpin ribozymes are also useful for the objective of the present invention. Such a ribozyme is found, for example, in the minus strand of a tobacco ringspot virus satellite RNA (Buzayan J M, Nature, 1986, 323, 349). It is demonstrated that target specific RNA-cleaving ribozymes can also be created from hairpin ribozymes (Kikuchi, Y. & Sasaki, N., Nucl. Acids Res, 1991, 19, 6751., Yo Kikuchi, Kagaku to Seibutsu [*Chemistry and Biology*], 1992, 30, 112). In this manner, expression of a gene encoding a caspase or the like can be inhibited by specifically cleaving a transcript of the gene by using a ribozyme.

Expression of an endogenous gene such as a caspase can also be suppressed by RNA interference (hereinafter, abbreviated as "RNAi") using a double-stranded RNA having a sequence that is identical or similar to a target gene sequence. RNAi is a methodology that is currently drawing attention, which can suppress the expression of a gene having a sequence that is homologous to a double strand RNA (dsRNA) when the dsRNA is incorporated directly into a cell. In mammalian cells, short stranded dsRNA (siRNA) can be used to induce RNAi. RNAi has many advantages over knockout mice, such as a stable effect, facilitated experiment, and low cost. siRNA is discussed in detail in other parts of the specification.

As used herein "siRNA" is an RNA molecule having a double-stranded RNA portion consisting of 15 to 40 bases, where siRNA has a function of cleaving mRNA of a target gene with a sequence complementary to an antisense strand of the siRNA to suppress the expression of the target gene. Specifically, the siRNA in the present invention is an RNA comprising a double-stranded RNA portion consisting of a sense RNA strand consisting of a sequence homologous to consecutive RNA sequences in mRNA of caspases or the like and an antisense RNA strand consisting of a sequence complementary to the sense RNA sequence. Design and manufacture of such siRNA and mutant siRNA discussed below are within the technical competence of those skilled in the art. Any consecutive RNA regions of mRNA which is a transcript of a sequence of caspase or the like can be appropriately selected to make double-stranded RNA corresponding to this region, which is within the ordinary procedure performed by those skilled in the art. Further, those skilled in the art can appropriately select an siRNA sequence having a stronger RNAi effect from mRNA sequences, which are transcripts of the sequence, by a known method. Further, if one of the strands is revealed, those skilled in the art can readily find the base sequence of the other stand (complementary strand). siRNA can be appropriately made by using a commercially available nucleic acid synthesizer. A common synthesis service can also be utilized for desired RNA synthesis.

In terms of bases, the length of a double-stranded RNA portion is 15 to 40 bases, preferably 15 to 30 bases, more preferably 15 to 25 bases, still more preferably 18 to 23 bases, and most preferably 19 to 21 bases. It is understood that the upper limits and the lower limits thereof are not limited to such specific limits, and may be of any combination of the mentioned limits. The end structure of a sense strand or antisense strand of siRNA is not particularly limited, and can be appropriately selected in accordance with the objective. For example, such an end structure may have a blunt end or a sticky end (overhang). A type where the 3' end protrudes out is preferred. siRNA having an overhang consisting of several bases, preferably 1 to 3 bases, and more preferably 2 bases at the 3' end of a sense RNA strand and antisense RNA strand is preferable for having a large effect of suppressing expression of a target gene in many cases. The type of bases of an overhang is not particularly limited, which may be either a base constituting an RNA or a base constituting a DNA. An example of a preferred overhang sequence includes dTdT at the 3' end (2 bp of deoxy T) and the like. Examples of preferable siRNA include, but are not limited to, all siRNAs with dTdT (2 bp of deoxy T) at the 3' end of the sense or antisense strands of the siRNA.

Furthermore, it is also possible to use siRNA in which one to several nucleotides are deleted, substituted, inserted and/or added at one or both of the sense strand and antisense strand of the siRNA described above. One to several bases as used herein is not particularly limited, but preferably refers to 1 to 4 bases, more preferably 1 to 3 bases, and most preferably 1 to 2 bases. Specific examples of such mutations include, but are not limited to, mutations resulting in 0 to 3 bases at the overhang portion, mutations that change the base sequence of the 3'-overhang portion to another base sequence, mutations in which the lengths of the above-described sense RNA strand and antisense RNA strand are different by 1 to 3 bases due to insertion, addition or deletion of bases, mutations substituting a base in the sense strand and/or antisense with another base, and the like. However, it is necessary that the sense strand and antisense strand can hybridize in such mutant siRNAs, and these mutant siRNAs have the ability to suppress gene expression that is equivalent to that of siRNAs without any mutations.

siRNA may also be a molecule with a structure in which one end is closed, such as a hairpin structure (Short Hairpin RNA; shRNA). A shRNA is an RNA comprising a sense strand RNA of a specific sequence of a target gene, an antisense strand RNA consisting of a sequence complementary to the sense strand sequence, and a linker sequence for connecting the two strands, wherein the sense strand portion hybridizes with the antisense strand portion to form a double-stranded RNA portion.

It is desirable for siRNA to not exhibit the so-called off-target effect in clinical use. An off-target effect refers to an action for suppressing the expression of another gene, besides the target gene, which is partially homologous to the siRNA used. In order to avoid an off-target effect, it is possible to confirm that a candidate siRNA does not have cross reactivity by using a DNA microarray or the like in advance. Further, it is possible to avoid an off-target effect by confirming whether there is a gene comprising a moiety that is highly homologous to a sequence of a candidate siRNA, other than a target gene, using a known database provided by the NCBI (National Center for Biotechnology Information) or the like.

In order to make the siRNA according to the present invention, a known method, such as a method using chemical synthesis or a method using a gene recombination technique, can be appropriately used. With a method using synthesis, a double-stranded RNA can be synthesized based on sequence information by using a common method. With a method using a gene recombination technique, a siRNA can be made by constructing an expression vector encoding a sense strand sequence or an antisense strand sequence and introducing the vector into a host cell, and then obtaining each of sense strand RNA and antisense strand RNA produced by transcription. It is also possible to make a desired double-stranded RNA by expressing an shRNA forming a hairpin structure, comprising a sense strand of a specific sequence of a target gene, an antisense strand consisting of a sequence complementary to the sense strand sequence, and a linker sequence for linking the two strands.

For a siRNA, all or part of the nucleic acid constituting the siRNA may be natural or a modified nucleic acid, as long as such a nucleic acid has activity to suppress the expression of a target gene.

The siRNA according to the present invention does not necessarily have to be a pair of double-stranded RNAs to a target sequence. It may be a mixture of a plurality of pairs (the "plurality" is not particularly limited, but preferably refers to a small number of about 2 to 5) of double-stranded RNAs to a region comprising a target sequence. In this regard, those skilled in the art can appropriately make an siRNA as a nucleic acid mixture corresponding to a target sequence by using a commercially available nucleic acid synthesizer and a DICER enzyme. A common synthesis service can also be utilized for desired RNA synthesis. It should be noted that the siRNA according to the present invention encompasses the so-called "cocktail siRNA". For the siRNA according to the present invention, not all the nucleotides have to be a ribonucleotide (RNA). In other words, in the present invention, one or a plurality of ribonucleotides constituting an siRNA may be a corresponding deoxyribonucleotide. This term "corresponding" refers to having the same base type (adenine, guanine, cytosine, thymine (uracil)) but a different sugar moiety structure. For example, a deoxyribonucleotide corresponding to a ribonucleotide having adenine refers to a deoxyribonucleotide having adenine.

Furthermore, a DNA (vector) which can express the above-described RNA according to the present invention is also encompassed as a preferred embodiment of a nucleic acid which can suppress the expression of a caspase or the like. For example, the DNA (vector) which can express the above-described double-stranded RNA according to the present invention is a DNA having a structure in which a DNA encoding one of the strands of the double-stranded RNA and a DNA encoding the other strand of the double-stranded RNA are linked with a promoter so that each of the DNAs can be expressed. The above-described DNA according to the present invention can be appropriately made by those skilled in the art by using a common genetic engineering technique. More specifically, the expression vector according to the present invention can be made by appropriately inserting a DNA encoding the RNA of interest into various known expression vectors.

In the present invention, a modified nucleic acid may be used as a nucleic acid for suppressing the expression of a target gene. A modified nucleic acid refers to a nucleic acid, which has a modification at a nucleoside (base moiety, sugar moiety) and/or an inter-nucleoside binding site and has a structure that is different from that of a naturally occurring nucleic acid. Examples of "modified nucleoside" constituting a modified nucleic acid include: abasic nucleosides; arabinonucleoside, 2'-deoxyuridine, α-deoxyribonucleoside, β-L-deoxyribonucleoside, and other sugar modification bearing nucleosides; peptide nucleic acids (PNA), phosphate group-binding peptide nucleic acids (PHONA), locked nucleic acids (LNA), morpholino nucleic acids and the like. The above sugar modification bearing nucleosides include 2'-O-methylribose, 2'-deoxy-2'-fluororibose, 3'-O-methylribose and other substituted pentose; 1',2'-deoxyribose; arabinose; substituted arabinose sugar; and nucleosides having a sugar modification of alpha-anomer and hexose. These nucleosides may also bear a base modification in which the base moiety is modified. Examples of such modified bases include pyrimidine such as 5-hydroxycytosine, 5-fluorouracil, and 4-thiouracil; purine such as 6-methyladenine and 6-thioguanosine; other heterocyclic bases and the like.

Examples of a "modified inter-nucleoside bond" which constitutes a modified nucleic acid include alkyl linker, glyceryl linker, amino linker, poly(ethylene glycol) bond, inter-methyl phosphonate nucleoside bond; and bonds between non-natural nucleosides such as methylphosphonothioate, phosphotriester, phosphothiotriester, phosphorothioate, phosphorodithioate, triester prodrug, sulfone, sulfonamide, sulfamate, formacetal, N-methylhydroxylamine, carbonate, carbamate, morpholino, boranophosphonate, and phosphoramidate.

The nucleic acid sequence comprised in the double-stranded siRNA according to the present invention includes siRNAs for a caspase, other caspase signaling members and the like.

It is also possible to introduce the nucleic acid or agent according to the present invention into a phospholipid endoplasmic reticulum such as a liposome and administer the endoplasmic reticulum. An endoplasmic reticulum in which an siRNA or shRNA is retained can be introduced into a predetermined cell using lipofection. The resulting cell is then systemically administered, such as intravenously, intra-arterially or the like. It can also be locally administered to a required site in an eye or the like. While an siRNA exhibits a very good specific, post-transcription suppressing effect in vitro, the siRNA is quickly degraded in vivo due to nuclease activity in the serum so that the duration thereof is limited. Therefore, there has been a need for the development of a better and more effective delivery system. As an example, Ochiya, T et al., Nature Med., 5: 707-710, 1999, Curr. Gene Ther., 1: 31-52, 2001 reports that a biocompatible material atelocollagen, when mixed with a nucleic acid to form a complex, is a carrier which has an action of protecting a nucleic acid from a degrading enzyme in a living organism and is extremely suitable as a carrier of an siRNA. While such a form can be used, the method for introducing a nucleic acid, therapeutic or prophylactic drug according to the present invention is not limited thereto. In this manner, due to the fast degradation by the action of a nuclease in the serum in a living organism, it becomes possible to achieve continuation of an effect for an extended period of time. For example, Takeshita F. PNAS, (2003) 102 (34) 12177-82, Minakuchi Y Nucleic Acids Research (2004) 32 (13) e109 report that atelocollagen derived from bovine skin forms a complex with a nucleic acid, which has action of protecting a nucleic acid from a degrading enzyme in a living organism and is extremely suitable as a carrier of an siRNA. Such a technique can be used.

As used herein, "iFECD" (immobilized Fuchs' endothelial corneal dystrophy) is an abbreviation for immobilized cells in Fuchs' endothelial corneal dystrophy.

As used herein, "HCEC" is an abbreviation for human corneal endothelial cells. In addition, "iHCEC" is an abbreviation for immobilized human corneal endothelial cells.

As used herein, "programmed cell death" refers to a phenomenon of cells spontaneously dying at a determined time or environment as if the death is pre-programmed. Programmed cell death is used in the meaning that includes, for example, "apoptosis".

As used herein, "transforming growth factor-β (also denoted with the abbreviation TGF-β)" is used in the same meaning as those used in the art. It is a homodimer multifunctional cytokine with a molecular weight of 25 kD exhibiting a variety of biological activity, such as being responsible for pathogenesis of various sclerotic diseases, rheumatoid arthritis, and proliferative vitreoretinopathy, being deeply involved in hair loss, suppressing the functioning of immunocompetent cells while suppressing overproduction of protease to prevent degradation of pulmonary tissue resulting in pulmonary emphysema, and suppressing cancer cell growth. "TGF-β signal" refers to a signal mediated by TGF-β, which is elicited by TGF-β. Examples of TGF-β signals include signals mediated by TGF-β2 in addition to signals mediated by TGF-β1, TGF-β3 or the like. In humans, TGF-β has three isoforms, TGF-β1 to β3, which have homology of about 70% and similar action. TGF-β is produced as an inactive latent form with a molecular weight of about 300 kD which is unable to bind to a receptor. The action thereof is exerted by being activated on a target cell surface or the surroundings thereof to become an active form that can bind to a receptor.

Although not wishing to be bound by any theory, the action of TGF-β in a target cell is understood to be transmitted by a phosphorylation pathway of a series of proteins responsible for transmitting information called Smad. First, when activated TGF-β binds to a TGF-β type II receptor on a target cell surface, a receptor complex consisting of two molecules of type II receptors and two molecules of TGF-β type I receptors is formed, and the type II receptors phosphorylate the type I receptors. It is understood that when the phosphorylated type I receptors phosphorylate Smad2 or Smad3, the phosphorylated Smad2 or Smad3 forms a complex with Smad4, where the complex migrates to a nucleus and binds to a target sequence called CAGA box that is present in a target gene promotor region to induce transcription and expression of a target gene with a coactivator.

A transforming growth factor-β (TGF-β) signaling pathway can modulate many cellular activities, such as cell growth and differentiation, growth arrest, programmed cell death, and epithelial mesenchymal transition (EMT), by modulating the target gene. Members of the TGF-β family including TGF-β itself (e.g., TGF-β1, TGF-β2, and TGF-β3), activin, and bone morphogenetic proteins (BMP) are potent modulators of cell growth, differentiation, migration, programmed cell death, and the like.

TGF-β is a protein of about 24 Kd produced by many cells including B lymphocytes, T lymphocytes, and activated macrophages and by many other cell types. Effects of TGF-β on the immune system include IL-2 receptor induction, inhibition of IL-1 induced thymocyte growth, and blocking of IFN-γ induced macrophage activation. TGF-β is considered to be involved in various pathological conditions (Border et al. (1992) J. Clin. Invest. 90:1) and is thoroughly proven to function as either a tumor suppressing substance or a tumor promotor.

Signaling of TGF-β is mediated by two serine/threonine kinase cell surface receptors TGF-βRII and ALK5. TGF-β signaling is initiated by ligand induced receptor dimerization enabling TGF-βRII to phosphorylate an ALK5 receptor. The phosphorylation activates ALK5 kinase activity, and the activated ALK5 then phosphorylates a downstream effector Smad protein (vertebrate homologue of MAD or "Mothers against DPP (decapentaplegic)" protein), Smad2 or Smad 3. A p-Smad2/3 complex with Smad4 enters a nucleus and activates transcription of a target gene.

Smad3 is a member of the R-Smad (receptor-activated Smad) subgroup of Smad and a direct mediator of transcription activation by a TGF-β receptor. A TGF-β stimulation results in phosphorylation and activation of Smad2 and Smad3, which form a complex with Smad4 ("common Smad" or "co-Smad" in vertebrates). This accumulates with the nucleus and modulates transcription of a target gene. R-Smad is localized in a cytoplasm and forms a complex with co-Smad in ligand induced phosphorylation by a TGF-β receptor, migrates to the nucleus, where it modulates gene expression associated with a cooperative transcription factor and chromatin. Smad6 and Smad7 are inhibitory Smad ("I-Smad"), i.e., they are transcriptionally induced by TGF-β and function as a TGF-β signaling inhibitor (Feng et al. (2005) Annu. Rev. Cell. Dev. Biol. 21: 659). Smad6/7 obstruct receptor-mediated activation of R-Smad to exert an inhibitory effect thereof; and they are associated with a type I receptor, which competitively obstructs mobilization and phosphorylation of R-Smad. Smad6 and Smad7 are known to replenish E3 ubiquitin ligase, which induces ubiquitination and degradation of Smad6/7 interacting proteins.

TGF-β signaling pathways also have other pathways using transmission by BMP-7 or the like, which go through ALK-1/2/3/6 to express a function via Smad1/5/8. For TGF-β signaling pathways, see J. Massagu'e, Annu. Rev. Biochem. 1998. 67: 753-91; Vilar J M G, Jansen R, Sander C (2006) PLoS Comput Biol 2 (1): e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152: 159-166 and the like.

As used herein, "corneal endothelial condition, disorder, or disease due to transforming growth factor-β (TGF-β)" refers to any corneal endothelial condition, disorder, or disease induced by TGF-β in corneal endothelial cells. In the present invention, exposure of corneal endothelial cells such as model cells of Fuchs' endothelial corneal dystrophy (e.g., iFECD) to TGF-β2 surprisingly resulted in various disorders (e.g., programmed cell death). This is a phenomenon that had not been well understood conventionally. The inventors, after further analysis of the corneal endothelial condition, disorder, or disease due to a TGF-β signal, unexpectedly discovered that this disorder can be suppressed with a caspase inhibitor. A corneal endothelial condition, disorder, or disease due to a TGF-β signal is associated with a different signaling pathway of caspases, and the caspase inhibitor that was used did not suppress the signaling pathway of TGF-β. Thus, a pathway of manifestation of disease/disorder and a form of therapy and prophylaxis thereof, which were previous unresolved, were able to be discovered. Thus, the present invention can be positioned as an invention providing a novel therapeutic/prophylactic technique for corneal endothelia. Examples of corneal endothelial conditions, disorders, or diseases due to a TGF-β signal include, but are not limited to, Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder and the like in which TGF-β expression is observed. Since the disorder discovered in the present invention or a disorder associated therewith is considered expressed or advanced especially in corneal endothelial cells or corneal endothelial tissue with higher than normal TGF-β2 expression, any corneal endothelial condition, disorder, or disease in which such corneal endothelial cells or corneal endothelial tissue are observed are especially intended as the target of the present invention.

As used herein, "corneal endothelial condition, disorder, or disease due to a mitochondrial abnormality" refers to a corneal endothelial condition, disorder, or disease due to a mitochondrial abnormality. Examples of corneal endothelial conditions, disorders, or diseases due to a mitochondrial abnormality include, but are not limited to, any Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder in which a mitochondrial abnormality is observed.

As used herein, "overexpression of extracellular matrix in corneal endothelial cells" refers to expression of extracellular matrix at an abnormal level compared to extracellular matrix expression levels in normal corneal endothelial cells. "Expression of extracellular matrix at an abnormal level" refers to production of extracellular matrix proteins such as fibronectin at an amount greater than the amount produced in extracellular matrix in a normal form. The production status includes no stimulation, as well as increased amount of expression due to a response to transforming growth factor (TGF) β as needed. For example, this can be about 1.1 fold or greater, about 1.2 fold or greater, about 1.3 fold or greater, about 1.4 fold or greater, about 1.5 fold or greater, about 1.6 fold or greater, about 1.7 fold or greater, about 1.8 fold or greater, about 1.9 fold or greater, or about 2.0 fold or greater with respect to the amount of extracellular matrix under normal circumstances for human corneal endothelial cells. The difference relative to normal is preferably, but not necessarily, statistically significant. It is sufficient that the difference is a medically significant difference.

As used herein, "corneal endothelial disorder due to overproduction of extracellular matrix (ECM)" or a "condition" thereof is mainly a disorder associated with thickening, deposition, clouding due to extracellular matrix or the like, or a condition thereof, which results in guttata on the corneal endothelium surface, thickening of the Descemet's membrane such as turbid guttae of the Descemet's membrane, or the like, and is associated with a condition that causes reduced vision. In corneal endothelial disorders such as Fuchs' corneal dystrophy, overproduction of extracellular matrix worsens the vision or visual sense even without a reduction in cell count, unlike exacerbation in a condition due to death (especially apoptosis) of corneal endothelial cells. Thus, even if cell death can be suppressed, this needs to be addressed. In the present invention, it was found that a caspase inhibitor can suppress the cause of corneal endothelial disorders due to "haziness" or "deposition". This supports the present invention to be capable of improving, treating, or preventing a "corneal endothelial disorder due to overproduction of extracellular matrix (ECM)" and condition associated therewith. "Corneal endothelial disorder due to overproduction of extracellular matrix (ECM)" and "condition" thereof include, but are not limited to, haziness, scar, corneal nebula, corneal macula, leucoma, and the like.

In a preferred embodiment, the conditions, disorders, or diseases targeted by the present invention are disorders related to Fuchs' endothelial corneal dystrophy. It is demonstrated that TGF-β induction in corneal endothelial cells is involved in Fuchs' endothelial corneal dystrophy. It is also demonstrated that TGF-β induction may be involved in cell lost in FECDs. Therefore, inhibition of a TGF-β signaling pathway is naturally expected to be an effective therapy for FECDs. However, the inventors unexpectedly found that a caspase inhibitor can suppress a disorder due to a TGF-β signal.

Since the medicament of the present invention can treat cell damage or the like that is induced by TGF-β2, which can be one of the important causes of abnormalities or disorders in Fuchs' endothelial corneal dystrophy, the medicament is understood to be useful in treating or preventing Fuchs' endothelial corneal dystrophy. In particular, the present invention was able to suppress cell damage or programmed cell death induced by TGF-β2 in a Fuchs' endothelial corneal dystrophy model in the Examples, so that the present invention can be considered usable in therapy of patients with a severe TGF-β2 associated disease in a Fuchs' endothelial corneal dystrophy model. The medicament of the present invention can also, unexpectedly, suppress overexpression of extracellular matrix (ECM), so that the medicament can treat or prevent a disorder or the like in corneal endothelia such as ECM deposition in the Descemet's membrane. Therefore, the present invention can treat or prevent damage to corneal endothelial cells in Fuchs' endothelial corneal dystrophy, decreased corneal endothelial density, guttae formation, thickening of the Descemet's membrane, thickening of a cornea, corneal epithelial disorder, haziness, scar, haziness in corneal stroma, photophobia, blurred vision, visual impairment, ophthalmalgia, epiphora, hyperemia, pain, bullous keratopathy, eye discomfort, diminished contrast, halo, glare, edema of the corneal stroma, and the like.

In a specific embodiment, the present invention can also suppress mitochondrial abnormalities such as a decrease in mitochondrial membrane potential, a morphological abnormality of mitochondria, a decrease in mitochondrial biosynthesis, and the like.

(General Techniques)

Molecular biological methodology, biochemical methodology, microbiological methodology used herein are well known and conventionally used in the art, which are described for example in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [*Experimental Medicine, Supplemental Volume*], Idenshi Donyu & Hatsugen Kaiseki Jikken Ho [*Experimental Methods for Transgenesis & Expression Analysis*], Yodosha, 1997, or the like. The reports by Nancy Joyce et al {Joyce, 2004 #161} and {Joyce, 2003 #7} are well known for corneal endothelial cells. However, as discussed above, long-term culture or subculture results in fibroblast-like transformation, and research for an effective culturing method are currently ongoing. Relevant portions thereof (which may be the entire document) are incorporated herein by reference.

Disclosure of Preferred Embodiments

The preferred embodiments of the present invention are described hereinafter. It is understood that the embodiments are exemplification of the present invention, so that the scope of the present invention is not limited to such preferred embodiments. It should be understood that those skilled in the art can refer to the following preferred embodiments to readily make modifications or changes within the scope of the present invention. Any of these embodiments of the present invention can be appropriately combined by those skilled in the art.

<Medicament>

In one aspect, the present invention provides a medicament for use in treating or preventing a corneal endothelial condition, disorder, or disease due to a transforming growth factor-β (TGF-β) signal in corneal endothelial cells, comprising a caspase inhibitor.

In another aspect, the present invention provides a medicament for use in treating or preventing a corneal endothelial condition, disorder, or disease due to a mitochondrial abnormality in corneal endothelial cells, comprising a caspase inhibitor.

In still another aspect, the present invention provides a medicament for use in treating or preventing a corneal endothelial condition, disorder, or disease due to a transforming growth factor-β (TGF-β) signal and a mitochondrial abnormality in corneal endothelial cells, comprising a caspase inhibitor.

While a caspase is understood to be involved in a variety of signaling as well as inflammation, not all of the mechanisms thereof are elucidated in corneal endothelia, such that it was unexpected that a caspase is effective in healing or preventing a corneal endothelial disorder due to a TGF-β signal, mitochondrial disorder, or both.

In one embodiment, a corneal endothelial condition, disorder, or disease due to transforming growth factor-β (TGF-β) in corneal endothelial cells is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder.

In one embodiment, a corneal endothelial condition, disorder, or disease due to a mitochondrial abnormality in corneal endothelial cells is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder. In a preferred embodiment, a corneal endothelial condition, disorder, or disease due to a TGF-β signal is a corneal endothelial condition, disorder, or disease due to TGF-β2.

In one embodiment, examples of mitochondrial abnormalities include, but are not limited to, a decrease in mitochondrial membrane potential, a morphological abnormality of mitochondria, mitochondrial biosynthesis, and the like.

In still another preferred embodiment, the present invention provides a medicament having an action and effect for treating or preventing a condition due to overproduction of extracellular matrix in Fuchs' endothelial corneal dystrophy for use in treating or preventing such a condition, or a method of treating or preventing such a condition. Examples of such a condition include guttata on a corneal endothelial surface, turbid guttae of a Descemet's membrane, thickening of the Descemet's membrane, blurred vision, halo, glare, reduced vision, corneal haziness, leucoma, abnormality in visual sense, and the like. Conditions due to overproduction of extracellular matrix are further discussed below.

In still another aspect, the present invention provides a medicament for use in treating or preventing a corneal endothelial condition, disorder, or disease due to overexpression of extracellular matrix in corneal endothelial cells, comprising a caspase inhibitor. As discussed above, a caspase inhibitor can treat or prevent a corneal endothelial disorder or the like due to a TGF-β signal or a mitochondrial abnormality, but it was surprising that a caspase inhibitor can also suppress overexpression of extracellular matrix in corneal endothelial cells. This suggests that a caspase inhibitor can simultaneously treat corneal endothelial disorders due to a TGF-β signal, mitochondrial abnormality and overexpression of extracellular matrix in corneal endothelial cells. In particular, Fuchs' endothelial corneal dystrophy is a disease in which the density of corneal endothelial cells significantly decreases due to a TGF-β signal and a mitochondrial abnormality, and extracellular matrix is deposited in the Descemet's membrane, resulting in corneal guttae and thickening of the Descemet's membrane. For this reason, suppression of the overexpression of extracellular matrix means that therapy and prophylaxis of Fuchs' endothelial corneal dystrophy can be significantly improved, and is capable of complete healing in some cases. It is also possible to improve, treat, or prevent corneal guttae and thickening of the Descemet's membrane, as well as other conditions associated with haziness or deposition (irreversible haziness in corneal stroma due to protracted corneal edema or the like) that can occur due to overproduction of extracellular matrix in corneal endothelial disorders such as Fuchs' endothelial corneal dystrophy.

In one embodiment, a corneal endothelial condition, disorder, or disease due to overexpression of extracellular matrix in corneal endothelial cells can be due to overexpression of fibronectin in corneal endothelial cells.

In one embodiment, a corneal endothelial condition, disorder, or disease due to overexpression of extracellular matrix in corneal endothelial cells is selected from the group consisting of Fuchs' endothelial corneal dystrophy, guttae formation, thickening of the Descemet's membrane, thickening of a cornea, haziness, scar, haziness in corneal stroma, corneal epithelial edema, corneal epithelial disorder, photophobia, and blurred vision.

In another aspect, the present invention provides a medicament for use in treating or preventing a corneal endothelial condition, disorder, or disease due to a TGF-β signal, a mitochondrial abnormality, and overexpression of extracellular matrix in corneal endothelial cells, comprising a caspase inhibitor. A caspase inhibitor can simultaneously treat or prevent corneal endothelial disorders due to a TGF-β signal, mitochondrial abnormality and overexpression of extracellular matrix in corneal endothelial cells.

In one embodiment, a corneal endothelial condition, disorder, or disease due to a TGF-β signal, a mitochondrial abnormality, and overexpression of extracellular matrix in corneal endothelial cells is selected from the group consisting of Fuchs' endothelial corneal dystrophy, other endothelial corneal dystrophy, and a corneal endothelial disorder due to a drug, surgery, trauma, infection, uveitis, or the like.

In one embodiment, a corneal endothelial condition, disorder, or disease due to a TGF-β signal, a mitochondrial abnormality, and overexpression of extracellular matrix in corneal endothelial cells comprises Fuchs' endothelial corneal dystrophy. Fuchs' endothelial corneal dystrophy is a disease in which the density of corneal endothelial cells significantly decreases due to a TGF-β signal and a mitochondrial abnormality, and extracellular matrix is deposited in the Descemet's membrane, resulting in a disorder such as corneal guttae and thickening of the Descemet's membrane. For this reason, suppression of the overexpression of extracellular matrix means that therapy can significantly improve Fuchs' endothelial corneal dystrophy, and complete healing in some cases.

In one embodiment, examples of utilization methods of the present invention include, but are not limited to, eye drops, as well as administration methods such as injection into the anterior chamber, impregnation into a controlled-release agent, subconjunctival injection, and systemic administration (oral administration and intravenous injection).

In one embodiment, the caspase inhibitor used in the present invention can be any type of caspase inhibitor, as long as it is effective in treating or preventing a given corneal endothelial condition, disorder, or disease due to a TGF-β signal or mitochondria, but is preferably an inhibitor that inhibits caspase 3, and more preferably a pan caspase inhibitor. Specific caspase inhibitors include at least one selected from the group consisting of Z-VAD-FMK, Z-VD-FMK, Emricasan, Nivocasan, Z-YVAD-FMK, Z-VDVAD-FMK, Z-DEVD-FMK, Z-LEVD-FMK, Z-WEHD-FMK, Z-VEID-FMK, Z-IETD-FMK, Z-LEHD-FMK, Z-AEVD-FMK, and Z-LEED-FMK.

The above caspase inhibitors may be used alone or in combination in the medicament of the present invention. The concentration of a caspase inhibitor used in the present invention is generally about 0.1 to 300 µM (µmol/L), preferably about 1 to 150 µM, and more preferably about 3 to 30 µM. When two or more types of caspase inhibitors are used in combination, the concentration can be appropriately changed. Examples of other concentration ranges include, but are not limited to, generally about 0.001 to 300 µM, about 0.01 to 150 µM, about 0.001 to 100 µM, about 0.01 to 75 µM, about 0.05 to 50 µM, about 1 to 10 µM, about 0.01 to 10 µM, about 0.05 to 10 µM, about 0.075 to 10 µM, about 0.1 to 10 µM, about 0.5 to 10 µM, about 0.75 to 10 µM, about 1.0 to 10 µM, about 1.25 to 10 µM, about 1.5 to 10 µM, about 1.75 to 10 µM, about 2.0 to 10 µM, about 2.5 to 10 µM, about 3.0 to 10 µM, about 4.0 to 10 µM, about 5.0 to 10 µM, about 6.0 to 10 µM, about 7.0 to 10 µM, about 8.0 to 10 µM, about 9.0 to 10 µM, about 0.01 to 50 µM, about 0.05 to 5.0 µM, about 0.075 to 5.0 µM, about 0.1 to 5.0 µM, about 0.5 to 5.0 µM, about 0.75- to 5.0 µM, about 1.0 to 5.0 µM, about 1.25 to 5.0 µM, about 1.5 to 5.0 µM, about 1.75 to 5.0 µM, about 2.0 to 5.0 µM, about 2.5 to 5.0 µM, about 3.0 to 5.0 µM, about 4.0 to 5.0 µM, about 0.01 to 3.0 µM, about 0.05 to 3.0 µM, about 0.075 to 3.0 µM, about 0.1 to 3.0 µM, about 0.5 to 3.0 µM, about 0.75 to 3.0 µM, about 1.0 to 3.0 µM, about 1.25 to 3.0 µM, about 1.5 to 3.0 µM, about 1.75 to 3.0 µM, about 2.0 to 3.0 µM, about 0.01 to 1.0 µM, about 0.05 to 1.0 µM, about 0.075 to 1.0 µM, about 0.1 to 1.0 µM, about 0.5 to 1.0 µM, about 0.75 to 1.0 µM, about 0.09 to 35 µM, about 0.09 to 3.2 µM, about 0.05 to 1.0 µM, about 0.075 to 1.0 µM, about 0.1 to 1.0 µM, about 0.5 to 1.0 µM, or about 0.75 to 1.0 µM.

In a preferred embodiment, a caspase inhibitor is selected from the group consisting of, for example, N-(benzyloxycarbonyl)-L-valyl-DL-aspartyl-fluoromethylketone (Z-VD-FMK), {benzyloxycarbonyl-L-valyl-L-alanyl-[(2s)-2-amino-3-(methoxycarbonyl)propionyl]}fluoromethane (Z-VAD-FMK), 3-[2-[(2-tert-butyl-phenylaminooxalyl)-amino]-propionylamino]-4-oxo-5-(2,3,5,6-tetrafluoro-phenoxy)-pentanoic acid (emricasan), (R)—N-((2S,3S)-2-(fluoromethyl)-2-hydroxy-5-oxotetrahydrofuran-3-yl)-5-isopropyl-1-3-(isoquinoline-1-yl)-4,5-dihydroisoxazole-5-carboxamide (nivocasan), and salts thereof.

In another embodiment, a caspase inhibitor is Z-VD-FMK. The concentration of Z-VD-FMK used is generally about 1 µM to about 150 µM, preferably about 3 µM to about 100 µM, and more preferably about 10 µM to about 50 µM.

In another embodiment, a caspase inhibitor is Z-VAD-FMK. The concentration of Z-VAD-FMK used is generally about 1 µM to about 100 µM, preferably about 3 µM to about 30 µM, and more preferably about 10 µM.

In another embodiment, a caspase inhibitor is emricasan. The concentration of emricasan used is generally about 0.3 µM to about 150 µM, preferably about 1 µM to about 100 µM, and more preferably about 10 µM.

In another embodiment, a caspase inhibitor is nivocasan. The concentration of nivocasan used is generally about 1 µM to about 300 µM, preferably about 30 µM to about 300 µM, and more preferably about 100 µM.

In a preferred embodiment, emricasan is used. Although not wishing to be bound by any theory, this is because it was found that treatment with emricasan exhibited a significantly better therapeutic result compared to other caspase inhibitors, and results of healing especially a corneal endothelial disease or disorder associated with transforming growth factor-β2 (TGF-β2) such as Fuchs' endothelial dystrophy, or corneal endothelial disease or disorder associated with a mitochondrial abnormality are significantly improved.

In one embodiment, a therapeutic or prophylactic medicament of the present invention can be targeted for any animal with a corneal endothelium, such as mammals. Such a medicament is preferably intended for treating or preventing a primate corneal endothelium. The subject of therapy or prophylaxis is preferably a human corneal endothelium.

In another aspect, the present invention provides a method of treating or preventing a corneal endothelial condition, disorder, or disease due to at least one of transforming growth factor-β (TGF-β) and a mitochondrial abnormality in corneal endothelial cells, comprising administering an effective dose of a caspase inhibitor to a subject in need thereof.

As used herein, a "subject" refers to a target of administration (transplant) of a therapeutic or prophylactic medicament or method of the present invention. Examples of subjects include mammals (e.g., human, mouse, rat, hamster, rabbit, cat, dog, cow, horse, sheep, monkey and the like), but primates are preferable and humans are especially preferable.

The effective dose of the medicament of the present invention, which is effective in treating a specific disease, disorder, or condition, can vary depending on the properties of a disorder or condition, but the effective dose can be determined by those skilled in the art with standard clinical techniques based on the descriptions in the present specification. It is also possible to use an in vitro assay to assist in identifying the optimal range of dosage as needed. Since an accurate dose to be used in a formulation can vary depending on the route of administration and the severity of a disease or disorder, the dose should be determined in accordance with the judgment of a physician and the condition of each patient. However, the dosage, while not particularly limited, may be, for example, 0.001, 1, 5, 10, 15, 100, or 1000 mg/kg body weight or a value between any two such values per dose. The interval of administration, while not particularly limited, may be for example one or two doses for every 1, 7, 14, 21, or 28 days, or one or two doses for a number of days between any two such values. The dosage, number of doses, administration interval, and administration method may be appropriately selected depending on the age or body weight of a patient, condition, dosage form, target organ, or the like. For example, the present invention can be used as an eye drop. The medicament of the present invention can also be injected into the anterior chamber. A therapeutic drug preferably comprises a therapeutically effective dose or an effective dose of active ingredients at which a desired action is exerted. It may be determined that there is a therapeutic effect when a therapeutic marker significantly decreases after administration. The effective dose can be estimated from a dose-response curve obtained from an in vitro or animal model testing system.

<Composition for Preservation>

In another aspect, the present invention provides a composition for preservation of corneal endothelial cells, comprising a caspase inhibitor. In a preferred embodiment, preservation is cryopreservation. It is understood that the caspase inhibitor used in the present invention can have any form explained herein, such as an embodiment that is suitable as a composition for preservation among the embodiments explained as a medicament.

As used herein, a "composition for preservation" is a composition for preserving a cornea fragment extracted from a donor until the fragment is transplanted into a recipient, or for preserving corneal endothelial cells before being grown or after being grown.

In one embodiment, the composition for preservation of the present invention can be prepared by adding a caspase inhibitor of the present invention to a conventionally used preservative or preservation solution. Examples of such a cornea preservation solution include preservation solutions that are commonly used for corneal transplant (sclerocornea fragment preservation solution (Optisol GS®) or eye ball preservation solution for corneal transplant (EPII®)), saline, phosphate-buffered saline (PBS) and the like.

The composition for preservation of the present invention is used for preserving a cornea that is used in organ transplant or the like. The composition for preservation of the present invention is also used as a preservation solution for cryopreserving corneal endothelial cells or as a component thereof.

In another embodiment of the composition for preservation of the present invention used for cryopreservation, an existing cryopreservation solution can be used by adding a composition for preservation comprising a caspase inhibitor of the present invention. Examples of a cryopreservation solution include, but are not limited to, CELLBANKER® series provided by Takara Bio (CELL BANKER PLUS (catalog number: CB021), CELL BANKER 2 (catalog number: CB031), STEM-CELLBANKER (catalog number: CB043) and the like), KM BANKER (Kohjin Bio, catalog number: KOJ-16092005), and Freezing Medium, Animal Component Free, CRYO Defined (also denoted as Cnt-CRYO) (CELLNTEC, catalog number: CnT-CRYO-50). In yet another embodiment, the cryopreservation solution used may be KM BANKER. It is understood that those skilled in the art can use a suitable modified cryopreservation solution by appropriately changing a constituent component of the above cryopreservation solution or by adding an additional constituent component. For example, glycerol, dimethyl sulfoxide, propylene glycol, acetamide, or the like may be further added to the preservation solution of the present invention for cryopreservation.

<Growth Promoting Composition>

In another aspect, the present invention provides a composition for promoting the growth of corneal endothelial cells. It is understood that the caspase inhibitor used in the present invention can have any form explained herein such as an embodiment that is suitable as a composition for preservation among the embodiments explained as a medicament.

In one embodiment, the growth promoting composition of the present invention can be prepared by adding the caspase inhibitor of the present invention to a conventionally used medium. The culture component that can be used in the present invention may be any component that can be used in culture of corneal endothelia. This may be a medium component that is conventionally sold and used, or a component separately developed for corneal endothelia. Examples of such medium components include, but are not limited to, OptiMEM, DMEM, M199, MEM, and the like (which are available form THERMO-FISCHER-INVITROGEN).

As explained in the Examples, it was found that culture of corneal endothelial cells is promoted when the cells are cultured with a cryopreservation solution supplemented with the growth promoting composition comprising a caspase inhibitor of the present invention as a medium component. Therefore, a cryopreservation solution can be used as a medium component used in the composition for promoting growth of corneal endothelial cells of the present invention. Examples of cryopreservation solutions include, but are not limited to, CELLBANKER® series provided by Takara Bio (CELL BANKER PLUS (catalog number: CB021), CELL BANKER 2 (catalog number: CB031), STEM-CELL-BANKER (catalog number: CB043) and the like), KM BANKER (Kohjin Bio, catalog number: KOJ-16092005), and Freezing Medium, Animal Component Free, CRYO Defined (CnT-CRYO) (CELLNTEC, catalog number: CnT-CRYO-50). In another embodiment, the cryopreservation solution used is preferably, but not limited to, KM BANKER.

In another embodiment, the composition for promoting the growth of corneal endothelial cells of the present invention can further comprise a p38 MAP kinase inhibitor. A "p38 MAP kinase inhibitor (also referred to as "p38 MAPK inhibitor")" refers to any agent that inhibits signaling of a MAP kinase associated with p38. Examples thereof include, but are not limited to, 4-(4-fluorophenyl)-2-(4-methylsulfinylphenyl)-5-(4-pyridyl)-1H-imidazole (SB-203580), 1-(carbamoyl-6-(2,4-difluorophenyl)pyridin-2-yl)-1-(2,6-difluorophenyl)urea (VX-702), and 3-[3-bromo-4-[(2,4-difluorophenyl)methoxy]-6-methyl-2-oxopyridin-1-yl]-N,4-dimethylbenzamide (PH797804). The concentration of a contained p38 MAP kinase inhibitor can be appropriately selected by those skilled in the art, for example, about 0.1 to 100 μM (μmol/L), preferably about 0.1 to 30 μM, and more preferably about 1 to 10 μM. Examples of other concentration ranges include, but are not limited to, generally about 0.001 to 100 μM, preferably, about 0.01 to 75 μM, about 0.05 to 50 μM, about 1 to 10 μM, about 0.01 to 10 μM, about 0.05 to 10 μM, about 0.075 to 10 μM, about 0.1 to 10 μM, about 0.5 to 10 μM, about 0.75 to 10 μM, about 1.0 to 10 μM, about 1.25 to 10 μM, about 1.5 to 10 μM, about 1.75 to 10 μM, about 2.0 to 10 μM, about 2.5 to 10 μM, about 3.0 to 10 μM, about 4.0 to 10 μM, about 5.0 to 10 μM, about 6.0 to 10 μM, about 7.0 to 10 μM, about 8.0 to 10 μM, about 9.0 to 10 μM, about 0.01 to 50 μM, about 0.05 to 5.0 μM, about 0.075 to 5.0 μM, about 0.1 to 5.0 μM, about 0.5 to 5.0 μM, about 0.75 to 5.0 μM, about 1.0 to 5.0 μM, about 1.25 to 5.0 μM, about 1.5 to 5.0 μM, about 1.75 to 5.0 μM, about 2.0 to 5.0 μM, about 2.5 to 5.0 μM, about 3.0 to 5.0 μM, about 4.0 to 5.0 μM, about 0.01 to 3.0 μM, about 0.05 to 3.0 μM, about 0.075 to 3.0 μM, about 0.1 to 3.0 μM, about 0.5 to 3.0 μM, about 0.75 to 3.0 μM, about 1.0 to 3.0 μM, about 1.25 to 3.0 μM, about 1.5 to 3.0 μM, about 1.75 to 3.0 μM, about 2.0 to 3.0 μM, about 0.01 to 1.0 μM, about 0.05 to 1.0 μM, about 0.075 to 1.0 μM, about 0.1 to 1.0 μM, about 0.5 to 1.0 μM, about 0.75 to 1.0 μM, about 0.09 to 35 μM, about 0.09 to 3.2 μM, and more preferably, about 0.05 to 1.0 μM, about 0.075 to 1.0 μM, about 0.1 to 1.0 μM, about 0.5 to 1.0 μM, and about 0.75 to 1.0 μM The growth promoting composition of the present invention can be used in culturing corneal endothelial cells. Corneal endothelial cells are typically cultured in the following manner.

<1> Collection of Corneal Endothelial Cells and Culture Thereof in Test Tube

Corneal endothelial cells are collected by a conventional method from a cornea of the recipients themselves or a suitable donor. If the transplantation condition in the present invention is considered, it is sufficient to prepare allogenic corneal endothelial cells. For example, the Descemet's membrane and endothelial cell layer of corneal tissue are detached from the corneal stroma and then transferred into a culture dish and treated with dispase or the like. The corneal endothelial cells fall off from the Descemet's membrane thereby. The corneal endothelial cells remaining on the Descemet's membrane can be detached by pipetting or the like. After removing the Descemet's membrane, the corneal endothelial cells are cultured in the culture solution of the present invention. Examples of media and culture solutions that can be used include commercially available DMEM (Dulbecco's Modified Eagle's Medium) (e.g., THERMO-FISCHER=INVITROGEN, catalog number: 12320 or the like) to which FBS (fetal bovine serum) (e.g., BIOWEST, catalog number: S1820-500), b-FGF (basic fibroblast growth factor) (e.g., THERMO-FISCHER=INVITROGEN, catalog number: 13256-029), and an antibiotic such as penicillin or streptomycin are appropriately added and components of the growth promoting composition of the present invention are further added. It is preferable to use a culture vessel (culture dish) with type I collagen, type IV collagen, fibronectin, laminin, extracellular matrix of bovine corneal endothelial cells or the like is coated on the surface. Alternatively, a common culture vessel treated with a commercially available coating agent such as FNC Coating Mix® (50 ml (AES-0407), ATHENA, catalog number: 0407) may be used.

The temperature condition for culturing corneal endothelial cells is not particularly limited as long as the corneal endothelial cells grow. For example, the temperature is about 25° C. to about 45° C., and for efficient growth the temperature is preferably about 30° C. to about 40° C., and more preferably about 37° C. A culturing method is performed under humid conditions in an environment with a $CO_2$ concentration of about 5 to 10% in a common incubator for cell culture.

<2> Passage

Corneal endothelial cells subjected to culture can be passaged after growth. Preferably, the corneal endothelial cells are passaged at sub-confluence or confluence. The cells can be passaged as follows. First, cells are detached from the culture vessel surface by treating the cells with trypsin-EDTA or the like, and then the cells are collected. A medium or culture solution comprising the growth promoting composition of the present invention is added to the collected cells to prepare a cell suspension. The cells are preferably centrifuged when or after collecting the cells. A cell suspension with high cell density can be prepared by such centrifugation. A preferred cell density is about 1 to $2\times10^6$ cells/mL. Centrifugation conditions in this regard are, for example, 500 rpm (30 g) to 1000 rpm (70 g) and 1 to 10 minutes.

The cell suspension is seeded in a culture vessel in the same manner as the above primary culture and subjected to culture. The dilution factor as of passage varies depending on the condition of the cells, but is about 1:2 to 1:4, and preferably about 1:3. The cells can be passaged under the same culture condition as the above primary culture. The culturing time varies depending on the condition of the cells used or the like, but is for example 7 to 30 days. Such passage can be performed multiple times as needed. Growth can be promoted to shorten the culturing period by using the growth promoting composition of the present invention in a medium or culture solution comprising the growth promoting composition.

Reference literature such as scientific literature, patents, and patent applications cited herein is incorporated herein by reference to the same extent that the entirety of each document is specifically described.

The present invention has been explained while showing preferred embodiments to facilitate understanding. The present invention is explained hereinafter based on Examples. The above explanation and the following Examples are not provided to limit the present invention, but for the sole purpose of exemplification. Thus, the scope of the present invention is not limited to the embodiments and Examples that are specifically disclosed herein and is limited only by the scope of claims.

Examples

Hereinafter, examples of the present invention are described. Biological samples or the like, where applicable, were handled in compliance with the standards enacted by the Ministry of Health, Labour and Welfare, Ministry of Education, Culture, Sports, Science and Technology, or the like and, where applicable, based on the Helsinki Declaration or ethical codes prepared based thereon. For the donation of eyes used for the study, consent was obtained from close relatives of all deceased donors. The present study was approved by the ethics committee or a corresponding body of the University of Erlangen-Nuremberg (Germany) and SightLife™ (Seattle, Wash.) eye bank.

(Preparation Example: Production of Fuchs' Endothelial Corneal Dystrophy Patient Derived Immobilized Corneal Endothelial Cell Line (iFECD) Model)

In this example, an immobilized corneal endothelial cell line (iFECD) was made from corneal endothelial cells from Fuchs' endothelial corneal dystrophy patients.

(Culture Method)

Corneal endothelial cells were mechanically peeled off with a basal membrane from a cornea for research purchased from the Seattle Eye Bank. After using collagenase to detach and collect the corneal endothelial cell from the basal membrane, the cells were subjected to primary culture. For a medium, Opti-MEM I Reduced-Serum Medium, Liquid (INVITROGEN catalog number: 31985-070), to which 8% FBS (BIOWEST, catalog number: S1820-500), 200 mg/mL of $CaCl_2.2H_2O$ (SIGMA catalog number: C7902-500G), 0.08% of chondroitin sulfate (SIGMA catalog number: C9819-5G), 20 μg/mL of ascorbic acid (SIGMA catalog number: A4544-25G), 50 μg/mL of gentamicin (INVITROGEN catalog number: 15710-064) and 5 ng/mL of EGF (INVITROGEN catalog number: PHG0311) were added, and conditioned for a 3T3 feeder cell was used as a basal medium. Further, the cells were cultured in a basal medium to which SB431542 (1 μmol/L) and SB203580 (4-(4-fluorophenyl)-2-(4-methylsulfonylphenyl)-5(4-pyridyl) imidazole<4-[4-(4-fluorphenyl)-2-(4-methylsulfinylphenyl)-1H-imidazole-5-yl]pyridine) (1 μmol/L) were added (also referred to as "SB203580+SB431542+3T3 conditioned medium" herein).

(Method of Acquisition)

Corneal endothelial cells were obtained with approval from an ethics committee and written consent from 3 human patients who suffered from bullous keratopathy according to a clinical diagnosis of Fuchs' endothelial corneal dystrophy and underwent corneal endothelial transplant (Descemet's Membrane Endothelial Keratoplasty=DMEK). For DMEK, pathological corneal endothelial cells were mechanically peeled off with the basal membrane, i.e., the Descemet's membrane, and immersed in a cornea preservation solution Optisol-GS (Bausch & Lomb). Collagenase treatment was then applied to enzymatically collect the corneal endothelial cells, and the cells were cultured with a SB203580+SB431542+3T3 conditioned medium. For cultured corneal endothelial cells from a Fuchs' endothelial corneal dystrophy patient, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) with a transfection reagent (Fugene HD; Promega Corp., Madison, Wis.) and three types of helper plasmids (pLP1, pLP2, pLP/VSVG; Life Technologies Inc.). Culture supernatant comprising viruses was collected after 48 hours from the infection. 5 μg/ml of polybrene was used and added to a culture solution of cultured corneal endothelial cells from a Fuchs' endothelial corneal dystrophy patient, and SV40 large T antigen and hTERT gene were introduced. Images of immobilized corneal endothelial cell line (iFECD) from Fuchs' endothelial corneal dystrophy patients from a phase difference microscope were studied. Cultured corneal endothelial cells from a research cornea imported from the Seattle Eye Bank were immobilized by the same method to make an immobilized cell line of normal corneal endothelial cells (iHCEC) as a control. When images of the immobilized corneal endothelial cell line (iFECD) and the immobilized corneal endothelial cell line from a healthy donor (iHCEC) from a phase difference microscope are studied, both iHCEC and iFECD have a layer of polygonal form as in normal corneal endothelial cells. IHCEC and iFECD were maintained and cultured with DMEM+10% FBS.

Example 1: Suppression of Caspase 3 Activation by Caspase Inhibitor after UV Irradiation This Example studied the suppression of caspase 3 activation by a caspase inhibitor after UV irradiation.

(Materials and Methods)

$5 \times 10^3$ cultured monkey corneal endothelial cells were seeded on a 96-well plate coated with FNC Coating Mix and were cultured until reaching confluence under the condition of 5% $CO_2$ at 37° C. Dulbecco's Modified Eagle Medium (DMEM) (Gibco, 12320-032)+10% FBS+1% penicillin-streptomycin (nacalai tesque, 26252-94) was used as the medium.

This Example used the following caspase inhibitors.
Z-VD-FMK (10 μM)
Z-VAD-FMK (10 μM)
Emricasan (10 μM)

Next, each inhibitor was added at the above concentration. The cells were incubated for 18 hours under the condition of 5% $CO_2$ at 37° C. The control group and the UV irradiation group were supplemented with a solvent of each reagent, i.e., DMSO (Dimethyl Sulfoxide, Sterile-filtered) (nacalai tesque, 13408-64). Gibco DMEM+1% P/S (penicillin-streptomycin) was used as the medium.

The cell supernatant was then removed, and the cells were irradiated with UV (300 $J/m^2$). After irradiation, media containing each inhibitor were added to the cells again. The cells were cultured for 7 hours. Caspase 3/7 activity was then measured using Caspase-Glo 3/7 Assay (Promega, #G8091).

(Results)
(Caspase Inhibitor has Suppressed Caspase 3 Activity Upon Cell Damage)

The graph of FIG. 1 shows the ratio of caspase 3/7 activity when each caspase inhibitor was added to the caspase 3/7 activity when UV was irradiated without adding caspases.

As shown, when each inhibitor was added, the same caspase 3/7 activity as the control group without UV addition was exhibited, thus demonstrating that a caspase inhibitor suppresses caspase 3 activation upon cell damage.

Example 2: Examination of Effect of Caspase Inhibitor on Apoptosis of Cultured Monkey Corneal Endothelial Cells This Example examined the effect of caspase inhibitor Z-VD-FMK on apoptosis of cultured monkey corneal endothelial cells.

(Materials and Methods)

$1 \times 10^5$ cultured monkey corneal endothelial cells were seeded on a 12-well plate coated with FNC Coating Mix and were cultured until reaching confluence under the condition of 5% $CO_2$ at 37° C. Dulbecco's Modified Eagle Medium (DMEM) (Gibco, 12320-032)+10% FBS+1% Penicillin-Streptomycin (nacalai tesque, 26252-94) was used as the medium.

This Example used the following caspase inhibitors.
Z-VAD-FMK (10 µM)
Z-VD-FMK (3, 10, 20, 30, and 50 µM)
Emricasan (1, 3, 10, 30, and 100 µM)
Nivocasan (1, 3, 10, 30, and 100 µM)

Each inhibitor was added at the above concentration. The cells were incubated for 18 hours under the condition of 5% $CO_2$ at 37° C. The control group and the UV irradiation group were supplemented with a solvent of each reagent, i.e., DMSO (Dimethyl Sulfoxide, Sterile-filtered) (nacalai tesque, 13408-64). Gibco DMEM+1% P/S (penicillin-streptomycin mixture) was used as the medium.

The cell supernatant was then removed, and the cells were irradiated with UV (100 J/m²). After irradiation, media containing each inhibitor were added to the cells again. The cells were cultured for 9 hours.

The cell morphology was observed under a phase difference microscope. After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

8 µg of the extracted protein was separated by SDS-PAGE and transferred onto a nitrocellulose membrane. A rabbit anti-caspase 3 antibody (Cell Signaling, 9662), rabbit anti-PARP antibody (Cell Signaling, 9542), and mouse anti-GAPDH antibody (MBL, M171-3) were used as the primary antibodies. A peroxidase-labeled anti-rabbit antibody and anti-mouse antibody (GE Healthcare Biosciences, NA934V, NA931V) were used as the secondary antibodies. For the primary antibodies, rabbit anti-caspase 3 antibody and rabbit anti-PARP antibody: 1000-fold dilution and mouse anti-GAPDH antibody: 3000-fold dilution, while the secondary antibody was diluted 5000-fold. Chemi Lumi ONE Ultra (nacalai tesque, 11644-40) was used for detection. The detected band strength was analyzed with a lumino image analyzer LAS-4000 mini (Fuji Film) and ImageQuant™ software (GE Healthcare).

(Results)
(Caspase Inhibitor Suppresses Caspase 3 Activation and Cell Death Upon Cell Damage)

Figure 2:
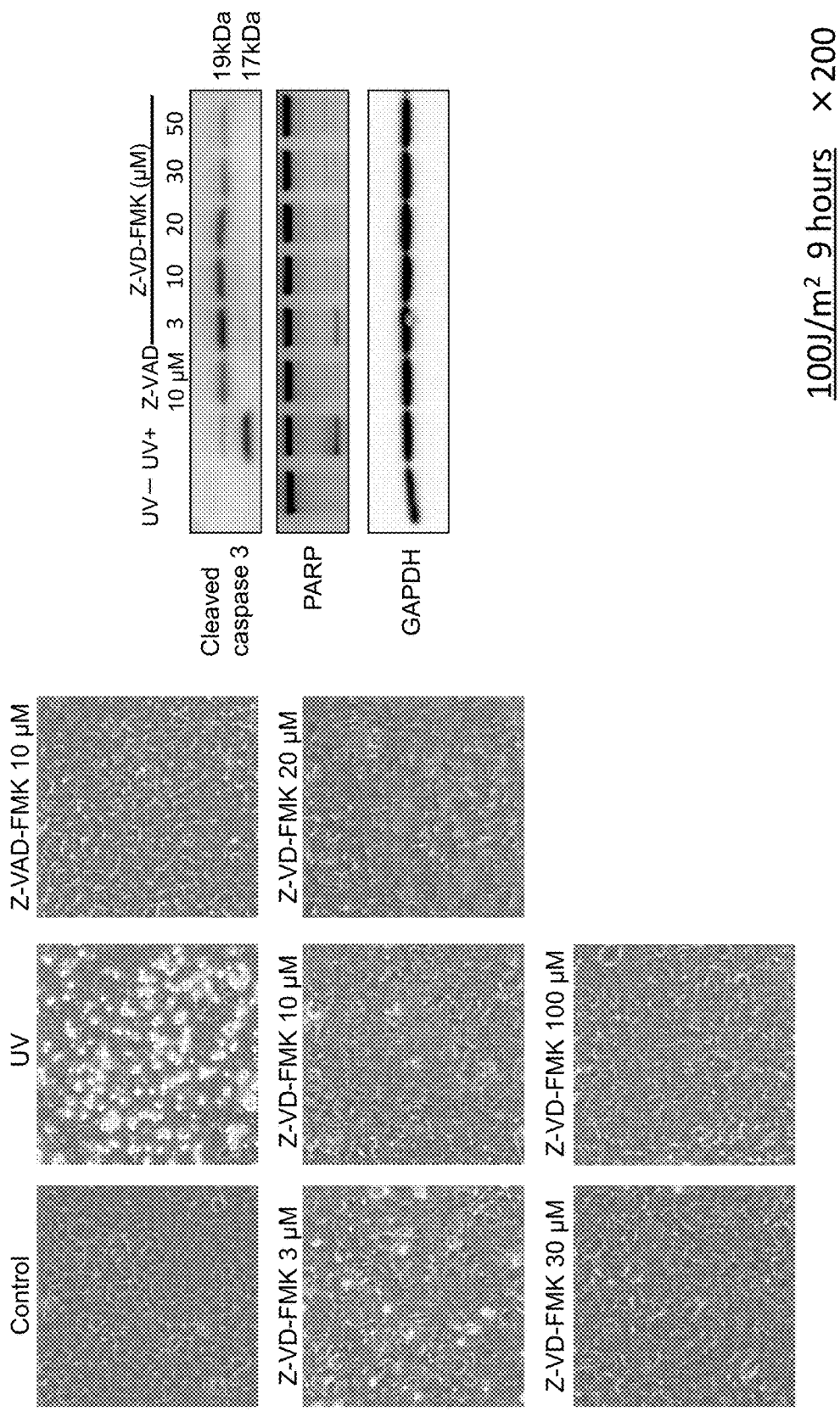
FIG. 2 shows microscope images of corneal endothelial cells after UV irradiation in the Z-VD-FMK supplemented groups and results of the western blots. The left panel shows phase difference microscope images (×200 magnification) of the control group, UV irradiation group, UV irradiation+Z-VAD-FMK supplemented group (10 μM), and UV irradiation+Z-VD-FMK supplemented groups (3, 10, 20, 30, and 100 μM). 100 J/m$^2$ was used as the UV intensity. The right panel shows results of the western blots of caspase 3, PARP, and GAPDH for each of the above groups.
Figure 3:
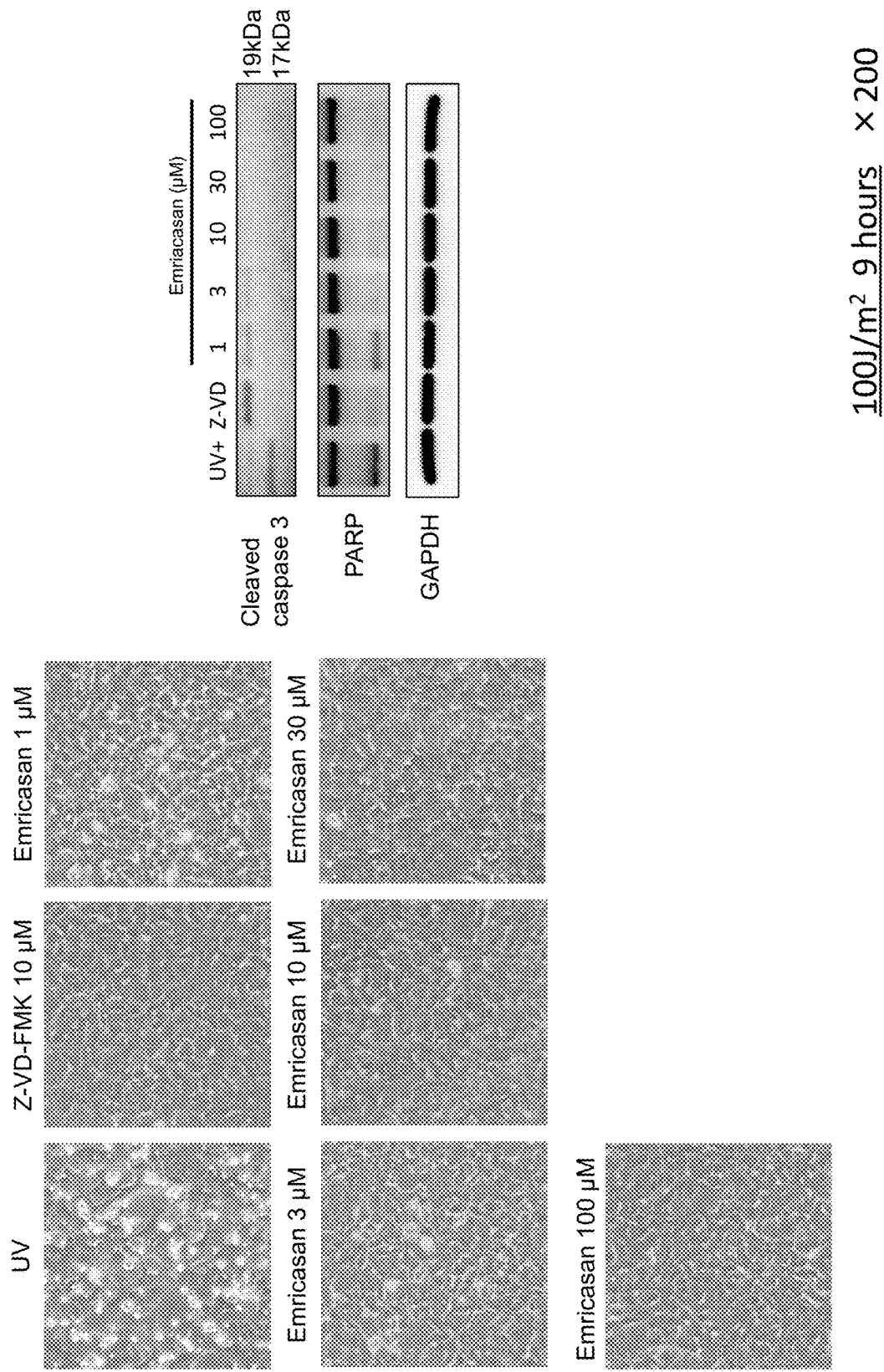
FIG. 3 shows microscope images of corneal endothelial cells after UV irradiation in the emricasan supplemented groups and results of the western blots. The left panel shows phase difference microscope images (×200 magnification) of the control group, UV irradiation group, UV irradiation+Z-VD-FMK supplemented group (10 μM), and UV irradiation+emricasan supplemented groups (1, 3, 10, 30, and 100 μM). 100 J/m$^2$ was used as the UV intensity. The right panel shows results of the western blots of caspase 3, PARP, and GAPDH for each of the above groups.
Figure 4:
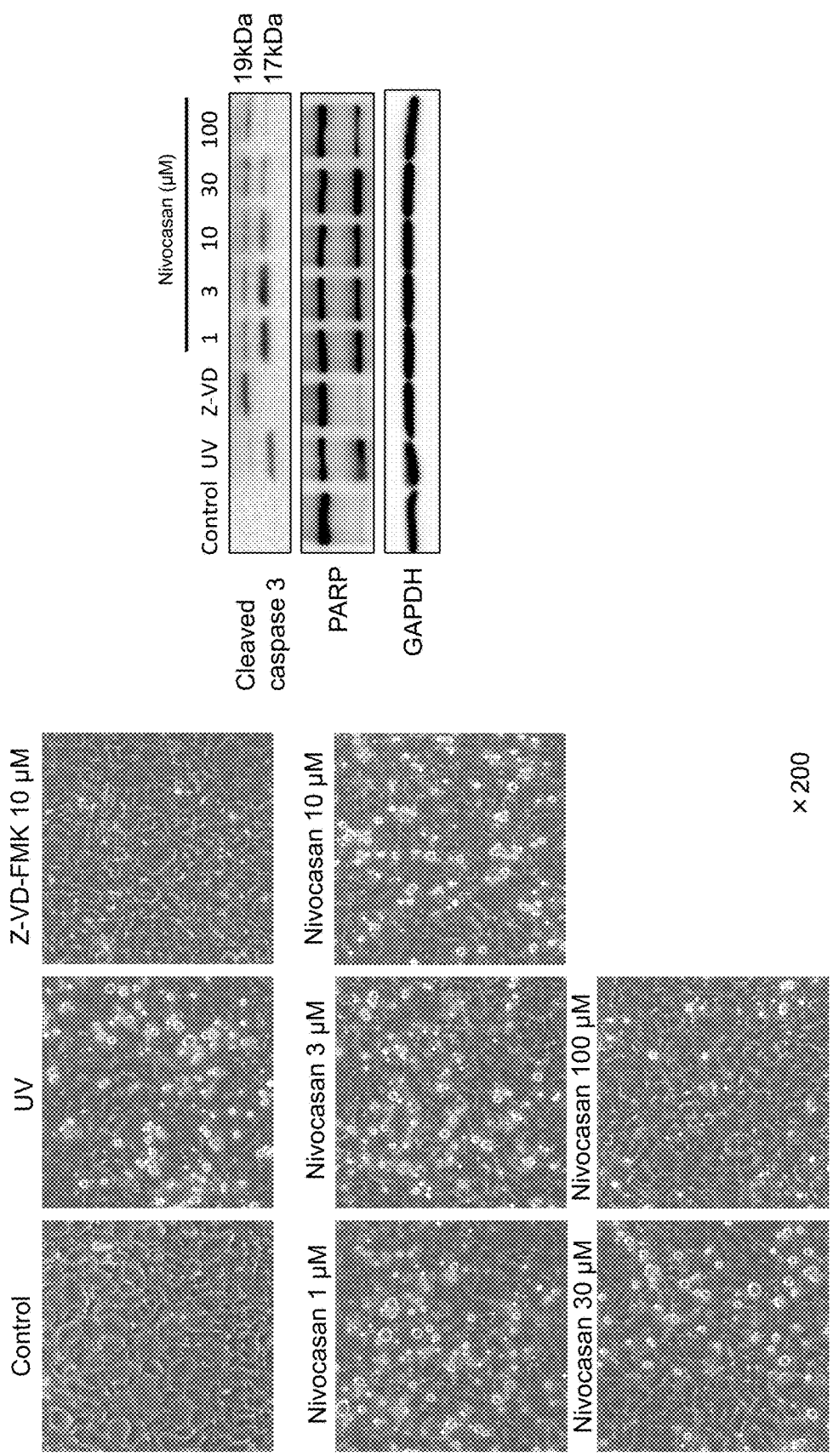
FIG. 4 shows microscope images of corneal endothelial cells after UV irradiation in the nivocasan supplemented groups and results of the western blots. The left panel shows phase difference microscope images (×200 magnification) of the control group, UV irradiation group, UV irradiation+Z-VD-FMK supplemented group (10 μM), and UV irradiation+nivocasan supplemented groups (1, 3, 10, 30, and 100 μM). 100 J/m$^2$ was used as the UV intensity. The right panel shows results of the western blots of caspase 3, PARP, and GAPDH for each of the above groups.

The results are shown in FIGS. 2 to 4. The UV irradiation groups were observed as having significant cell damage from phase difference microscope images. Furthermore, cleaved caspase 3 of about 17 kDa (active form) was found in the UV irradiation groups from the results of the western blots. In the UV irradiation+Z-VAD-FMK supplemented groups, active form cleaved caspase 3 of about 17 kDA was not observed in any of the tested concentration regions, while cleaved caspase 3 of about 19 kDa (inactive form) was observed (FIG. 2). Active form caspase 3 was not observed in the emricasan supplemented group in all tested concentration regions. In addition, inactive form cleaved caspase 3 of about 19 kDa was also hardly observed upon addition of 1 and 3 µM and was not observed at other concentrations (FIG. 3). This means that caspase 3 activation is strongly suppressed. The effect of suppressing caspase 3 was observed at a concentration of 100 µM in the nivocasan group (FIG. 4). It was revealed from these results that a caspase inhibitor suppresses caspase 3 activation upon cell damage.

Example 3: Effect of Caspase Inhibitor on Damage to Cultured Monkey Corneal Endothelial Cells Due to Hydrogen Peroxide This Example examined the effect of a caspase inhibitor on damage to cultured monkey corneal endothelial cells due to hydrogen peroxide.

(Materials and Methods)

$1 \times 10^5$ cultured monkey corneal endothelial cells were seeded on a 12-well plate coated with FNC Coating Mix and were cultured until reaching confluence under the condition of 5% $CO_2$ at 37° C. Dulbecco's Modified Eagle Medium (Gibco, 12320-032)+10% FBS+1% Penicillin-Streptomycin (nacalai tesque, 26252-94) was used as the medium.

This Example used the following caspase inhibitors.
Z-VAD-FMK (10 µM)
Z-VD-FMK (10 µM)
Emricasan (10 µM)
Nivocasan (100 µM)

Each inhibitor was added at the above concentration. The cells were incubated for 18 hours under the condition of 5% $CO_2$ at 37° C. The control group and the hydrogen peroxide group were supplemented with a solvent of each reagent, i.e., DMSO (Dimethyl Sulfoxide, Sterile-filtered) (nacalai tesque, 13408-64). Gibco DMEM+1% P/S was used as the medium.

The cell supernatant was then removed, and the cells were supplemented with a medium containing each inhibitor and 1000 µM hydrogen peroxide for 24 hours of culturing. The control group was supplemented with a solvent of hydrogen peroxide, sterilized water, and a solvent of each reagent, i.e., DMSO (Dimethyl Sulfoxide, Sterile-filtered) (nacalai tesque, 13408-64). The hydrogen peroxide group was supplemented with a medium supplemented with DMSO (Dimethyl Sulfoxide, Sterile-filtered) (nacalai tesque, 13408-64) and 1000 µM hydrogen peroxide.

The cell morphology and apoptosis were observed under a phase difference microscope. After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 5 minutes. The supernatant was discarded to obtain precipitates-. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot 9.6 µg of the extracted protein was separated by SDS-PAGE and transferred onto a nitrocellulose membrane. A rabbit anti-caspase 3 antibody (Cell Signaling, 9662), rabbit anti-PARP antibody (Cell Signaling, 9542), and mouse anti-GAPDH antibody (MBL, M171-3), and mouse anti-CHOP antibody (Cell Signaling, 2895) were used as the primary antibodies. A peroxidase-labeled anti-rabbit antibody and anti-mouse antibody (GE Healthcare Biosciences, NA934V, NA931V) were used as the secondary antibodies. For the primary antibodies, rabbit anti-caspase 3 antibody: 1000-fold dilution, rabbit anti-PARP antibody: 2000-fold dilution, and mouse anti-GAPDH antibody: 3000-fold dilution, while the secondary antibody was diluted 5000-fold. Chemi Lumi ONE Ultra (nacalai tesque, 11644-40) was used for detection. The detected band strength was analyzed with a lumino image analyzer LAS-4000 mini (Fuji Film) and ImageQuant™ software (GE Healthcare).

(Results)

(Caspase Inhibitor Suppresses Caspase 3 Activation Upon Cell Damage Due to Hydrogen Peroxide)

Figure 5:
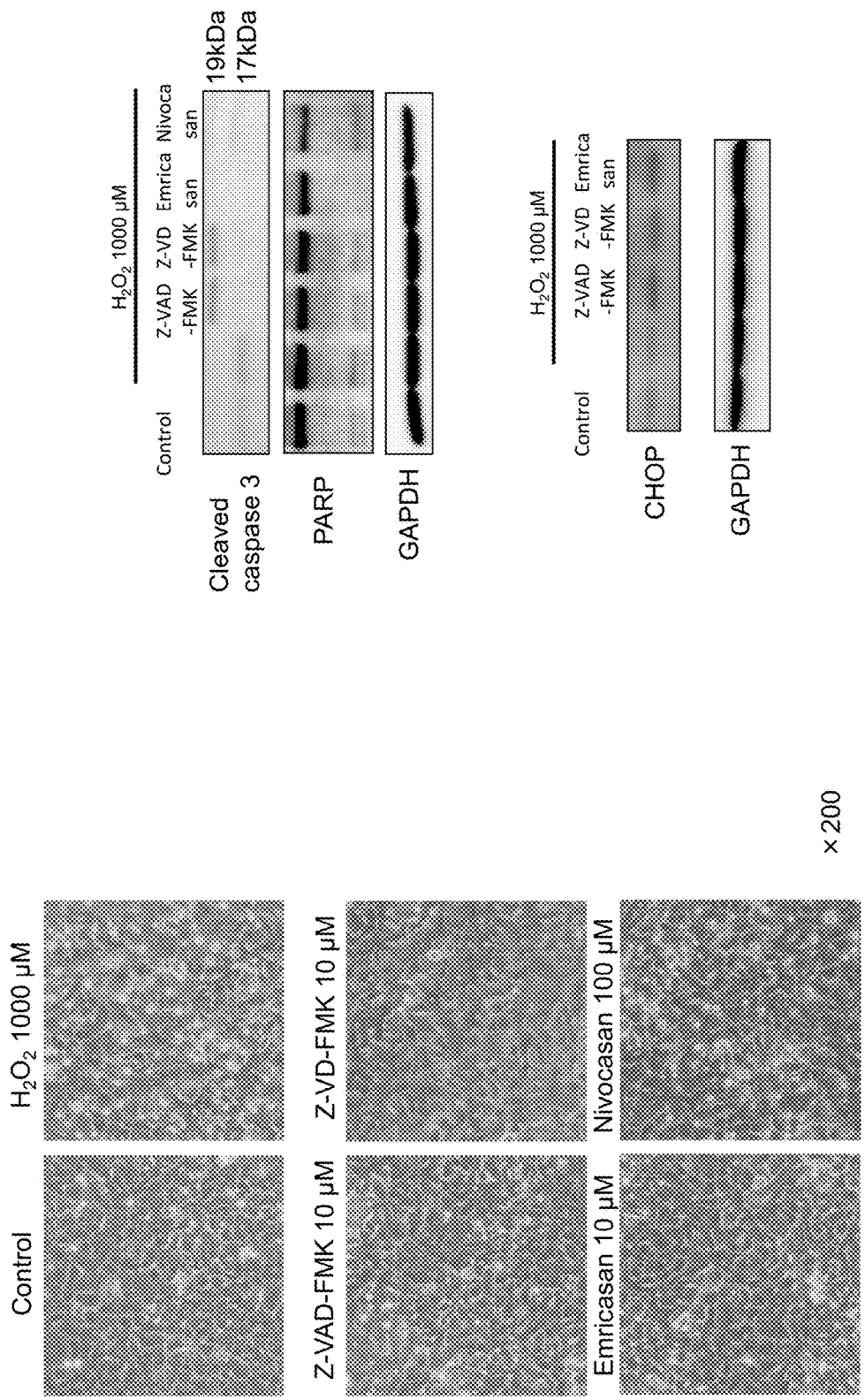
FIG. 5 shows the effect of a caspase inhibitor on damage to cultured monkey corneal endothelial cells due to hydrogen peroxide. The left panel shows phase difference microscope images (×200 magnification) of corneal endothelial cells in the control group, $H_2O_2$ supplemented group (1000 μM), $H_2O_2$+Z-VAD-FMK supplemented group (10 μM), $H_2O_2$+Z-VD-FMK supplemented group (10 μM), $H_2O_2$+emricasan supplemented group (10 μM), and $H_2O_2$+nivocasan supplemented group (100 μM). The right panel shows results of the western blots of caspase 3, PARP, GAPDH, and CHOP for each of the above groups.

Hydrogen peroxide is known to damage cells due to its potent oxidation action. This Example confirmed that a caspase inhibitor suppresses cell damage due to hydrogen peroxide. The results are shown in FIG. 5. As shown, active form cleaved caspase 3 was found in the group supplemented with only hydrogen peroxide, while active form cleaved caspase 3 was not found in the hydrogen peroxide+caspase inhibitor supplemented groups, such that cell damage was suppressed. Therefore, caspase inhibitors suppress caspase 3 activation upon cell damage due to hydrogen peroxide.

Example 4: Effect of Caspase Inhibitor on Damage to Cultured Monkey Corneal Endothelial Cells Due to MG132

This Example examined the effect of a caspase inhibitor on damage to cultured monkey corneal endothelial cells due to MG132.

(Materials and Methods)

$1 \times 10^5$ cultured monkey corneal endothelial cells were seeded on a 12-well plate coated with FNC Coating Mix and were cultured until reaching confluence under the condition of 5% $CO_2$ at 37° C. Dulbecco's Modified Eagle Medium (Gibco, 12320-032)+10% FBS+1% Penicillin-Streptomycin (nacalai tesque, 26252-94) was used as the medium.

This Example used the following caspase inhibitors.
Z-VAD-FMK (10 µM)
Z-VD-FMK (10 µM)
Emricasan (10 µM)
Nivocasan (100 µM)

Each inhibitor was then added at the above concentration. The cells were incubated for 6 hours under the condition of 5% $CO_2$ at 37° C. The control group and the MG132 group were supplemented with a solvent of each reagent, i.e., DMSO (Dimethyl Sulfoxide, Sterile-filtered) (nacalai tesque, 13408-64). Gibco DMEM+1% P/S was used as the medium.

The cell supernatant was then removed. 10 µM MG132 and media containing each inhibitor were added to the cells. The cells were cultured for 18 hours. The control group was supplemented with MG132 and a solvent of each reagent, i.e., DMSO (Dimethyl Sulfoxide, Sterile-filtered) (nacalai tesque, 13408-64).

The cell morphology and apoptosis were observed under a phase difference microscope. After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

10 µg of the extracted protein was separated by SDS-PAGE and transferred onto a nitrocellulose membrane. A rabbit anti-caspase 3 antibody (Cell Signaling, 9662), rabbit anti-PARP antibody (Cell Signaling, 9542), mouse anti-GAPDH antibody (MBL, M171-3), and mouse anti-CHOP antibody (Cell Signaling, 2895) were used as the primary antibodies. A peroxidase-labeled anti-rabbit antibody and anti-mouse antibody (GE Healthcare Biosciences, NA934V, NA931V) were used as the secondary antibodies. For the primary antibodies, rabbit anti-caspase 3 antibody: 1000-fold dilution, rabbit anti-PARP antibody: 2000-fold dilution, and mouse anti-GAPDH antibody: 3000-fold dilution, while the secondary antibody was diluted 5000-fold. Chemi Lumi ONE Ultra (nacalai tesque, 11644-40) was used for detection. The detected band strength was analyzed with a lumino image analyzer LAS-4000 mini (Fuji Film) and ImageQuant™ software (GE Healthcare).

(Results)

(Caspase Inhibitor Suppresses Cell Damage Due to Unfolded Protein Induced by MG132 and Suppresses Activation of Caspase 3 Due to Endoplasmic Reticulum Stress)

Figure 6:
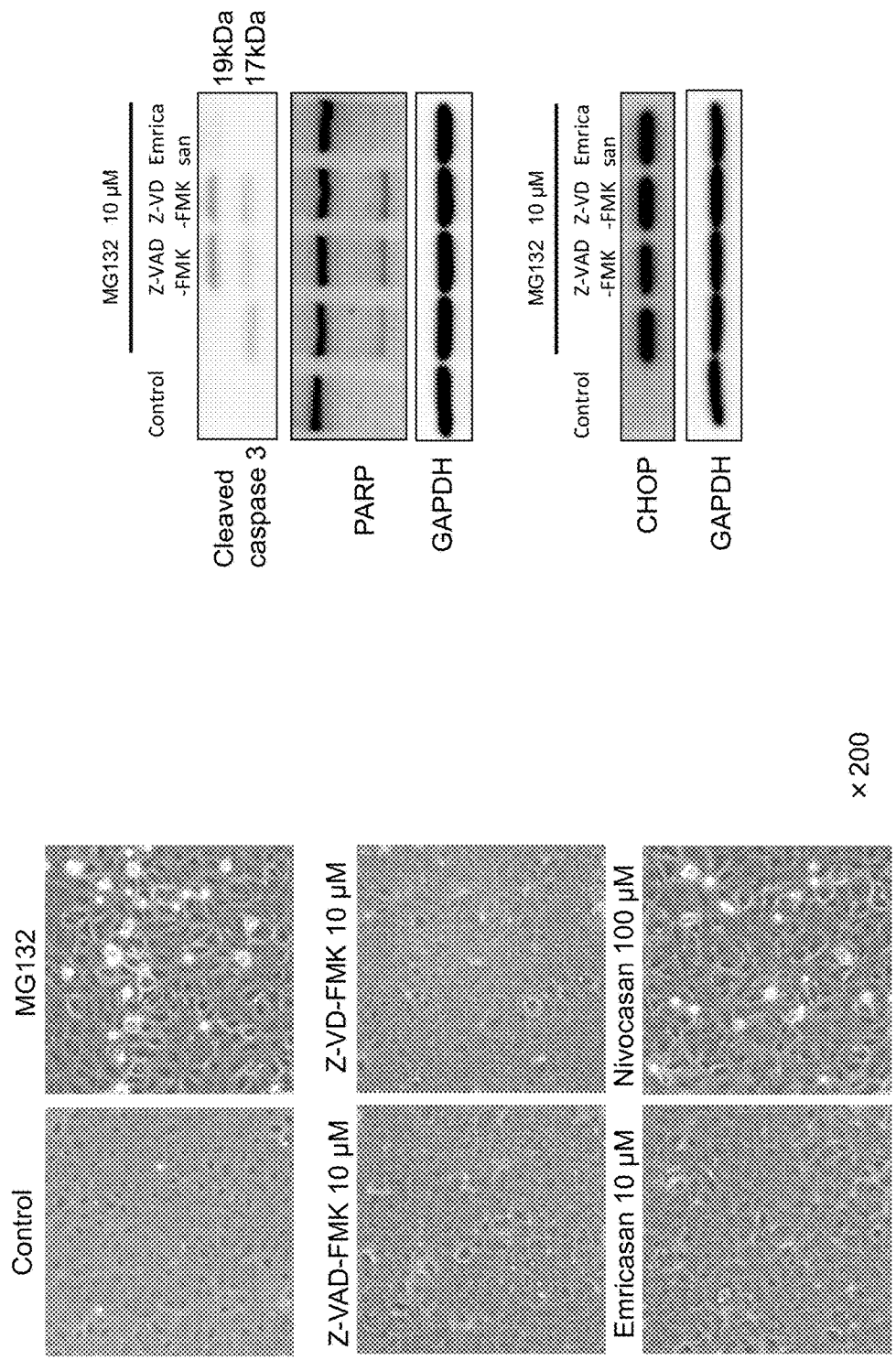
FIG. 6 shows the effect of a caspase inhibitor on damage to cultured monkey corneal endothelial cells due to MG132. The left panel shows phase difference microscope images (×200 magnification) of corneal endothelial cells in the control group, MG132 supplemented group (10 μM), MG132+Z-VAD-FMK supplemented group (10 μM), MG132+Z-VD-FMK supplemented group (10 μM), MG132+emricasan supplemented group (10 μM), and MG132+nivocasan supplemented group (100 μM). The right panel shows results of the western blots of caspase 3, PARP, GAPDH, and CHOP for each for the above groups.

MG132 is a proteasome inhibitor, which induces unfolded proteins and results in endoplasmic reticulum stress. Accumulation of endoplasmic reticulum stress activates caspase 3 and damages cells. This Example confirmed an effect of suppressing cell damage induced by MG132 in the caspase inhibitor supplemented groups. The results are shown in FIG. 6. Activation of caspase 3 observed in the MG132 group was not observed in the caspase inhibitor supplemented groups. Therefore, caspase inhibitors suppress caspase 3 activation due to endoplasmic reticulum stress induced by MG132.

(Example 5: Examination of Effect of Caspase Inhibitor on Damage to Cultured Monkey Corneal Endothelial Cells Due to Thapsigargin (TG))

This Example examined the effect of a caspase inhibitor on damage to cultured monkey corneal endothelial cells due to TG.

(Materials and Methods)

$1 \times 10^5$ cultured monkey corneal endothelial cells were seeded on a 12-well plate coated with FNC Coating Mix and were cultured until reaching confluence under the condition of 5% $CO_2$ at 37° C. Dulbecco's Modified Eagle Medium (Gibco, 12320-032)+10% FBS+1% Penicillin-Streptomycin (nacalai tesque, 26252-94) was used as the medium.

This Example used the following caspase inhibitors.
Z-VAD-FMK (10 μM)
Emricasan (10 μM)

Each inhibitor was added at the above concentration. The cells were incubated for 18 hours under the condition of 5% $CO_2$ at 37° C. The control group and the TG group were supplemented with a solvent of each reagent, i.e., DMSO (Dimethyl Sulfoxide, Sterile-filtered) (nacalai tesque, 13408-64). Gibco DMEM and 1% P/S were used as the medium.

The cell supernatant was then removed. 10 μM of TG and media containing each inhibitor were added to the cells. The cells were cultured for 5 hours. The control group was supplemented with TG and a solvent of each reagent, i.e., DMSO (Dimethyl Sulfoxide, Sterile-filtered) (nacalai tesque, 13408-64).

The cell morphology was observed under a phase difference microscope. After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot 5.7 μg of the extracted protein was separated by SDS-PAGE and transferred onto a nitrocellulose membrane. A rabbit anti-caspase 3 antibody (Cell Signaling, 9662), rabbit anti-PARP antibody (Cell Signaling, 9542), mouse anti-GAPDH antibody (MBL, M171-3), and mouse anti-CHOP antibody (Cell Signaling, 2895) were used as the primary antibodies. A peroxidase-labeled anti-rabbit antibody and anti-mouse antibody (GE Healthcare Biosciences, NA934V, NA931V) were used as the secondary antibodies. For the primary antibodies, rabbit anti-caspase 3 antibody: 1000-fold dilution, rabbit anti-PARP antibody: 2000-fold dilution, and mouse anti-GAPDH antibody: 3000-fold dilution, while the secondary antibody was diluted 5000-fold. Chemi Lumi ONE Ultra (nacalai tesque, 11644-40) was used for detection. The detected band strength was analyzed with a lumino image analyzer LAS-4000 mini (Fuji Film) and ImageQuant™ software (GE Healthcare).

(Results)

(Caspase Inhibitor Suppresses Cell Damage Due to Unfolded Proteins Induced by Thapsigargin (TG) and Suppresses Caspase 3 Activation Due to Endoplasmic Reticulum Stress)

Figure 7:
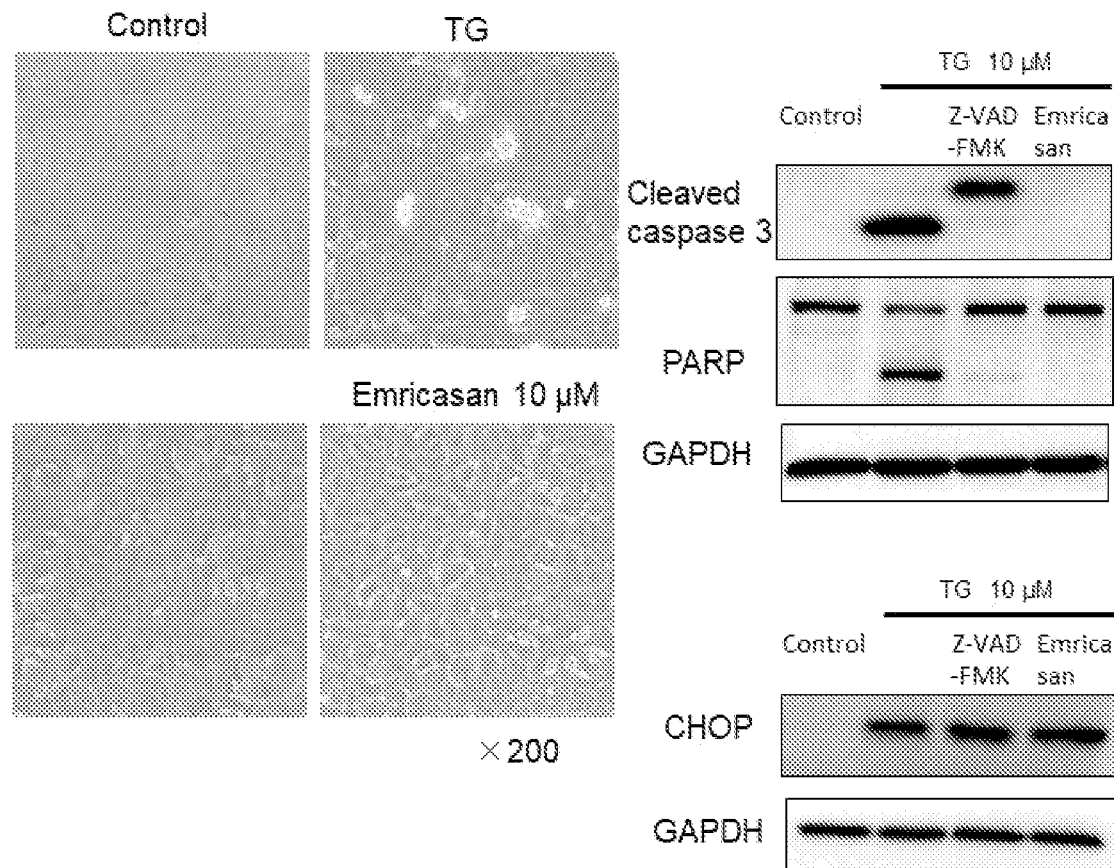
FIG. 7 shows the effect of a caspase inhibitor on damage to cultured monkey corneal endothelial cells due to thapsigargin (TG). The left panel shows phase difference microscope images (×200 magnification) of corneal endothelial cells in the control group, TG supplemented group (10 μM), TG+Z-VAD-FMK supplemented group (10 μM), and TG+emricasan supplemented group (10 μM). The right panel shows results of the western blots of caspase 3, PARP, GAPDH, and CHOP for each of the above groups.

Thapsigargin (TG) induces endoplasmic reticulum stress just like MG132. This Example confirmed the effect of suppressing cell damage induced by TG in the caspase inhibitor supplemented groups. The results are shown in FIG. 7. Cleaved caspase of about 17 kDa (active form) was observed when adding only TG, while active form cleaved caspase was not observed when a caspase inhibitor was added. Therefore, caspase inhibitors suppress caspase 3 activation due to endoplasmic reticulum stress induced by TG.

Example 6: Effect of Caspase Inhibitor on Cell Damage in Cultured Monkey Corneal Endothelial Cells Due to CCCP This Example examined the effect of a caspase inhibitor on cell damage in cultured monkey corneal endothelial cells due to CCCP.

(Materials and Methods)

$1 \times 10^5$ cultured monkey corneal endothelial cells were seeded on a 12-well plate coated with FNC Coating Mix and were cultured until reaching confluence under the condition of 5% $CO_2$ at 37° C. Dulbecco's Modified Eagle Medium (Gibco, 12320-032)+10% FBS+1% Penicillin-Streptomycin (nacalai tesque, 26252-94) was used as the medium.

This Example used the following caspase inhibitors.
Z-VAD-FMK (10 μM)
Z-VD-FMK (10 μM)
Emricasan (10 μM)

Each inhibitor was added at the above concentration. The cells were incubated for 16 hours under the condition of 5% $CO_2$ at 37° C. The control group and the CCCP group were supplemented with a solvent of each reagent, i.e., DMSO (Dimethyl Sulfoxide, Sterile-filtered) (nacalai tesque, 13408-64). Gibco DMEM+1% P/S was used as the medium.

The cell supernatant was then removed. 50 μM of CCCP and media containing each inhibitor were added to the cells. The cells were cultured for 6 hours. The control group was supplemented with CCCP and a solvent of each reagent, i.e., DMSO (Dimethyl Sulfoxide, Sterile-filtered) (nacalai tesque, 13408-64).

The cell morphology was observed under a phase difference microscope. After observation, western blot was performed on proteins by the following procedure.

1) Protein Collection

The medium was collected on ice to collect free and dead cells. The solution from washing the cells twice with 1×PBS (−) was also collected, and was centrifuged at 4° C. at 800×g for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

5 μg of the extracted protein was separated by SDS-PAGE and transferred onto a nitrocellulose membrane. A rabbit anti-caspase 3 antibody (Cell Signaling, 9662), rabbit anti-PARP antibody (Cell Signaling, 9542), and mouse anti-GAPDH antibody (MBL, M171-3) were used as the primary antibodies. A peroxidase-labeled anti-rabbit antibody and anti-mouse antibody (GE Healthcare Biosciences, NA934V, NA931V) were used as the secondary antibodies. For the primary antibodies, rabbit anti-caspase 3 antibody at 1000-fold dilution, rabbit anti-PARP antibody at 2000-fold dilution, and mouse anti-GAPDH antibody at 3000-fold dilution, while the secondary antibody was diluted 5000-fold. Chemi Lumi ONE Ultra (nacalai tesque, 11644-40) was used for detection. The detected band strength was analyzed with a lumino image analyzer LAS-4000 mini (Fuji Film) and ImageQuant™ software (GE Healthcare).

(Results)

(Caspase Inhibitor Suppresses Mitochondrial Dependent Programmed Cell Death Due to Decrease in Mitochondrial Membrane Potential Induced by CCCP)

Figure 8:
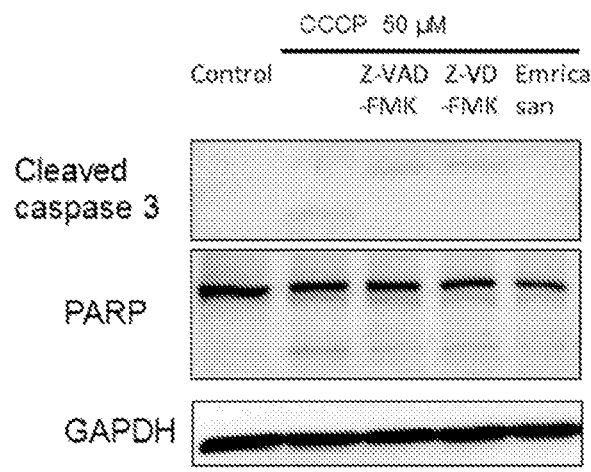
FIG. 8 shows the effect of a caspase inhibitor on damage to cultured monkey corneal endothelial cells due to CCCP. The results of the western blots of caspase 3, PARP, and GAPDH for the control group, CCCP supplemented group (50 μM), CCCP+Z-VAD-FMK supplemented group (10 μM), CCCP+Z-VD-FMK supplemented group (10 μM), and CCCP+emricasan supplemented group (10 μM) are shown.

When an uncoupling agent CCCP is added, mitochondrial membrane potential decreases due to uncoupling to induce a mitochondrial disorder. A mitochondrial disorder induces programmed cell death, i.e., activates caspases. For this reason, when CCCP was added, cleaved caspase 3 of about 17 kDa was observed, as well as the activation of caspase 3 (FIG. 8). However, when a caspase inhibitor was added, caspase 3 activation was suppressed. It was revealed from these results that cell damage due to a mitochondrial disorder can be suppressed.

Example 7: Observation of Fluorescence of Annexin V in UV-Irradiated Rabbit Corneal Endothelial Cells This Example observed fluorescence of Annexin V in UV-irradiated rabbit corneal endothelial cells.

(Materials and Methods)

This Example used the following caspase inhibitors.
Z-VAD-FMK (10 μM)
Z-VD-FMK (10 μM)
Emricasan (10 μM)
Nivocasan (100 μM)

This Example used rabbit eye balls after 0 to 24 hours from euthanasia. Under a stereoscopic microscope, the sclera was excised using spring scissors along the corneal limbus, and the lens and iris were removed to prepare a sclerocornea fragment. The sclerocornea fragment was divided into four pieces as the control group and each caspase inhibitor supplemented group. After dividing the cornea, the control group was pretreated with DMSO supplemented Optisol-GS® (Bausch & Lomb) and the caspase inhibitor supplemented groups were pretreated with Optisol-GS® supplemented with each inhibitor for 16 hours while being shaded. After washing the cornea twice with PBS (-), UV was irradiated onto the corneal endothelial cells at 250 J/m$^2$, and the cells were again stored while being shaded for 24 hours at 4° C. DMSO was used for the control group, and Optisol-GS® supplemented with each reagent was used for the caspase inhibitor supplemented groups as the preservation solution.

The sclerocornea fragment was washed with PBS (-) and stained for 15 minutes at 37° C. using MEBCYTO-Apoptosis Kit (Annexin V-FITC Kit) (manufacturer: MBL, Code: 4700). The fragment was then immobilized with 4% formaldehyde for 10 minutes. After immobilization, the fragment was stained for 30 minutes with a DAPI Solution (manufacturer: DOJINDO, Code: GA098) and supplemented with an antifade agent for mounting. Annexin V and the nucleus were observed by fluorescent imaging using a confocal microscope. Further, the ratio of Annexin V positive cells was measured by flow cytometry.

(Results)

(Caspase Inhibitor Suppresses Programmed Cell Death of Corneal Endothelial Cells Due to Cell Damage)

Figure 9:
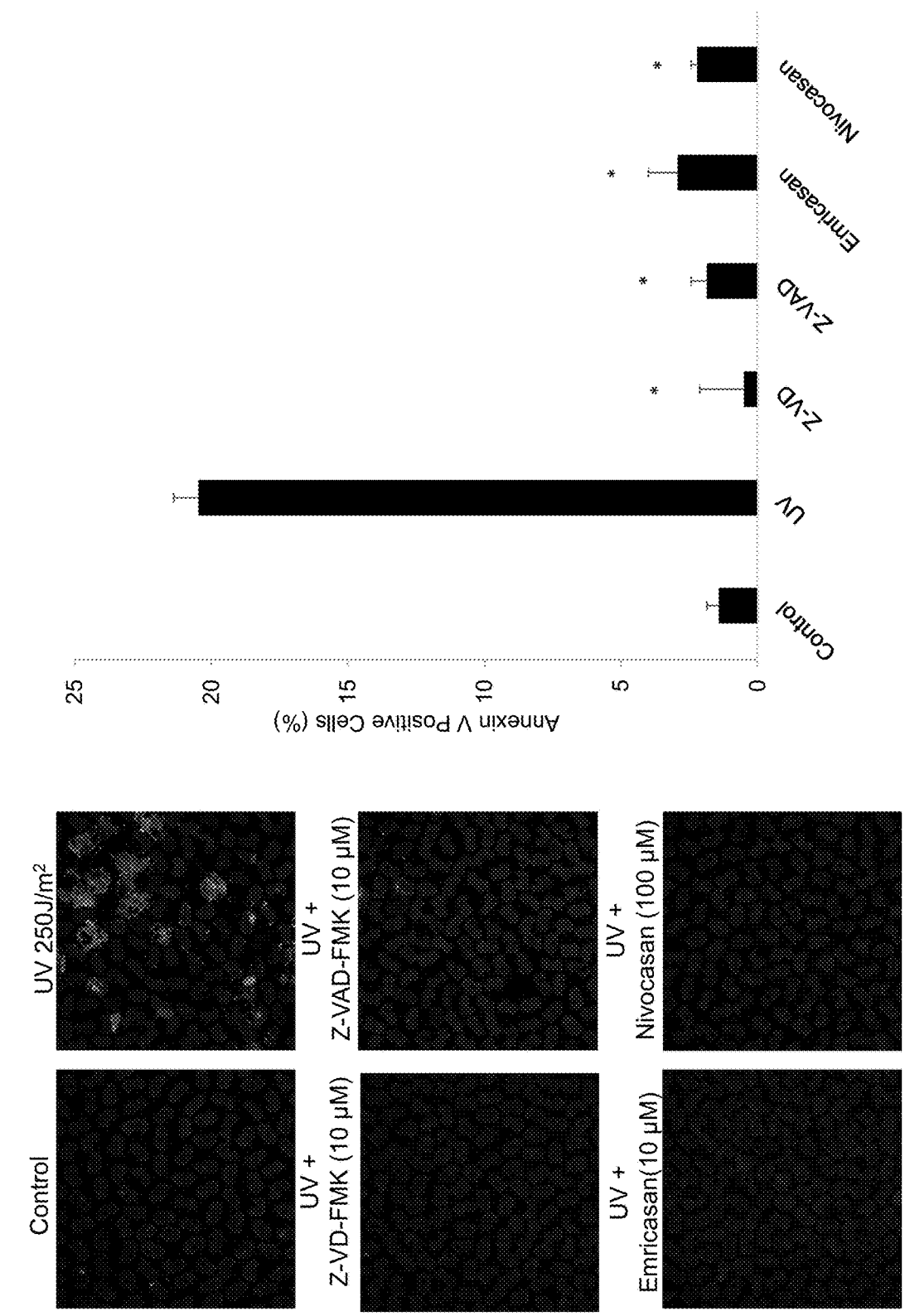
FIG. 9 shows the observed fluorescence of Annexin V in UV-irradiated rabbit corneal endothelial cells. The left panel shows confocal microscope images of the control group, UV irradiation group (250 J/m$^2$), UV+Z-VD-FMK supplemented group (10 μM), UV+Z-VAD-FMK supplemented group (10 μM), UV+emricasan supplemented group (10 μM), and UV+nivocasan supplemented group (100 μM). In the right graph, the vertical axis shows the Annexin V positive cells (%), and the horizontal axis shows, from the left, the control group, UV irradiation group, UV+Z-VD-FMK supplemented group, UV+Z-VAD-FMK supplemented group, UV+emricasan supplemented group, and UV+nivocasan supplemented group. * indicates statistical significance (p<0.01).

As shown in FIG. 9, Annexin V positive apoptotic cells were observed in the UV irradiation group, and the ratio thereof was notably high. Meanwhile, fluorescence of Annexin V was hardly observed in the caspase inhibitor supplemented groups. The ratio of Annexin V positive cells was lower than or equal to the ratio of Annexin V positive cells of the control group without UV irradiation.

Example 8: Observation of Functional Disorder and Morphological Abnormality in UV Irradiated Rabbit Corneal Endothelial Cells In this Example, functional disorders and morphological abnormalities in UV irradiated rabbit corneal endothelial cells were observed under a confocal microscope.

(Materials and Methods)

This Example used the following caspase inhibitors.
Z-VD-FMK (10 μM)
Z-VAD-FMK (10 μM)
Emricasan (10 μM)

This Example used rabbit eye balls after 0 to 24 hours from euthanasia. Under a stereoscopic microscope, the sclera was excised using spring scissors along the corneal limbus, and the lens and iris were removed to prepare a sclerocornea fragment. The sclerocornea fragment was divided into four pieces as the control group and each caspase inhibitor supplemented group. After dividing the cornea, the control group was pretreated with DMSO supplemented Optisol-GS® (Bausch & Lomb) and the caspase inhibitor supplemented groups were pretreated with Optisol-GS® supplemented with each reagent for 16 hours while being shaded. After washing the cornea twice with PBS (-), UV was irradiated onto the corneal endothelial cells at 250 J/m$^2$, and the cells were again stored while being shaded for 24 hours at 4° C. Optisol-GS® supplemented with each inhibitor was used for the caspase inhibitor supplemented groups as the preservation solution, while Optisol-GS® supplemented with DMSO, which is a solvent of inhibitors, was used for the control group.

After washing the sclerocornea fragment with PBS (-), the fragment was immobilized with 4% formaldehyde for 10 minutes at room temperature (RT) and incubated for 60 minutes with 1% bovine serum albumin (BSA). Antibodies to N-cadherin (BD Bioscience) and ZO-1 (Zymed Laboratories) were used at 1:300 dilution. For secondary antibodies, Alexa Fluor® 488 labeled goat anti-mouse IgG (Life Technologies) and Alexa Fluor® (Invitrogen, A11009) were used at a dilution of 1:1000. 1:400 dilution of phalloidin (Life Technologies) 546 was used for actin staining. The nucleus of cells was then stained with DAPI (Cell stain DAPI Solution; Dojindo, Kumamoto, Japan). Fluorescence was then observed using a confocal microscope (TCS SP2 AOBS; Leica Microsystems, Wetzlar Germany).

(Results)
(Caspase Inhibitor Suppresses Functional Disorder and Morphological Abnormality in Corneal Endothelial Cells Due to Cell Damaging Stimulation)

Figure 10:
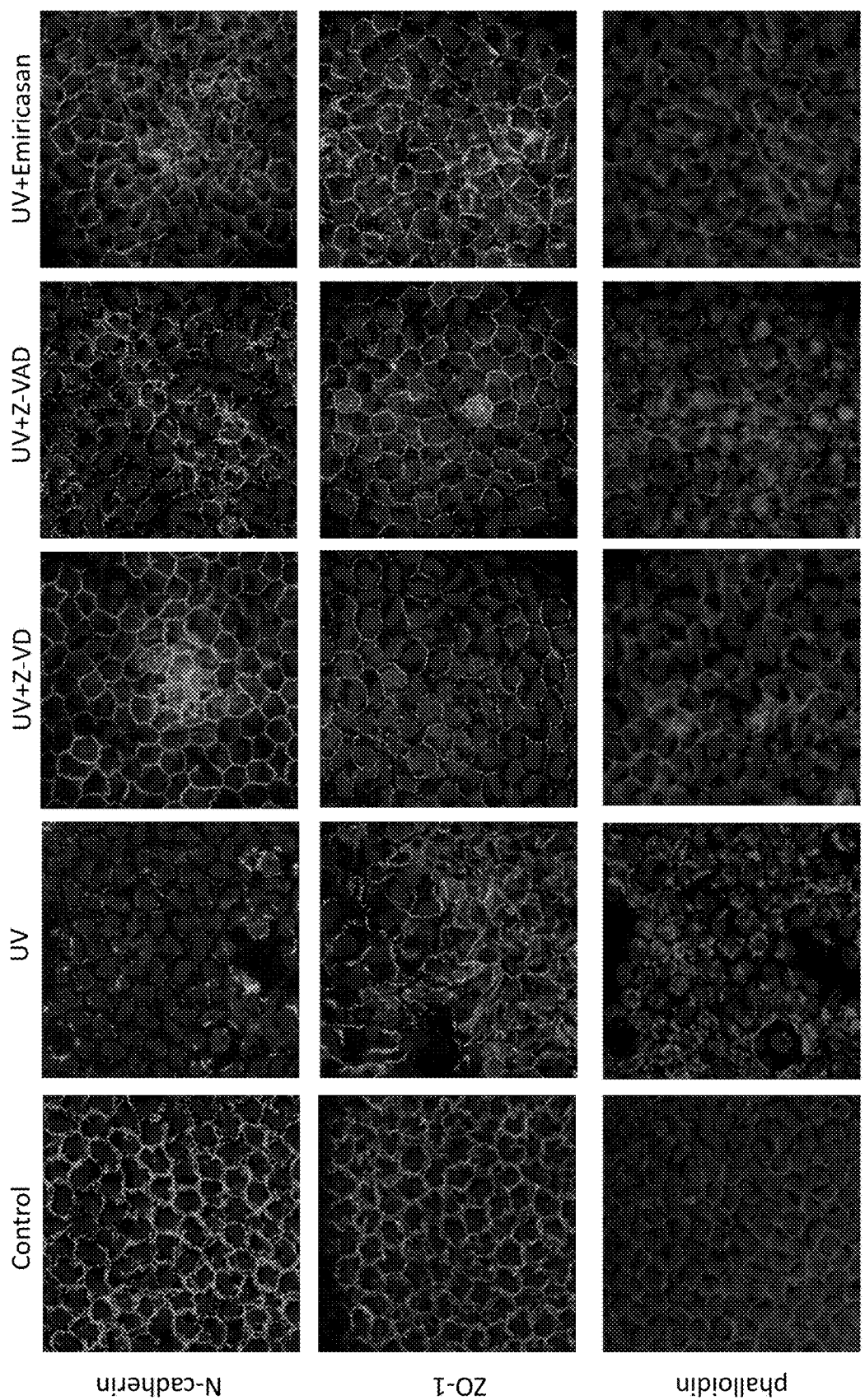
FIG. 10 shows the observed functional disorder and morphological abnormality in the UV-irradiated rabbit corneal endothelial cells. The top row shows the fluorescence of N-cadherin, the middle row shows the fluorescence of ZO-1, and the bottom row shows the fluorescence of phalloidin. The images show, from the left, the control group, UV irradiation group (250 J/m$^2$), UV+Z-VD-FMK supplemented group, UV+Z-VAD-FMK supplemented group, and UV+emricasan supplemented group of the corneal endothelial cells.

The results are shown in FIG. 10. N-cadherin and ZO-1 are proteins involved in adherens junctions and tight junctions. The barrier function, which is one of the functions of corneal endothelial cells, can be evaluated by observing the fluorescence thereof. In the UV irradiation group, fluorescence of N-cadherin was hardly observed. Thus, it can be understood that adherens junctions are damaged. From observing the fluorescence of ZO-1, it can be understood that tight junctions are damaged. Since phalloidin binds to actin, which has various roles including maintenance of cell morphology, the cell morphology can be evaluated. As can be seen from fluorescent images of phalloidin, actin localized in the cell cortex in the control is fragmented to exhibit abnormal localization in the UV irradiation group. In contrast to such observation in the UV control group, it can be observed that cell function/morphology that is the same as those of the control group (no UV irradiation) are maintained in the UV irradiation+caspase inhibitor supplemented groups.

(Example 9: Effect of Caspase Inhibitor on Cell Damage in Immobilized Fuchs' Endothelial Corneal Dystrophy Patient Derived Cells (iFECD) Due to TGF-$\beta$2)

This Example examined the effect of a caspase inhibitor on cell damage in immobilized Fuchs' endothelial corneal dystrophy patient derived cells (iFECD) due to TGF-$\beta$2.

$1.2 \times 10^5$ iFECDs were seeded on a 12-well plate coated without coating and were cultured for 24 hours under the condition of 5% $CO_2$ at 37° C. Dulbecco's Modified Eagle Medium (nacalai tesque, 26252-94)+10% FBS (Biological Industries/04-001-1A)+1% Penicillin-Streptomycin (nacalai tesque, 26252-94) was used as the medium.

After 24 hours from seeding, each inhibitor was added at a concentration of 10 µM and the cells were incubated for 24 hours under the condition of 5% $CO_2$ at 37° C. The medium was exchanged for the control group and the TGF-$\beta$2 group. DMEM+2% FBS+1% P/S was used as the medium.

The following reagents were used:
SB431542 (Wako Pure Chemical Industries, Ltd./192-16541); Z-VAD-FMK (Peptide Institute/3188-v); Z-VD-FMK (isomer mixture) (Wako Pure Chemical Industries, Ltd./262-02061); and emricasan (CHEMSCENE, LLC/CS-0599).

Next, TGF-$\beta$2 (manufacturer: R&D Systems, Inc., distributor: Wako Pure Chemical Industries, Ltd./manufacturer codes 302-B2-002, 302-B2-010, distributor codes: 553-62881, 5-59-62883) (10 ng/mL) alone, or both TGF-$\beta$2 (10 ng/mL) and each inhibitor (10 µM) were added. After 24 hours, cell morphology and programmed cell death were observed using a phase difference microscope.

After observation, the ratio of Annexin V position cells was examined using flow cytometry by the following procedure.

To collect suspended and dead cells, the solution from washing the cells twice with 1 mL of Dulbecco's PBS (−) (Nissui/05913) was collected, and incubated for 5 minutes after dripping in Accutase (INNOVAT/AT104) at 200 µL/well. After incubation, the cells were washed with 1 mL of Dulbecco's Modified Eagle's Medium (nacalai tesque, 26252-94) and centrifuged 1500 rpm for 5 minutes at 4° C. to discard the supernatant to obtain precipitates. 1 mL of Dulbecco's PBS (−) was added to the precipitates which were pipetted and centrifuged at 1500 rpm for 5 minutes at 4° C. to remove the supernatant. 92.5 µL of Binding Buffer (MBL/4700-300), 5 µL/well of Annexin V-FITC (Reagent) (MBL/4700-100), and 2.5 µL/well of Propidium Iodide (PI) were then dripped in. The precipitate mixture was then pipetted and incubated while being shading at room temperature for 5 minutes, and then the ratio of Annexin V positive cells was measured using BD Accuri™ C6 Flow Cytometer (Nippon Becton Dickinson Company, Ltd.)

(Results)
(Caspase Inhibitor Suppresses Apoptosis of Corneal Endothelial Cells in Fuchs' Endothelial Corneal Dystrophy Disease Cell Model)

Figure 11:
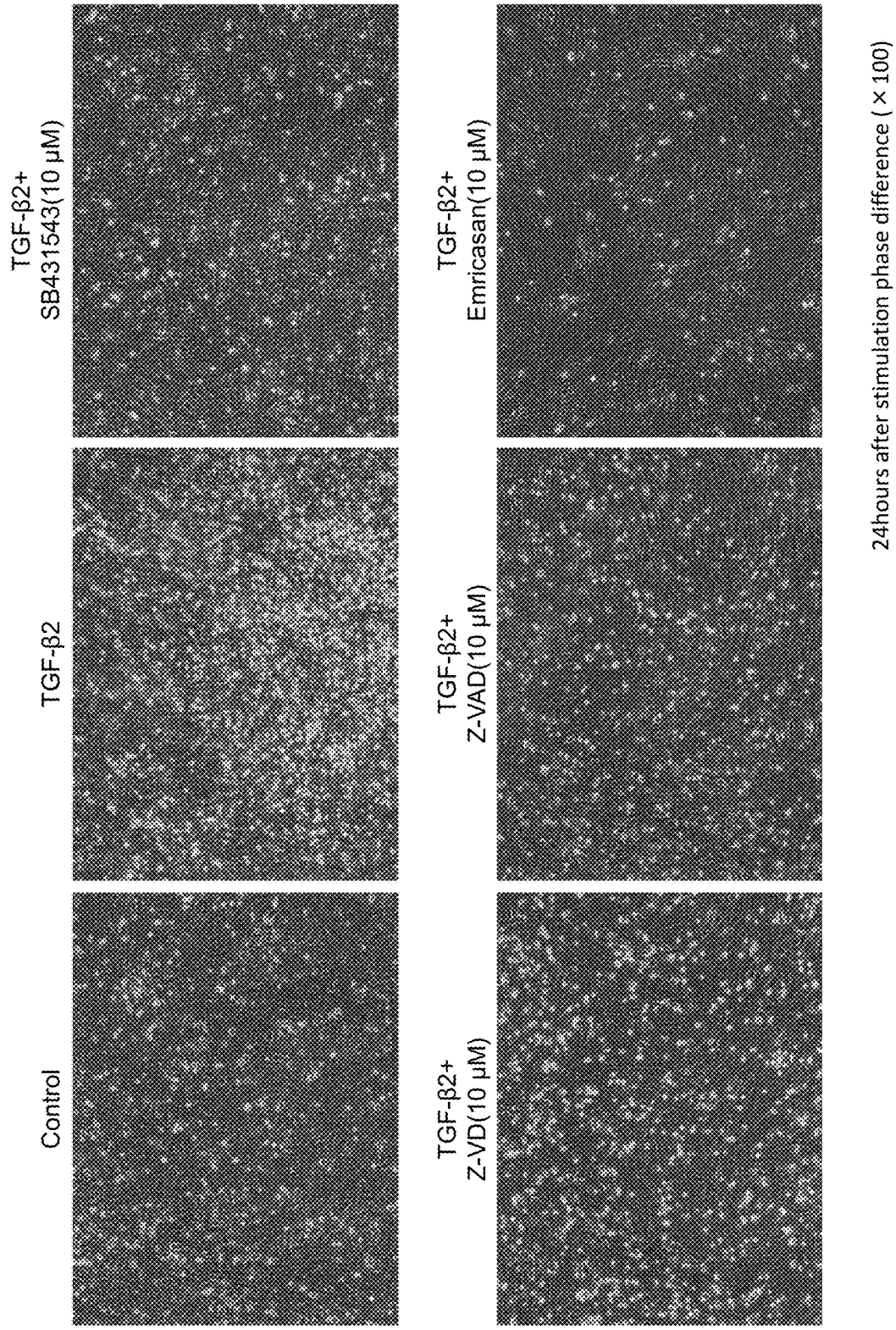
FIG. 11 shows the effect of a caspase inhibitor on damage to immobilized Fuchs' endothelial corneal dystrophy patient derived cells (iFECD) due to TGF-β2. The images show iFECDs of the control group, TGF-β2 supplemented group (10 ng/mL), TGF-β2+SB431542 supplemented group (10 μM), TGF-β2+Z-VD-FMK supplemented group (10 μM), TGF-β2+Z-VAD-FMK supplemented group (10 μM), and TGF-β2+emricasan supplemented group (10 μM). Magnification of 100× was used.

As shown in FIG. 11, significant cell death was observed in the TGF-$\beta$2 group, but it was observed that programmed cell death was suppressed in the groups supplemented with each caspase inhibitor, just as in the group supplemented with a TGF-$\beta$2 inhibitor SB431542. This result shows that caspase inhibitors can suppress cell damage due to TGF-$\beta$2 stimulation.

Figure 12:
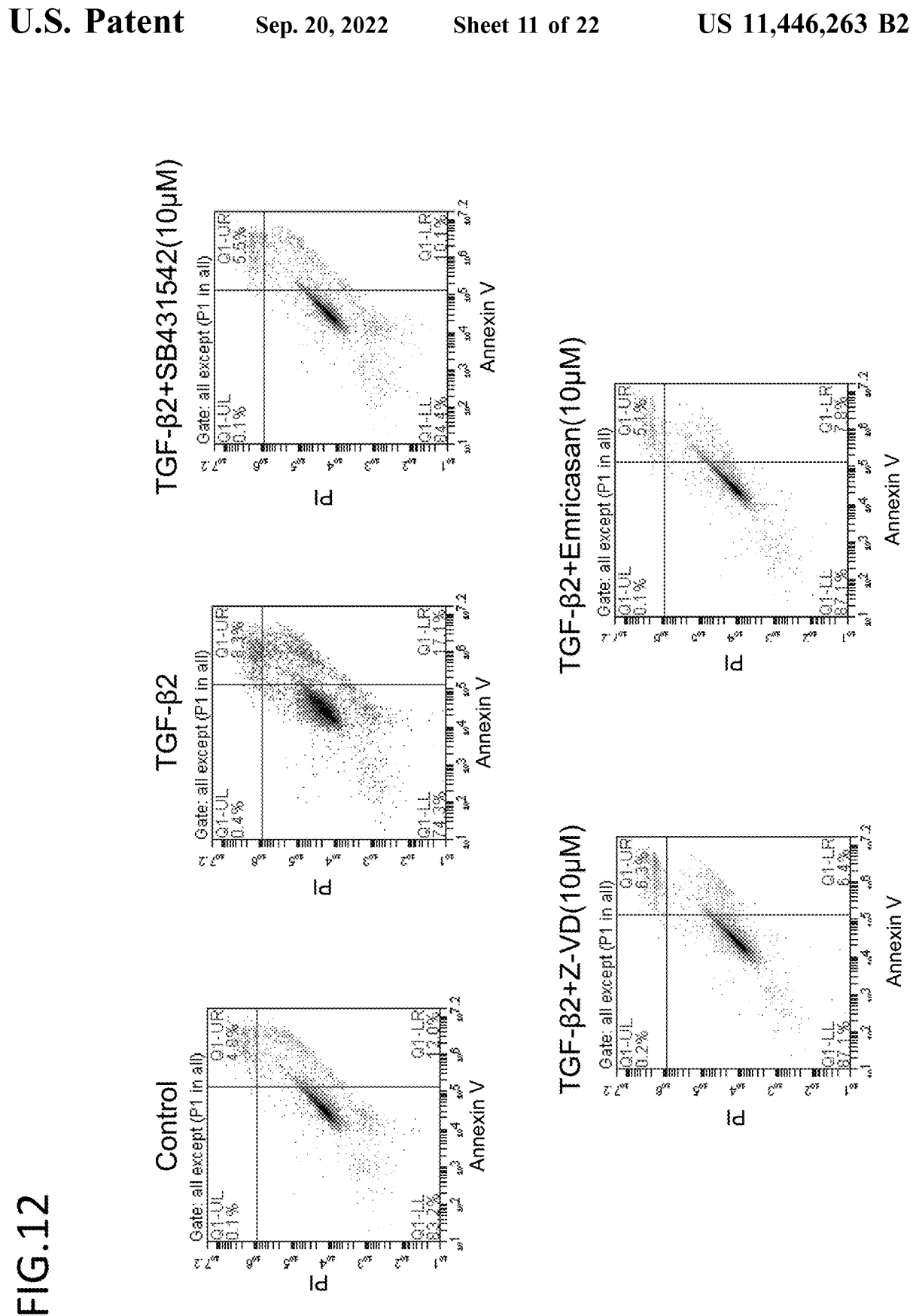
[FIG. 12]
Figure 13:
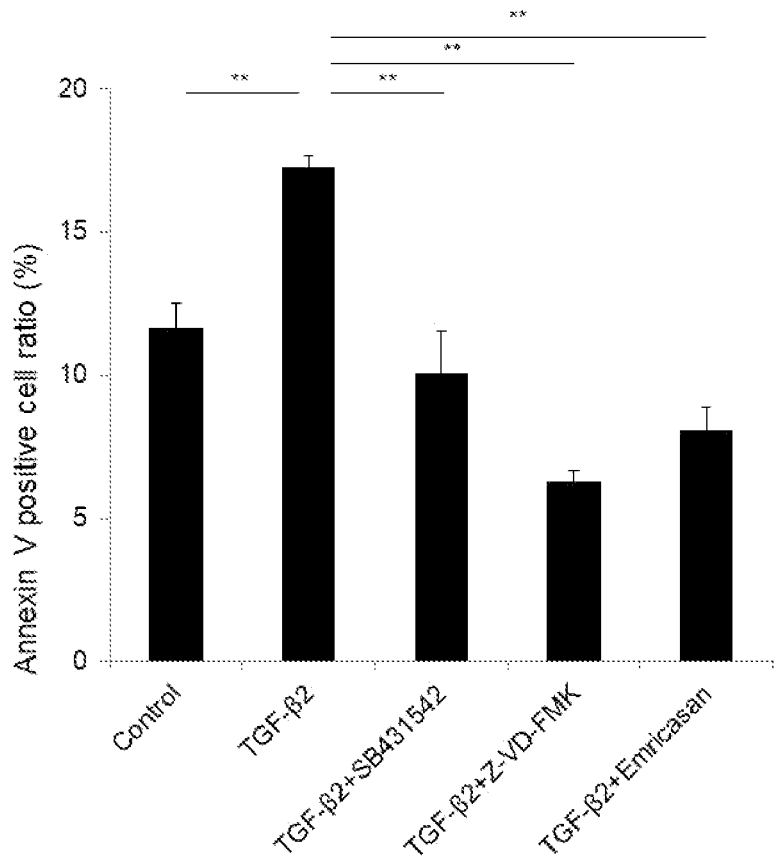
FIG. 13 shows a graph of Annexin V positive cell ratio measured by flow cytometry. The vertical axis shows the value (percentage) of Q1-LR in FIG. 12 as the Annexin V position cell ratio (%). The horizontal axis shows, from the left, the control group, TGF-β2 supplemented group, TGF-β2+SB431542 supplemented group, TGF-β2+Z-VD-FMK supplemented group, and TGF-β2+emricasan supplemented group. The data is shown as mean±SE and n=3. The p value was calculated using Dunnett's test. ** indicates statistical significance (p<0.01).

The results of flow cytometry are shown in FIGS. 12 and 13. The ratio of Annexin V position cells was lower in the caspase inhibitor supplemented groups than the TGF-$\beta$2 group. This means that a caspase inhibitor strongly suppressed damage to corneal endothelial cells induced by TGF-$\beta$2 to the same extent as TGF-$\beta$ signal inhibition despite being mediated by another pathway.

(Example 10: Caspase 3 Activation by TGF-$\beta$2 in Immobilized Fuchs' Endothelial Corneal Dystrophy Patient Derived Cells (iFECD))

This Example investigated the suppression effect of a caspase inhibitor on caspase 3 activation due to TGF-$\beta$2 in immobilized Fuchs' endothelial corneal dystrophy patient derived cells (iFECD).

(Materials and Methods)
IFECDs were cultured by the same procedure as Example 9.
1) Protein Collection The medium was collected on ice to collect free and dead cells. The solution from washing the cells twice with Dulbecco's PBS (−) (Nissui/05913) was also collected, and was centrifuged at 4° C. at 800×g for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was subjected to ultrasound waves for 3 minutes in cold water with a sonication device (BIORUPTOR, TOSHO DENKI) and centrifuged for 10 min at 4° C. at 1500 rpm to collect the supernatant of protein.

2) Western Blot

The extracted protein (9 µL was poured into each well, and the amount of protein was about 5.4 µg for Cleaved-Caspase 3 and GAPDH, and about 6.2 µg for PARP) was separated by SDS-PAGE and transferred onto a nitrocellulose membrane. Anti-GAPDH mAb (Medical & Biological Laboratories Co., Ltd./M171-3), PARP Antibody (CST Japan, K.K/9542S), and Caspase-3 Antibody (CST Japan, K.K/9662S) were used as the primary antibodies. ECL Mouse IgG, HRP-Linked Whole Ab (from sheep) (GE Healthcare Life Sciences/NA931V), ECL Rabbit IgG, and HRP-linked whole Ab (from donkeys) (GE Healthcare Life Sciences/NA934V) were used as the secondary antibodies. For the primary antibodies, Anti-GAPDH mAb: 3000-fold dilution, PARP Antibody: 2000-fold dilution, and Caspase-3 Antibody: 1000-fold dilution, while the secondary antibody was diluted 5000-fold. Chemi Lumi ONE Ultra (nacalai tesque, 11644-40) was used for detection. The detected band strength was analyzed with a lumino image analyzer LAS-4000 mini (Fuji Film) and ImageQuant™ software (GE Healthcare).

(Results)

(Caspase Inhibitor Suppresses Caspase 3 Activation in Fuchs' Endothelial Corneal Dystrophy Disease Cell Model)

Figure 14:
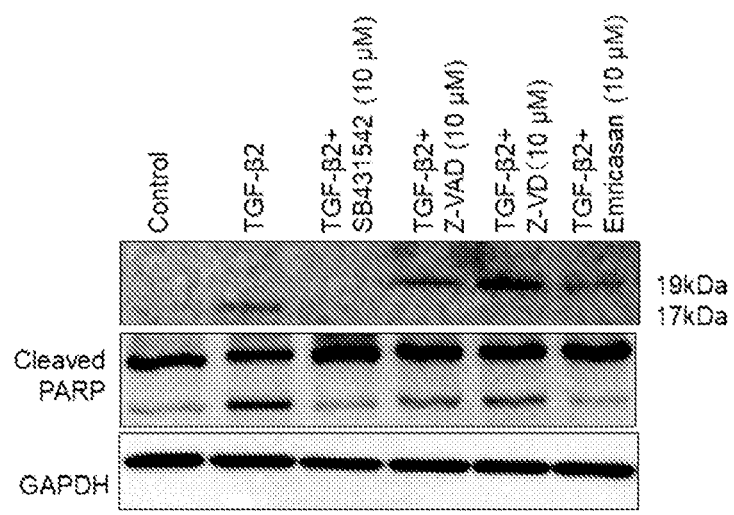
FIG. 14 shows the effect of a caspase inhibitor on cell damage to a Fuchs' endothelial corneal dystrophy disease cell model due to TGF-β2. The results of the western blots of caspase 3, PARP, and GAPDH are shown. The figure shows, from the left, the control group, TGF-β2 supplemented group, TGF-β2+SB431542 supplemented group (10 μM), TGF-β2+Z-VAD-FMK supplemented group (10 μM), TGF-β2+Z-VD-FMK supplemented group (10 μM), and TGF-β2+emricasan supplemented group (10 μM).

The results of the western blots are shown in FIG. 14. As shown, a band of active form cleaved caspase 3 (about 17 kDa) was not observed in the caspase inhibitor supplemented groups, which demonstrates that caspase inhibitors suppress caspase 3 activation in a Fuchs' endothelial corneal dystrophy disease cell model.

Example 11: Examination of Effect of Caspase Inhibitor on Cornea Preservation Using Rabbit Cornea This example examined the effect of a caspase inhibitor on cornea preservation using a rabbit cornea.

(Materials and Methods)

Rabbit eye balls after 0 to 24 hours from euthanasia were used in the experiment. Under a stereoscopic microscope, the sclera was excised using spring scissors along the corneal limbus, and the lens and iris were removed to prepare a sclerocornea fragment. The sclerocornea fragment was divided into two pieces as the control group and emricasan supplemented groups. After dividing the cornea, the control group was left standing in DMSO supplemented Optisol-GS® (Bausch & Lomb) and the caspase inhibitor supplemented groups were left standing in Optisol-GS® supplemented with emricasan for 2 weeks at 4° C.

After washing the sclerocornea fragment with PBS (−), the fragment was immobilized with 4% formaldehyde for 10 minutes at room temperature (RT) and incubated for 60 minutes with 1% bovine serum albumin (BSA). Antibodies to N-cadherin (BD Bioscience) and ZO-1 (Zymed Laboratories) were used at 1:300 dilution. For secondary antibodies, Alexa Fluor® 488 labeled goat anti-mouse IgG (Life Technologies, A11009) was used at a dilution of 1:1000. A 1:400 dilution of phalloidin (Life Technologies) 546 was used for actin staining. The nucleus of cells was then stained with DAPI (Cell stain DAPI Solution; Dojindo, Kumamoto, Japan). Fluorescence was observed using a confocal microscope (TCS SP2 AOBS; Leica Microsystems, Wetzlar Germany). Cells found to have actin contractile rings under a fluorescence microscope were counted to measure the ratio.

(Results)

(Emricasan Suppresses Corneal Endothelial Cell Damage During Cornea Preservation Due to the Addition Thereof into Cornea Preservation Solution)

Figure 15:
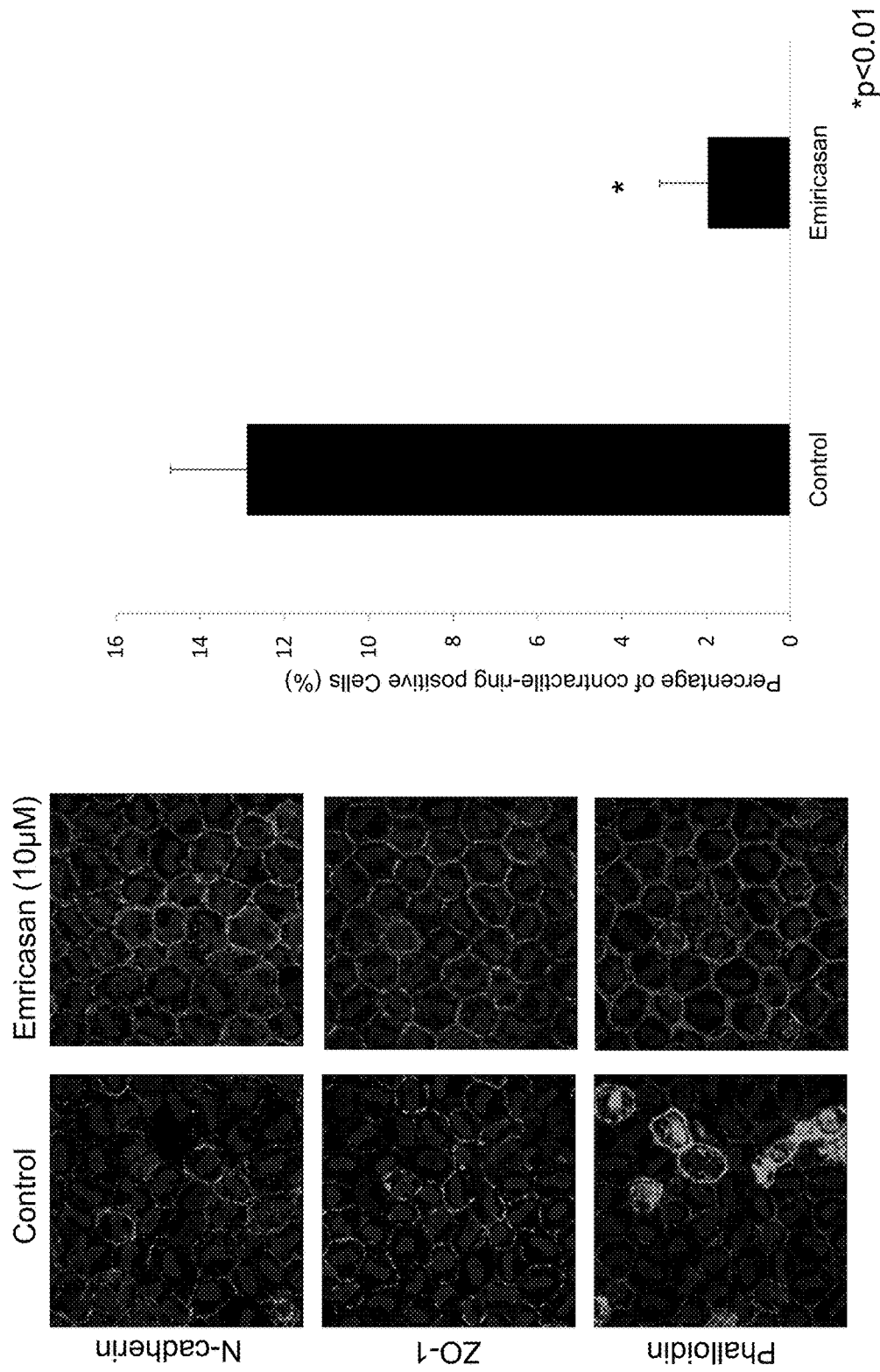
FIG. 15 shows the effect of a caspase inhibitor on cornea preservation using rabbit corneas. The top row of the left panel shows fluorescence images for N-cadherin, the middle row shows fluorescence images for ZO-1, and the bottom row shows fluorescence images for Phalloidin. The left column shows the control group and the right column shows the emricasan supplemented group (10 μM). The right graph shows the percentage of cells that were found to have actin contractile ring formation (%) in the vertical axis. The left bar shows the control group and the right bar shows the emricasan supplemented group. * indicates statistical significance (p<0.01).

The results are shown in FIG. 15. As can be seen from the fluorescence images after 2 weeks of preservation at 4° C., the control group had cell damage, while the emricasan supplemented group had hardly any cell damage after 2 weeks of preservation at 4° C. or had any morphological abnormality observed in the cells. Further, emricasan significantly suppressed actin contractile rings found from cell damage.

Example 12: Examination of Cryopreservation Solution

This Example examined cryopreservation solutions.

(Materials and Methods)

Fetal bovine serum and DMSO (Nacalai Tesque) were added to commercially available CELL BANKER PLUS (Takara Bio catalog number: CB021), CELL BANKER 2 (Takara Bio catalog number: CB031), STEM-CELL-BANKER (Takara Bio catalog number: CB043), KM BANKER (Kohjin Bio catalog number: KOJ-16092005), Freezing Medium, Animal Component Free, CRYO Defined (CnT-CRYO) (CELLNTEC catalog number: CnT-CRYO-50), and OptiMEM (INVITROGEN) to be 10% (v/v) for use as a cryopreservation solution.

The test used Opti-MEM I Reduced-Serum Medium, Liquid (INVITROGEN catalog number: 31985-070)+8% fetal bovine serum (FBS) (BIOWEST, catalog number: S1820-500)+200 mg/ml $CaCl_2 \cdot 2H_2O$ (SIGMA catalog number: C7902-500G)+0.08% chondroitin sulfate (SIGMA catalog number: C9819-5G)+20 µg/ml ascorbic acid (SIGMA catalog number: A4544-25G)+50 µg/ml gentamicin (INVITROGEN catalog number: 15710-064)+5 ng/ml EGF (INVITROGEN catalog number: PHG0311) conditioned for MSC feeder cells. Human corneal endothelial cells cultured in the medium described above were used. The cells were suspended into each cryopreservation solution so that the cell concentration was 100,000 cells/mL, and 1 mL of each solution was placed in a cryotube (CORNING, catalog number: 430488). The freezing tubes were then placed in a BICELL (Nihon Freezer, catalog number: BICELL) and stored for 10 days at −80° C., and then thawed by immersing the tubes in a water bath at 37° C. After thawing, the cells were washed in a medium, and the live cell count and dead cell count were measured by trypan blue dye exclusion test.

The survival rate for each cryopreservation solution was calculated by the following equation.

Viability rate=live cell count/(live cell count+dead cell count)×100

Further, 10000 cells were dispensed to calculate the viability rate with CellTiter-Glo Luminescent Cell Viability Assay (Promega catalog number: G7570).

(Results)

(KM Banker Superbly Suppresses Damage to Corneal Endothelial Cells in Various Commercially-Available Cryopreservation Solutions)

The results are shown in FIG. 16. A difference was not found in the ratio of trypan blue negative cells among cryopreservation solutions. However, the cell viability rate calculated by quantifying ATP from cells with higher metabolic activity was the highest with Km banker and was hardly different in the control.

Example 13: Cell Survival after Freezing Corneal Endothelial Cells in Various Cryopreservation Solutions In this Example, cell survival after freezing corneal endothelial cells in various cryopreservation solutions was observed.

(Materials and Methods)

The same cryopreservation and thawing of corneal endothelial cells as Example 12 were performed.

After thawing, cells were seeded on a 96-well plate coated with laminin E8 (Veritas) at 5000 cells per well, and cultured in the presence and absence of Y27632. After three days of culturing, phase difference microscope images were taken (magnification: ×100).

Further, calibration curves were drawn using frozen cells and cells of the same lot. CellTiter-Glo Luminescent Cell Viability Assay (Promega, catalog number: G7570) was performed to measure the cell count (n=6).

(Results)

(KM Banker Promotes Cell Survival after Freezing of Corneal Endothelial Cells)

Figure 17:
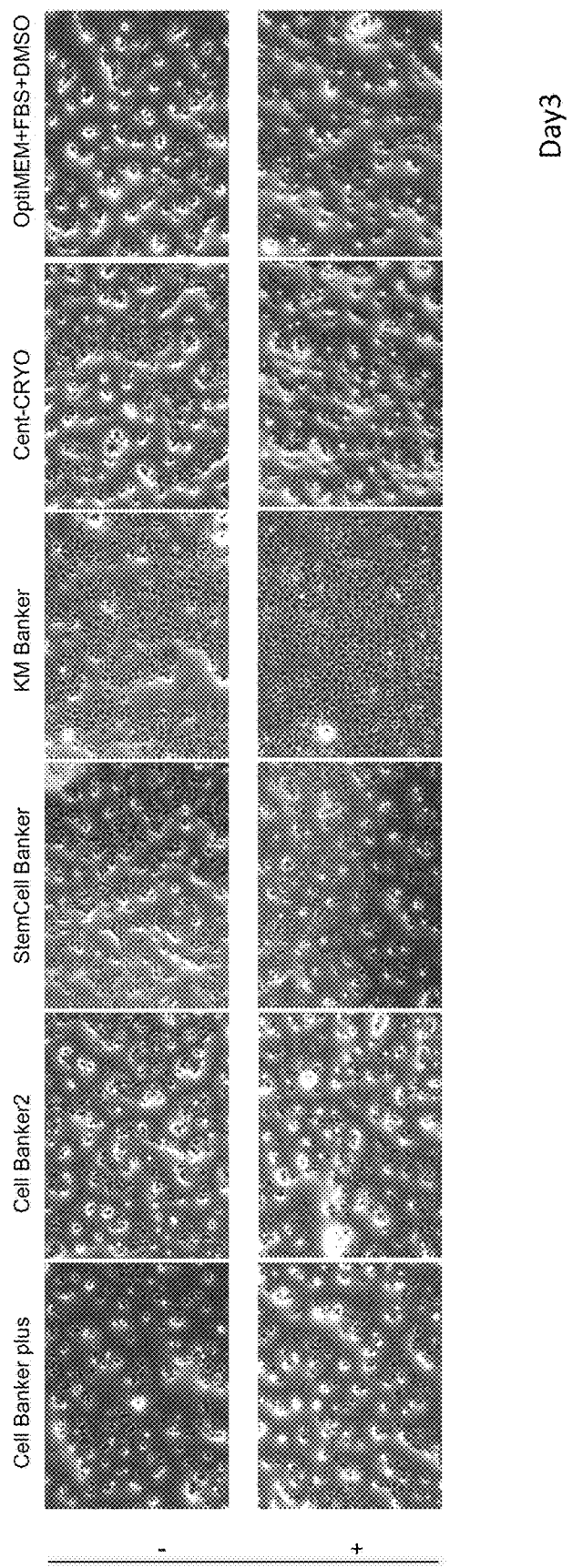
FIG. 17 shows phase difference microscope images from observing the post-freezing survival of corneal endothelial cells in various cryopreservation solutions. The top row shows phase difference microscope images of corneal endothelial cells cultured in the absence of Y27632, and the bottom row shows phase difference microscope images of corneal endothelial cells cultured in the presence of Y27632. The images show, from the left, the used preservation solution, CELL BANKER PLUS, CELL BANKER 2, STEM-CELLBANKER, KM BANKER, CnT-CRYO, and OptiMEM+10%FBS+10%DMSO.
Figure 18:
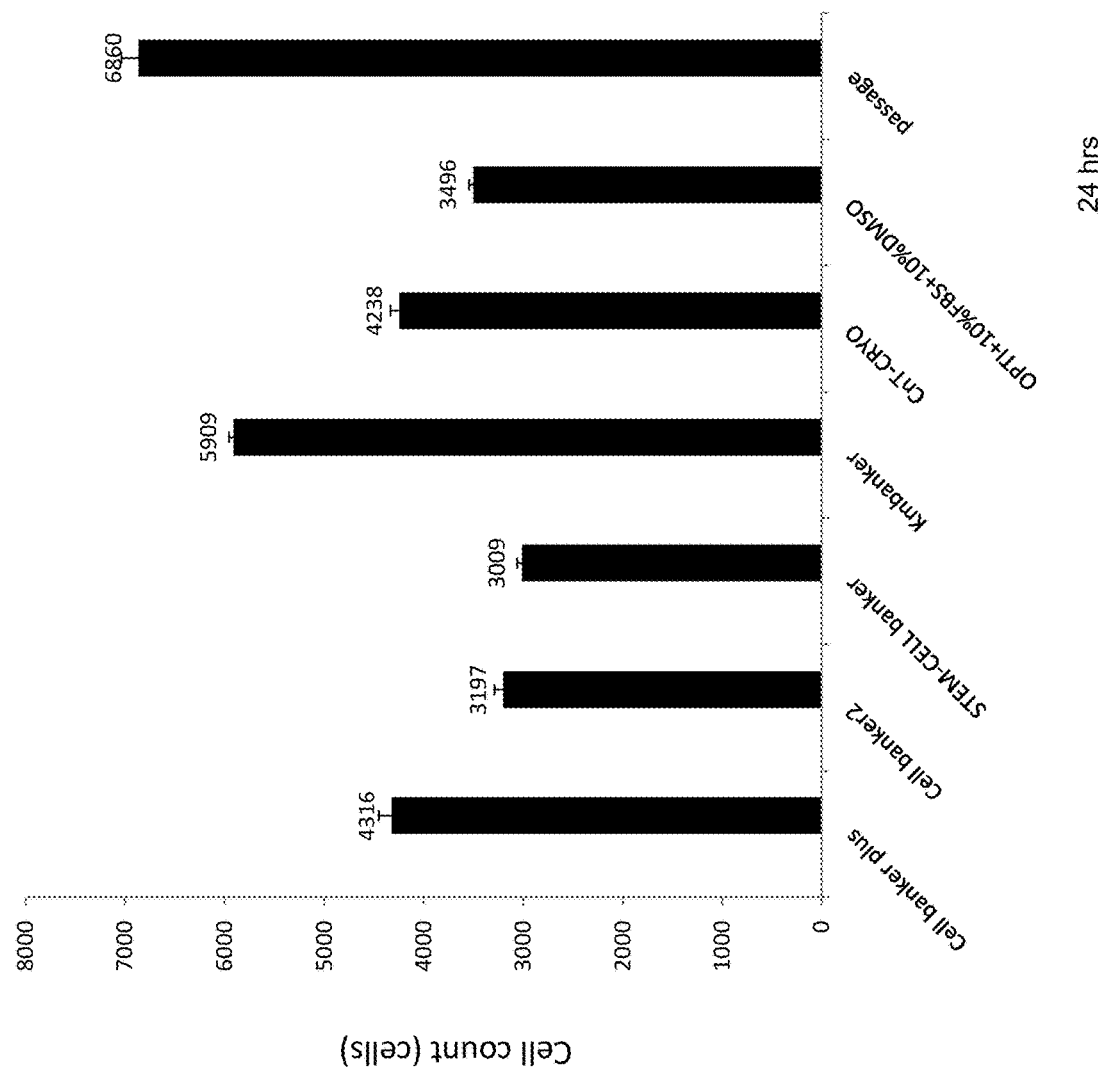
FIG. 18 shows a graph of post-freezing cell count of corneal endothelial cells in various cryopreservation solutions. The vertical axis shows the cell count (cells), and the horizontal axis shows, from the left, CELL BANKER PLUS, CELL BANKER 2, STEM-CELLBANKER, KM BANKER, CnT-CRYO, OptiMEM+10%FBS+10%DMSO, and non-cryopreserved passaged cells.

It was observed that cell survival has been promoted when KM banker was used, as can be seen from the microscope images shown in FIG. 17. Furthermore, when KM banker was used, the cell count was slightly less compared to passaged cells that did not undergo cryopreservation, but a significantly higher cell count was exhibited compared to a case using other cryopreservation solutions, as shown in FIG. 18. This shows that KM banker promotes survival of corneal endothelial cells after cryopreservation.

Example 14: Promotion of Corneal Endothelial Cell Culture after Cryopreservation of Corneal Endothelia by Caspase Inhibition of Z-VD-FMK This Example investigated the effect of caspase inhibition of Z-VD-FMK in corneal endothelial cell culture after cryopreservation of corneal endothelia.

(Materials and Methods)

The test used human corneal endothelial cells cultured in MSC-CM (MSC conditioned medium). The medium was removed from the culture dish in which human corneal endothelial cells were being cultured, and the cells were supplemented with PBS (−) that was preheated to 37° C., and were washed. This was repeated twice. After removing the PBS (−), the cells were supplemented with TrypLE Select (×10) (GIBCO, A12177-01) and incubated for 10 minutes at 37° C. (5% $CO_2$). The cells were then cryopreserved with KM BANKER. After preservation for three days at −80° C., the tube was immersed in a 37° C. water bath and thawed. Further, 100000 cells were seeded on a 12-well plate coated with laminin E8 and supplemented with Z-VD-FMK so that the final concentration as of the seeding was 5 µmol/L. DMSO was added for the group that was not supplemented with Z-VAD-FMK.

(Results)

(Z-VD-FMK Promotes the Culturing of Corneal Endothelial Cells after Cryopreservation of Corneal Endothelia)

As shown in FIG. 19, when a caspase inhibitor Z-VD-FMK was added, cell growth was promoted in corneal endothelial cell culture after cryopreservation. Therefore, it was revealed that caspase inhibitors are useful in the growth of corneal endothelial cells.

Example 15: Reduction in Cell Damage in Corneal Endothelium Cryopreservation Due to Z-VD-FMK This Example investigated the reduction in cell damage in corneal endothelium cryopreservation due to Z-VD-FMK.

(Materials and Methods)

The test used human corneal endothelial cells cultured in MSC-CM. The medium was removed from a culture dish in which the human corneal endothelial cells were being cultured, and the cells were supplemented with PBS (−) that was preheated to 37° C., and were washed. This was repeated twice. After removing the PBS (−), the cells were supplemented with TrypLE Select (×10) (GIBCO, A12177-01) and incubated for 10 minutes at 37° C. (5% $CO_2$). The cells were then cryopreserved with KM BANKER by adding Z-VD-FMK (Wako Pure Chemical Industries, catalog number: 262-02061) so that the final concentration was 10 µmol/L. A solvent of a reagent, i.e., DMSO (Dimethyl Sulfoxide Sterile-filtered; nacalai tesque, 13408-64), was added to the control group.

After preservation for three days at −80° C., the tube was immersed in a 37° C. water bath and thawed. After thawing, the cells were washed in a medium, and the live cell count and dead cell count were measured by trypan blue dye exclusion test. Further, 10000 cells were seeded on a 96-well plate coated with laminin E8 and supplemented with Z-VD-FMK so that the final concentration as of the seeding was 5 µmol/L, or supplemented with SB203580 (Cayman, catalog number: 13067) so that the final concentration was 10 µmol/L. DMSO was added for groups that were not supplemented with Z-VAD-FMK or SB203580. After 24 hours from seeding, CellTiter-Glo Luminescent Cell Viability Assay (Promega catalog number: G7570) was performed and the amount of luminescence was measured.

(Results)

(Caspase Inhibition by Z-VD-FMK Reduces Cell Damage Due to Corneal Endothelium Cryopreservation)

Figure 20:
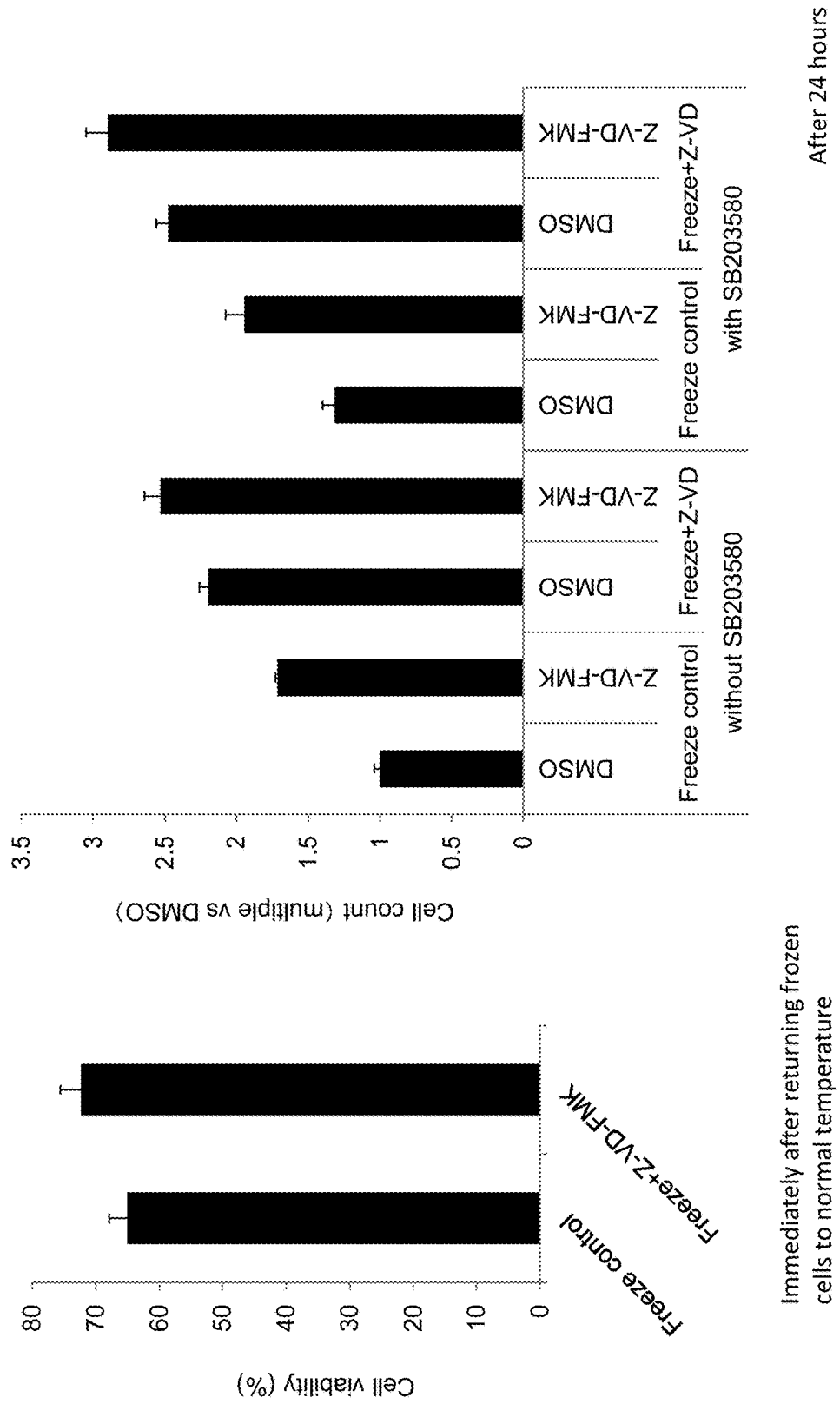
FIG. 20 shows the decrease in cell damage in corneal endothelium cryopreservation due to Z-VD-FMK. The left graph shows the cell viability (%) immediately after returning frozen cells to normal temperature. The left bar shows Freeze control in which Z-VD-FMK was not added to the cryopreservation solution, and the right bar shows Freeze+Z-VD-FMK, in which Z-VD-FMK was added to the cryopreservation solution. The right graph shows the cell count after 24 hours from thawing the cells and adding DMSO or Z-VD-FMK. Four groups on the left are groups that were not supplemented with SB203580, and the four groups on the right are groups supplemented with SB203580. The graph shows, from the left, DMSO supplemented group of Freeze control, Z-VD-FMK supplemented group of Freeze control, DMSO supplemented group of Freeze+Z-VD-FMK, and Z-VD-FMK supplemented group of Freeze+Z-VD-FMK.

This Example investigated the effect of a caspase inhibitor on cell viability rate in cryopreservation and the effect of a caspase inhibitor added after cryopreservation on cell count. The cell viability rate immediately after returning frozen cells to normal temperature was higher when adding Z-VD-FMK to a cryopreservation solution (Freeze+Z-VD-FMK) than a case without such addition (Freeze control) (FIG. 20, left). When Z-VD-FMK was added after cryopreservation in the Freeze control group, cell damage was suppressed, and the cell count was about 1.7-fold compared to the case where DMSO was added after cryopreservation. In the Freeze+Z-VD-FMK group, the cell count was about 2.2-fold when DMSO was added after cryopreservation. When Z-VD-FMK was further added after cryopreservation, the cell count was about 2.5-fold. A synergistic effect was confirmed when a p38 MAPK inhibitor SB203580 was added.

Example 16: Z-VD-FMK Promotes Cell Culture after Freezing when Added to Multiple Cryopreservation Solutions (Materials and Methods)

The test used human corneal endothelial cells cultured in MSC-CM. The medium was removed from a culture dish in which the human corneal endothelial cells were being cultured, and the cells were supplemented with PBS (−) that was preheated to 37° C., and were washed. This was repeated twice. After removing the PBS (−), the cells were supplemented with TrypLE Select (×10) (GIBCO, A12177-01) and incubated for 10 minutes at 37° C. (5% $CO_2$). The cells were then cryopreserved using Cell BANKER and KM BANKER as the cryopreservation solutions. DMSO was used for the control group. After preservation for three days at −80° C., the tube was immersed in a 37° C. water bath and thawed.

Further, 10000 cells were seeded on a 96-well plate coated with laminin E8 and supplemented with Z-VD-FMK so that the final concentration as of the seeding was 5 µmol/L, or supplemented with Y27632 (Wako Pure Chemical Industries, catalog number: 253-00513) so that the final concentration was 5 µmol/L. DMSO was added to groups that were not supplemented with Z-VAD-FMK or Y27632. After 24 hours from seeding, CellTiter-Glo Luminescent Cell Viability Assay (Promega catalog number: G7570) was performed and the amount of luminescence was measured with GROWMAX (Promega).

(Results)
(Z-VD-FMK Promotes Cell Culture after Freezing when Added to Multiple Cryopreservation Solutions)

Figure 21:
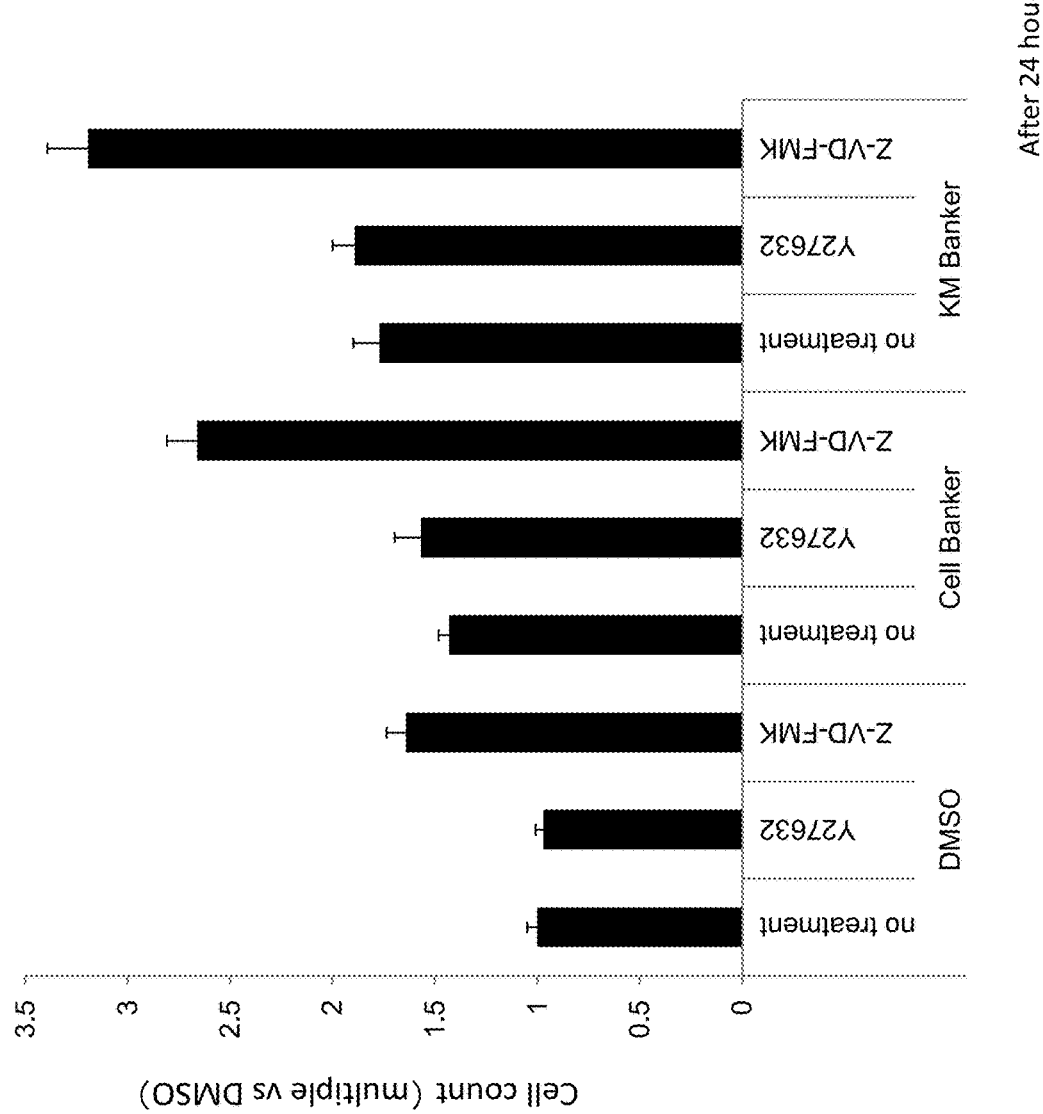
FIG. 21 shows that Z-VD-FMK promotes cell culture after freezing when added to multiple preservation solvent. The graph shows, from the left, groups using a DMSO supplemented medium, Cell Banker, and KM Banker as the cryopreservation solutions. In each group, the graph shows, from the left, data for no addition after cryopreservation (DMSO group), addition of Y27632 (5 μM), and addition of Z-VD-FMK (5 μM). The vertical axis shows the change in multiple with respect to the cell count in the DMSO group.

The results are shown in FIG. 21. As shown, it was observed that the cell count was significantly higher when Z-VAD-MK was added after cryopreservation compared to when Z-VAD-MK was not added. It can also be understood that the effect of Z-VAD-MK is the same whether Cell Banker or KM Banker was used as a cryopreservation solution. Therefore, it is demonstrated that Z-VAD-MK promotes cell culture similarly regardless of which cryopreservation solution Z-VAD-MK is added.

Example 17: Suppression Effect of Caspase Inhibitor on Fibronectin Production Due to TGFβ

This Example confirmed that a caspase inhibitor suppresses extracellular matrix production of corneal endothelial cells due to TGF-β2.
(Fluorescence Observation)
(Materials and Methods)

Round glass was placed on a 24-well plate, disinfected for 5 minutes with ethanol, and coated with laminin-511 E8 Fragment. Then, iFECDs were seeded at $4.0 \times 10^5$ each and cultured at 37° C. (5% $CO_2$) until reaching 60 to 70% confluence. Dulbecco's Modified Eagle Medium (DMEM, nacalai tesque, 08456-36)+10% FBS (Thermo Fisher Scientific, S1820-500)+1% penicillin-streptomycin (nacalai tesque, 26252-94) was used as the medium. SB431542 (Wako Pure Chemical Industries, Ltd./192-16541), Z-VD-FMK (isomer mixture) (Wako Pure Chemical Industries, Ltd./262-02061), and emricasan (CHEMSCENE, LLC/CS-0599) were then added at a concentration of 10 μM, and the cells were incubated for 24 hours. The medium was exchanged in the control group and the TFG-β2 supplemented group. DMEM+2% FBS+1% P/S was used as the medium. TGF-β2 alone (10 ng/mL), or both TGF-β2 (10 ng/mL) and each inhibitor (10 μM) were then added. After 24 hours, immunostaining was performed by the following method.

Cells after 24 hours form stimulation were washed with PBS (−) and immobilized with 4% PFA for 10 minutes at room temperature. 0.5% Triton was used for 5 minutes for permeation treatment, and 1% BSA was used for blocking for 1 hour. Primary antibodies were reacted at room temperature for one hour or overnight. Antibodies to fibronectin (BD Biosciences, 610077) were used at this time at a dilution of 1:400. Alexa 488 labeled goat antibody mouse IgG (Life Technologies, A11009) diluted 1:1000 was used for the secondary antibodies. Furthermore, cell nucleus was stained with DAPI (Cell stain DAPI Solution; Dojindo, Kumamoto, Japan) diluted to 1:2000. A confocal microscope (Leica Microsystems CMS GmcH Am Friendensplatz 3 68165 Mannheim, Germany) was used to observe fluorescence.

(Confirmation of Expression by Western Blot)
(Materials and Methods)

IFECDs were seeded at $1.0 \times 10^5$ each on a 12-well plate and cultured at 37° C. (5% $CO_2$) until reaching 60 to 70% confluence. Dulbecco's Modified Eagle Medium (DMEM, nacalai tesque, 08456-36)+10% FBS (Thermo Fisher Scientific, S1820-500)+1% penicillin-streptomycin (nacalai tesque, 26252-94) was used as the medium. SB431542 (Wako Pure Chemical Industries, Ltd./192-16541), Z-VD-FMK (isomer mixture) (Wako Pure Chemical Industries, Ltd./262-02061), and emricasan (CHEMSCENE, LLC/CS-0599) were then added at a concentration of 10 μM, and the cells were incubated for 24 hours. The medium was exchanged in the control group and the TFG-β2 supplemented group. DMEM+2% FBS+1% P/S was used as the medium. TGF-β2 alone (10 ng/mL), or both TGF-β2 (10 ng/mL) and each inhibitor (10 μm) were added. After 24 hours, proteins were collected by the following method.

(1) Protein Collection

The medium was collected on ice to collect free and dead cells. The solution from washing the cells twice with 1×PBS (−) was also collected, and was centrifuged at 4° C. at 800×g for 15 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized for 3 minutes with a sonication device (BIORUPTOR, TOSHO DENKI) and centrifuged for 10 min (4° C. at 15000 rpm) to collect the supernatant of protein.

2) Western Blot

8 μg of the extracted protein was separated by SDS-PAGE and transferred onto a nitrocellulose membrane. A rabbit anti-fibronectin antibody (BD Biosciences, 610077), rabbit anti-Smad2 antibody (Cell Signaling, 5339P), rabbit anti-p-Smad2 antibody (Cell Signaling, 3108S) and mouse anti-GAPDH antibody (MBL, M171-3) were used as the primary antibodies. A peroxidase-labeled anti-rabbit antibody and anti-mouse antibody (GE Healthcare Biosciences, NA934V, NA931V) were used as the secondary antibodies. For the primary antibodies, mouse anti-Fibronectin antibody was diluted 20000-fold, rabbit anti-Smad2 antibody and rabbit anti-p-Smad2 antibody was diluted 1000-fold dilution, and GAPDH was diluted 3000-fold dilution, while the secondary antibody was diluted 5000-fold.

Chemi Lumi ONE Ultra (nacalai tesque, 11644-40) was used for detection. The detected band strength was analyzed with Amersham™ Imager 600 (GE Healthcare).

(Results)

Figure 22:
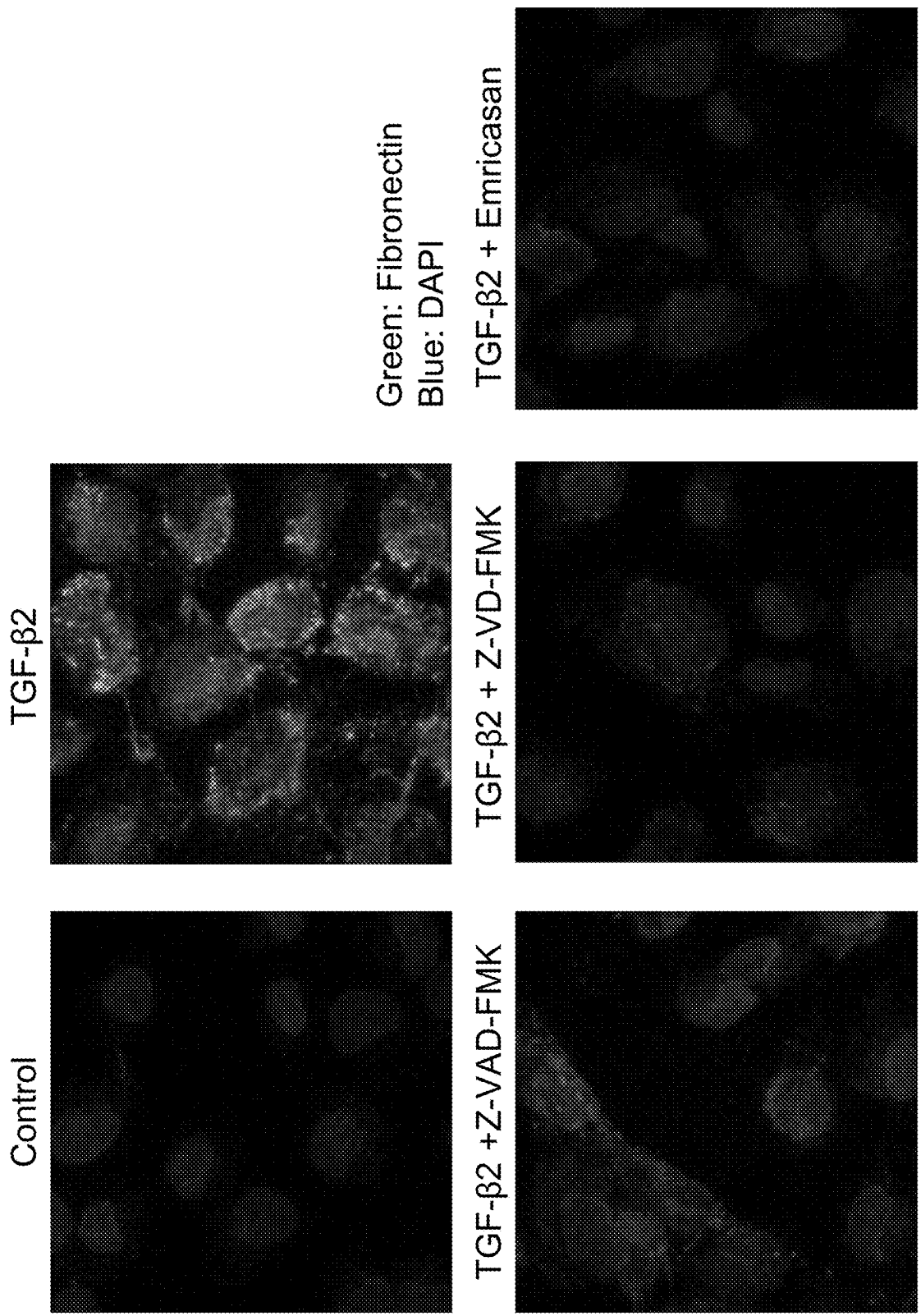
FIG. 22 shows the suppression effect of a caspase inhibitor on overexpression of fibronectin due to TGF-β2 in immobilized Fuchs' endothelial corneal dystrophy patient derived cells (iFECD).
Figure 23:
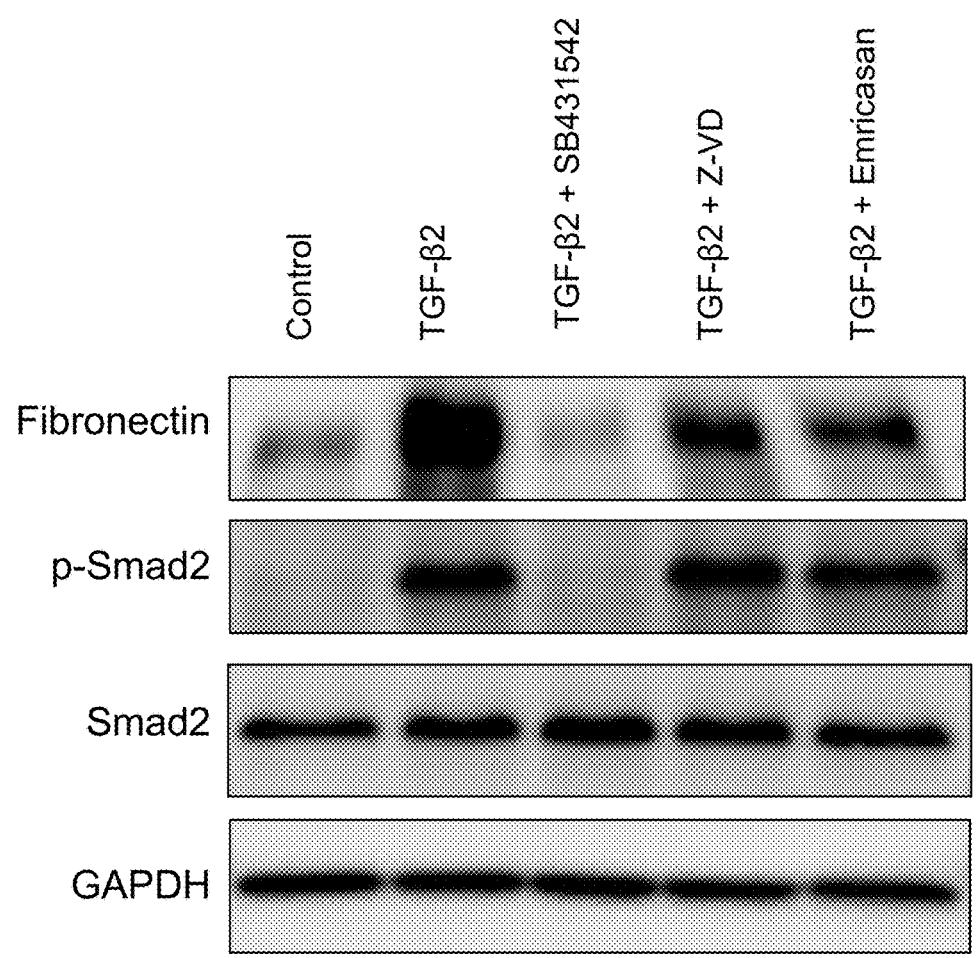
FIG. 23 shows the results of the western blots of fibronectin, p-Smad2, Smad2, and GAPDH in immobilized Fuchs' endothelial corneal dystrophy patient derived cells (iFECD).
Figure 24:
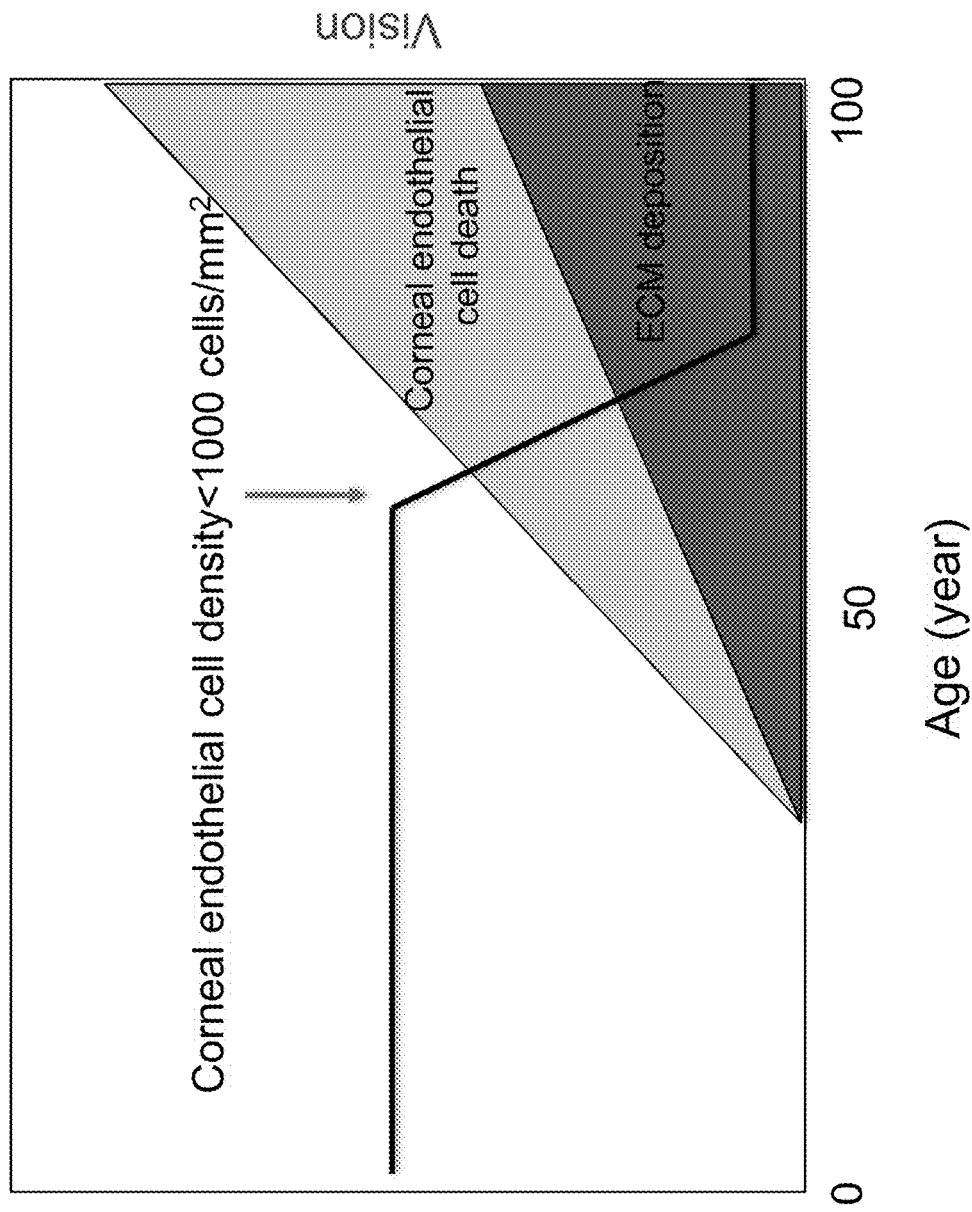
FIG. 24 shows a schematic diagram of the relationship of vision with corneal endothelial cells and ECM deposition. The diagram shows that vision deteriorates as corneal endothelial cells and ECM deposition increases. Thickening of the Descemet's membrane or guttae due to ECM deposition commonly starts developing in the 30s and 40s in Fuchs' endothelial corneal dystrophy patients, and progresses throughout the patients' lives. Progression results in visual impairment such as blurred vision, halo, glare, or reduced vision. While corneal endothelial cell 1 death progresses, concurrently, the transparency of a cornea is maintained by the remaining corneal endothelia compensating for the pumping function until the corneal endothelial cell density is below about 1000 cells/mm$^2$. If the density is below about 1000 cells/mm$^2$, infiltration of the anterior aqueous humor into the cornea leads to corneal edema, resulting in severe visual impairment. The present technique can maintain visual function by suppressing both ECM deposition and corneal endothelial cell death.

The results are shown in FIGS. 22 and 23. This Example examined the effect of a caspase inhibitor on extracellular matrix production due to TGF-β2 stimulation. In the TGF-β2 supplemented group, expression of fibronectin increased compared to the control. In contrast, the expression decreased in the TGF-β2+caspase inhibitor supplemented groups. Further, expression of phosphorylated Smad2 (p-Smad2) was found in the TGF-β2 supplemented group and TGF-β2+caspase inhibitor groups.

DISCUSSION

As apparent from FIGS. 22 and 23, overexpression of fibronectin was found in the TGF-β2 supplemented group. In the TGF-β2 inhibitor SB431542 supplemented group, overexpression of fibronectin due to TGF-β2 was suppressed. In addition, Smad2 phosphorylated by TGF-β2 stimulation was not found. On the other hand, in the caspase inhibitor Z-VD-FMK or emricasan supplemented groups, p-Smad2 was found despite overexpression of fibronectin being suppressed. This suggests that caspase inhibitors suppress overexpression of fibronectin through a different pathway than TGF-β2 signals. In fact, caspases were known to be involved in cell death, but it was not known that caspases are involved in expression of extracellular matrix. Therefore, it was unexpected that caspase inhibitors suppress overexpression of fibronectin by a pathway that is different from those of TGF-β2 signals.

In Fuchs' endothelial corneal dystrophy, overproduction of extracellular matrix such as fibronectin and deposition thereof on the Descemet's membrane results in a disorder such as thickening of the Descemet's membrane or guttae formation. Such disorder commonly starts developing in the 30s and 40s in Fuchs' endothelial corneal dystrophy patients, and progresses throughout the patient's life. Progression results in visual impairment such as blurred vision, halo, glare, or reduced vision. While corneal endothelial cells are continually damaged in Fuchs' endothelial corneal dystrophy, the transparency of the corneal is maintained by the remaining corneal endothelia compensating for the pumping function until the corneal endothelial cell density is below about 1000 cells/mm$^2$. If the density is below about 1000 cells/mm$^2$, infiltration of anterior aqueous humor into the cornea leads to corneal edema, resulting in visual impairment (FIG. 23). In this manner, Fuchs' endothelial corneal dystrophy patients suffer from a visual function disorder due to mainly two causes, i.e., overproduction of extracellular matrix and corneal endothelial cell death. The caspase inhibitor in the present invention have a role in both suppression of extracellular matrix production and suppression of corneal endothelial cell death to be especially useful in the therapy of Fuchs' endothelial corneal dystrophy.

Example 18: Formulation Example: Cornea Preservation Solution Containing Caspase Inhibitor As a formulation example, this Example manufactures a cornea preservation solution containing a caspase inhibitor as follows.

The following preservation solution is prepared by a conventional method.

| | |
|---|---|
| Emricasan | 0.5695 mg |
| Optisol-GS (Bausch-Lomb) | optimal dose |
| Total amount | 100 mL |

Emricasan manufactured by Chemscene can be used as the emricasan.

Example 19: Preparation Example for Eye Drops

The composition of test substances at each concentration is shown below.

| | |
|---|---|
| Emricasan or suitable concentration of other caspase inhibitors | 1 to 10 mM (596.5 to 5695 mg) |
| Sodium chloride | 0.85 g |
| Sodium dihydrogen phosphate dehydrate | 0.1 g |
| Benzalkonium chloride | 0.005 g |
| Sodium hydroxide | Optimal dose |
| Purified water | Optimal dose |
| Total amount | 100 mL (pH 7.0) |

The concentration may be diluted using a base consisting of the following components.

| | |
|---|---|
| Sodium chloride | 0.85 g |
| Sodium dihydrogen phosphate dehydrate | 0.1 g |
| Benzalkonium chloride | 0.005 g |
| Sodium hydroxide | Optimal dose |
| Purified water | Optimal dose |
| Total amount | 100 mL (pH 7.0) |

Example 20: Therapy Example

The present invention is used when diagnosed with Fuchs' endothelial corneal dystrophy or a similar corneal endothelial disease (specific examples thereof include 1) observation of guttae formation, thickening of the Descemet's membrane, corneal epithelial edema, or edema of the corneal stroma by slit-lamp microscopy, 2) observation of images of guttae or corneal endothelial disorder with a specular microscope, 3) observation of corneal edema with a Pentacam, OCT, ultrasonic corneal thickness measuring apparatus, or the like, and 4) when determined as high risk by genetic diagnosis). Examples of expected use include eye drops, injection into the anterior chamber, administration using controlled-release agent, intravitreal injection, subconjunctival injection, and the like.

A commercially available substance that is compatible with the Japanese Pharmacopoeia, an equivalent product thereof or the like can be used as each component other than the active ingredient.

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application 2015-251787 filed on Dec. 24, 2015. The entire content thereof is incorporated herein by reference.

INDUSTRIAL APPLICABILITY

The present invention provides a medicament for use in treating or preventing a corneal endothelial disorder due to transforming growth factor-β (TGF-β), mitochondrial abnormality, and/or overexpression of extracellular matrix in corneal endothelial cells, especially a medicament for use in treating or preventing a corneal endothelial disorder in Fuchs' endothelial corneal dystrophy. The present invention provides a technique available to industries (pharmaceutical or the like) involved in techniques associated with formulation or the like based on such a technique.

The invention claimed is:

1. A method for treating a corneal endothelial condition, disorder, or disease due to a transforming growth factor-β (TGF-β) signal in corneal endothelial cells in a subject, comprising administering an effective amount of a caspase inhibitor to the subject.

2. The method of claim 1, wherein the condition, disorder, or disease is selected from the group consisting of Fuchs' endothelial corneal dystrophy, post-corneal transplant disorder, corneal endotheliitis, ophthalmic surgery, post-ophthalmic laser surgery disorder, posterior polymorphous dystrophy (PPD), congenital hereditary endothelial dystrophy (CHED), and idiopathic corneal endothelial disorder.

3. The method of claim 1, wherein the condition, disorder, or disease comprises Fuchs' endothelial corneal dystrophy.

4. The method of claim 3, wherein the condition is due to overproduction of extracellular matrix in Fuchs' endothelial corneal dystrophy.

5. The method of claim 4, wherein the condition comprises guttata on a corneal endothelial surface, turbid guttae of a Descemet's membrane, thickening of a Descemet's membrane, blurred vision, halo, glare, reduced vision, corneal haziness, leucoma, abnormality in visual sense, or a combination thereof.

6. A method for treating a corneal endothelial condition, disorder, or disease due to overexpression of extracellular matrix in corneal endothelial cells in a subject, comprising administering an effective amount of a caspase inhibitor to the subject.

7. The method of claim 6, wherein the condition, disorder, or disease is due to overexpression of fibronectin in corneal endothelial cells.

8. The method of claim 6, wherein the condition, disorder, or disease is selected from the group consisting of Fuchs' endothelial corneal dystrophy, guttae formation, thickening of a Descemet's membrane, thickening of a cornea, haziness, scar, corneal nebula, corneal macula, leucoma, photophobia, and blurred vision.

9. The method of claim 6, wherein the condition, disorder, or disease comprises Fuchs' endothelial corneal dystrophy.

10. The method of claim 9, wherein the subject suffers from guttae formation, thickening of a Descemet's membrane, or both.

11. A method for treating a corneal endothelial condition, disorder, or disease due to a TGF-β signal, and overexpression of extracellular matrix in corneal endothelial cells in a subject, comprising administering a caspase inhibitor to the subject.

12. The method of claim 11, wherein the condition, disorder, or disease is selected from the group consisting of Fuchs' endothelial corneal dystrophy, other endothelial corneal dystrophy, and a corneal endothelial disorder due to a drug, surgery, trauma, infection, or uveitis.

13. The method of claim 11, wherein the condition, disorder, or disease comprises Fuchs' endothelial corneal dystrophy.

14. The method of claim 1, wherein the caspase inhibitor is a caspase 3 inhibitor.

15. The method of claim 1, wherein the caspase inhibitor is selected from the group consisting of Z-VD-FMK, Z-VAD-FMK, emricasan, and nivocasan.

16. The method of claim 15, wherein a concentration of the Z-VD-FMK is about 3 μM to about 100 μM.

17. The method of claim 15, wherein a concentration of the Z-VAD-FMK is about 3 μM to about 30 μM.

18. The method of claim 15, wherein a concentration of the emricasan is about 1 μM to about 100 μM.

19. The method of claim 15, wherein a concentration of the nivocasan is about 30 μM to about 300 μM.

20. The method of claim 1 wherein the condition, disorder, or disease comprises Fuchs' endothelial corneal dystrophy, and the caspase inhibitor comprises emricasan.

* * * * *